(12) United States Patent
Lee et al.

(10) Patent No.: US 11,717,327 B2
(45) Date of Patent: Aug. 8, 2023

(54) MULTIPOINT FIXATION IMPLANTS AND RELATED METHODS

(71) Applicant: Medos International Sarl, Le Locle (CH)

(72) Inventors: Kevin Lee, Canton, MA (US); Mark Hall, Bridgewater, MA (US); Christopher Ramsay, West Wareham, MA (US); John Riley Hawkins, Cumberland, RI (US); Albert Montello, Duxbury, MA (US); Joseph Peterson, South Dartmouth, MA (US); Benjamin Johnston, Quincy, MA (US); Heiko Koller, Waldeck-Alraft (DE); Todd Albert, Penn Valley, PA (US); Christopher Ames, Mill Valley, CA (US); Bradford Currier, Rochester, MN (US); Claudius Thome, Innsbruck (AT); Masashi Neo, Kyoto (JP)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 17/124,152

(22) Filed: Dec. 16, 2020

(65) Prior Publication Data

US 2021/0100589 A1   Apr. 8, 2021

Related U.S. Application Data

(63) Continuation of application No. 15/926,069, filed on Mar. 20, 2018, now Pat. No. 10,898,232.

(51) Int. Cl.
*A61B 17/70* (2006.01)
*A61B 17/56* (2006.01)

(52) U.S. Cl.
CPC ...... *A61B 17/7034* (2013.01); *A61B 17/7044* (2013.01); *A61B 17/7058* (2013.01);
(Continued)

(58) Field of Classification Search
CPC .......... A61B 2017/564; A61B 17/7002; A61B 17/7043; A61B 17/7034
See application file for complete search history.

(56) References Cited

U.S. PATENT DOCUMENTS 5,039,265 A * 8/1991 Rath ...................... F16B 37/00
411/366.3
5,133,717 A   7/1992 Chopin
(Continued)

FOREIGN PATENT DOCUMENTS

CN  101166477 B   2/2011
EP  2 266 483 A1   12/2010
(Continued)

OTHER PUBLICATIONS

U.S. Appl. No. 15/073,020, filed Mar. 17, 2016, Multipoint Fixation Implants.
(Continued)

*Primary Examiner* — Tessa M Matthews
(74) *Attorney, Agent, or Firm* — Barnes & Thornburg LLP

(57) ABSTRACT

Bone anchor assemblies are disclosed herein that can provide for improved fixation as compared with traditional bone anchor assemblies. An exemplary assembly can include a bracket or wing that extends down from the receiver member. The distal portion of the wing can define a bone anchor opening through which one or more auxiliary bone anchors can be disposed to augment the fixation of the assembly's primary bone anchor. A distal surface of the distal portion of the wing can be obliquely angled relative to a proximal-
(Continued)

distal axis of the spanning portion to face one of a caudal direction or a cephalad direction. A distal surface of the distal portion of the wing can be obliquely angled relative to the proximal-distal axis of the spanning portion to face one of a medial direction or a lateral direction. Surgical methods using the bone anchor assemblies described herein are also disclosed.

13 Claims, 25 Drawing Sheets

(52) U.S. Cl.
CPC ....... *A61B 17/7002* (2013.01); *A61B 17/7035* (2013.01); *A61B 17/7041* (2013.01); *A61B 17/7043* (2013.01); *A61B 17/7055* (2013.01); *A61B 17/7067* (2013.01); *A61B 2017/564* (2013.01)

(56) References Cited

U.S. PATENT DOCUMENTS

| | | |
|---|---|---|
| 5,147,360 A | 9/1992 | Dubousset |
| 5,470,333 A | 11/1995 | Ray |
| 5,582,612 A | 12/1996 | Lin |
| 5,735,852 A | 4/1998 | Amrein et al. |
| 5,928,233 A * | 7/1999 | Apfelbaum ........ A61B 17/7044 606/264 |
| 6,010,503 A | 1/2000 | Richelsoph et al. |
| 6,524,315 B1 | 2/2003 | Selvitelli et al. |
| 6,565,569 B1 | 5/2003 | Assaker et al. |
| 6,585,738 B1 | 7/2003 | Mangione et al. |
| 6,682,530 B2 | 1/2004 | Dixon et al. |
| 6,736,820 B2 | 5/2004 | Biedermann et al. |
| 6,974,460 B2 | 12/2005 | Carbone et al. |
| 7,179,261 B2 | 2/2007 | Sicvol et al. |
| 7,232,441 B2 | 6/2007 | Altarac et al. |
| 7,608,096 B2 | 10/2009 | Foley et al. |
| 7,618,443 B2 | 11/2009 | Abdou |
| 7,637,928 B2 | 12/2009 | Fernandez |
| 7,645,294 B2 | 1/2010 | Kalfas et al. |
| 7,695,500 B2 | 4/2010 | Markworth |
| 7,699,876 B2 | 4/2010 | Barry et al. |
| 7,892,260 B2 | 2/2011 | Mahoney et al. |
| 7,985,223 B2 | 7/2011 | Khodadadyan-Klostermann et al. |
| 8,012,184 B2 | 9/2011 | Schläpfer et al. |
| 8,025,681 B2 | 9/2011 | Colleran et al. |
| 8,167,917 B2 | 5/2012 | Chin et al. |
| 8,231,655 B2 | 7/2012 | Stinson et al. |
| 8,298,269 B2 | 10/2012 | Null et al. |
| 8,303,631 B2 | 11/2012 | Duggal et al. |
| 8,343,196 B2 | 1/2013 | Schneider |
| 8,353,937 B2 | 1/2013 | Capote et al. |
| 8,454,658 B2 | 6/2013 | Lindner |
| 8,496,686 B2 | 7/2013 | Berg et al. |
| 8,506,567 B2 | 8/2013 | Ziemek et al. |
| 8,551,144 B2 | 10/2013 | Youssef et al. |
| 8,568,459 B2 | 10/2013 | Uribe et al. |
| 8,574,268 B2 | 11/2013 | Chan et al. |
| 8,591,513 B2 | 11/2013 | Overes et al. |
| 8,758,346 B2 | 6/2014 | Koay et al. |
| 8,845,697 B2 | 9/2014 | Montello et al. |
| 8,845,698 B2 | 9/2014 | Schneider |
| 8,852,245 B2 | 10/2014 | Schneider |
| 8,876,872 B2 | 11/2014 | Ziolo et al. |
| 8,876,873 B2 | 11/2014 | Schneider |
| 8,894,695 B2 | 11/2014 | Moore et al. |
| 8,979,903 B2 | 3/2015 | Capote et al. |
| 9,060,815 B1 | 6/2015 | Gustine et al. |
| 9,962,192 B2 | 5/2018 | Hawkins et al. |
| 10,238,432 B2 | 3/2019 | Carruth et al. |
| 10,568,674 B1 | 2/2020 | Eichenseer |
| 10,779,861 B2 | 9/2020 | Hawkins et al. |
| 10,898,232 B2 | 1/2021 | Lee et al. |
| 11,154,332 B2 | 10/2021 | Hawkins et al. |
| 11,304,728 B2 | 4/2022 | Lee et al. |
| 11,426,210 B2 | 8/2022 | Lee et al. |
| 2001/0020169 A1 | 9/2001 | Metz-Stavenhagen |
| 2001/0047174 A1 | 11/2001 | Donno et al. |
| 2002/0049446 A1 | 4/2002 | Harkey et al. |
| 2004/0210218 A1 | 10/2004 | Dixon et al. |
| 2005/0216004 A1 | 9/2005 | Schwab |
| 2005/0261688 A1 | 11/2005 | Grady et al. |
| 2006/0064091 A1 | 3/2006 | Ludwig et al. |
| 2006/0195089 A1 | 8/2006 | LeHuec et al. |
| 2008/0140130 A1* | 6/2008 | Chan ................. A61B 17/1782 606/301 |
| 2008/0161858 A1 | 7/2008 | Mahoney et al. |
| 2008/0183217 A1 | 7/2008 | Glaser |
| 2008/0234733 A1 | 9/2008 | Scrantz et al. |
| 2009/0036930 A1 | 2/2009 | Allison |
| 2009/0125067 A1 | 5/2009 | Mazzuca et al. |
| 2009/0248077 A1 | 10/2009 | Johns |
| 2010/0036420 A1 | 2/2010 | Kalfas et al. |
| 2010/0076496 A1 | 3/2010 | Fernandez |
| 2010/0094358 A1 | 4/2010 | Moore et al. |
| 2010/0114174 A1 | 5/2010 | Jones et al. |
| 2010/0292735 A1* | 11/2010 | Schlaepfer ........... A61B 17/808 606/86 A |
| 2010/0305616 A1 | 12/2010 | Carbone |
| 2011/0184470 A1 | 7/2011 | Gorek et al. |
| 2011/0230920 A1 | 9/2011 | Gorek et al. |
| 2011/0288599 A1 | 11/2011 | Michielli et al. |
| 2012/0010658 A1 | 1/2012 | Kirschman |
| 2012/0226316 A1 | 9/2012 | Dant et al. |
| 2013/0046352 A1 | 2/2013 | McClintock |
| 2013/0053901 A1 | 2/2013 | Cormier et al. |
| 2013/0060283 A1 | 3/2013 | Suh et al. |
| 2013/0085534 A1* | 4/2013 | Hainard ............. A61B 17/7044 606/278 |
| 2013/0090688 A1 | 4/2013 | Montello et al. |
| 2013/0096618 A1 | 4/2013 | Chandanson et al. |
| 2013/0110163 A1 | 5/2013 | Ballard et al. |
| 2013/0261679 A1 | 10/2013 | McBride et al. |
| 2014/0018858 A1 | 1/2014 | Laeng et al. |
| 2014/0052183 A1 | 2/2014 | Freese |
| 2014/0081269 A1 | 3/2014 | Biedermann |
| 2014/0107783 A1 | 4/2014 | Abdou |
| 2014/0180345 A1 | 6/2014 | Chan et al. |
| 2014/0188223 A1 | 7/2014 | Jensen et al. |
| 2014/0249581 A1 | 9/2014 | Stachniak |
| 2014/0257395 A1 | 9/2014 | Ledet et al. |
| 2015/0012042 A1 | 1/2015 | Black |
| 2015/0018889 A1 | 1/2015 | Schneider |
| 2015/0119940 A1 | 4/2015 | Jackson et al. |
| 2016/0000473 A1 | 1/2016 | Ludwig et al. |
| 2016/0022341 A1 | 1/2016 | Agarwal |
| 2016/0106477 A1 | 4/2016 | Hynes et al. |
| 2016/0106479 A1 | 4/2016 | Hynes et al. |
| 2016/0128732 A1 | 5/2016 | Strnad et al. |
| 2017/0265901 A1 | 9/2017 | Hawkins et al. |
| 2017/0348026 A1* | 12/2017 | Stein ................... A61B 17/705 |
| 2018/0214185 A1 | 8/2018 | Hawkins et al. |
| 2019/0038323 A1 | 2/2019 | Minfelde et al. |
| 2019/0183541 A1 | 6/2019 | Lee et al. |
| 2019/0254719 A1 | 8/2019 | Gandhi et al. |
| 2019/0290331 A1 | 9/2019 | Lee et al. |
| 2020/0030007 A1 | 1/2020 | Hawkins et al. |
| 2020/0229847 A1 | 7/2020 | Capote et al. |
| 2021/0085375 A1 | 3/2021 | Lee et al. |
| 2021/0251662 A1 | 8/2021 | Lee et al. |
| 2022/0015806 A1 | 1/2022 | Hawkins et al. |
| 2022/0296279 A1 | 9/2022 | Lee et al. |

FOREIGN PATENT DOCUMENTS

| | | |
|---|---|---|
| EP | 3 429 494 A2 | 1/2019 |
| FR | 2 951 064 A1 | 4/2011 |
| GB | 2483531 A | 3/2012 |
| JP | H04215750 A | 8/1992 |
| JP | 2001252283 A | 9/2001 |
| JP | 2002512840 A | 5/2002 |
| JP | 2002519135 A | 7/2002 |

(56) References Cited

FOREIGN PATENT DOCUMENTS

| | | |
|---|---|---|
| JP | 2010533547 A | 10/2010 |
| JP | 2011502641 A | 1/2011 |
| WO | 2015/142320 A1 | 9/2015 |

OTHER PUBLICATIONS

U.S. Appl. No. 15/926,069, filed Mar. 20, 2018, Multipoint Fixation Implants and Related Methods.
U.S. Appl. No. 15/940,757, filed Mar. 29, 2018, Multipoint Fixation Implants.
U.S. Appl. No. 16/581,714, filed Sep. 24, 2019, Multipoint Fixation Implants.
U.S. Appl. No. 16/583,233, filed Sep. 25, 2019, Multipoint Angled Fixation Impants for Multiple Screws and Related Methods.
U.S. Appl. No. 17/174,456, filed Feb. 12, 2021, Integrated Multipoint Fixation Screw.
International Search Report and Written Opinion for Application No. PCT/US2017/022860, dated Sep. 21, 2017 (20 pages).
International Search Report and Written Opinion for Application No. PCT/IB2019/052191, dated Jul. 8, 2019 (15 pages).
International Search Report and Written Opinion for Application No. PCT/IB2020/058939, dated Feb. 5, 2021 (14 pages).
U.S. Appl. No. 17/489,774, filed Sep. 29, 2021, Multipoint Fixation Implants.
U.S. Appl. No. 17/694,645, filed Mar. 14, 2022, Integrated Multipoint Fixation Screw.
International Search Report and Written Opinion for Application No. PCT/EP2021/052709, dated Jun. 1, 2021.
Chinese Search Report for Application No. 201780030579, dated Feb. 5, 2021.
Search Report for Japanese Application No. 2020-550794 dated Jan. 23, 2023 (30 pages).
Japanese Notice of Reasons for Refusal issued for Application No. 2020-550794, dated Feb. 21, 2023 (46 pages).
Search Report for Japanese Application No. 2018-548909 dated Jan. 28, 2021 (33 pages).
Japanese Notice of Reasons for Refusal for Application No. 2018-548909, dated Feb. 9, 2021 (6 pages).
Japanese Decision to Grant a Patent for Application No. 2018-548909 dated Jun. 24, 2021.

\* cited by examiner

MULTIPOINT FIXATION IMPLANTS AND RELATED METHODS

CROSS-REFERENCE TO RELATED APPLICATIONS

This application is a continuation of U.S. application Ser. No. 15/926,069, filed Mar. 20, 2018, which is incorporated herein by reference in its entirety.

FIELD

Orthopedic implants and related methods are disclosed herein. For example, bone anchor assemblies with multiple bone engagement points are disclosed.

BACKGROUND

Bone anchor assemblies can be used in orthopedic surgery to fix bone during healing, fusion, or other processes. In spinal surgery, for example, bone anchor assemblies can be used to secure a spinal fixation element to one or more vertebrae to rigidly or dynamically stabilize the spine. Bone anchor assemblies can also be used as an engagement point for manipulating bone (e.g., distracting, compressing, or rotating one vertebra with respect to another vertebra, reducing fractures in a long bone, and so forth).

The integrity with which the bone anchor assembly engages the bone can affect the transfer of corrective biomechanical forces. While a great amount of care is exercised when placing bone anchor assemblies, it is common that a bone anchor assembly will be inserted in a compromised state. For example, the bone opening in which the assembly is disposed can be stripped (e.g., by driving the bone anchor assembly past its optimum holding position), the bone anchor assembly can be placed incorrectly (e.g., using an incorrect instrument maneuver such as an over-sized pilot hole), the bone anchor assembly can be placed outside of its intended trajectory (e.g., within a facet capsule or breached through a pedicle wall), or the bone anchor assembly can be inserted into compromised bone (e.g., bone that is fractured, osteoporotic, diseased, or otherwise lacking in structural integrity).

When the bone anchor assembly is in a compromised state, there can be sub-optimal purchase between the bone anchor assembly and the bone. The bone anchor assembly may feel unsecure to the surgeon, and it is possible that the bone anchor assembly could back out or become loosened over time. There are limited options for the surgeon when faced with these types of situations. In spinal surgery, for example, the surgeon can remove the bone anchor assembly and skip the vertebral level, though this can undesirably require expanding the surgical site to additional vertebral levels. The surgeon can remove and re-insert with a larger anchor, though this may not be an option when space for anchoring in the bone is limited. The surgeon can leave the compromised bone anchor assembly in place, which may be the safest alternative if the bone anchor assembly is in a safe location and attachment to the plate, rod, or other implant construct is definitive, as the additional compromised fixation may be better than removal.

Even when a bone anchor assembly is placed in a non-compromised state, the geometry of traditional bone anchor assemblies can limit the flexibility with which the bone attachment point can be located with respect to a plate, rod, or other implant construct coupled to the bone anchor assembly.

There is a continual need for improved bone anchor assemblies and related methods.

SUMMARY

Bone anchor assemblies are disclosed herein that can provide for improved fixation as compared with traditional bone anchor assemblies. An exemplary assembly can include a bracket or wing that extends down from the receiver member and accommodates one or more auxiliary bone anchors that augment the fixation of the assembly's primary bone anchor. Another exemplary assembly can include a plate that is seated between the receiver member and the rod and accommodates one or more auxiliary bone anchors that augment the fixation of the assembly's primary bone anchor. Another exemplary assembly can include a hook that extends out from the receiver member to hook onto an anatomical structure or another implant to augment the fixation of the assembly's primary bone anchor. Surgical methods using the bone anchor assemblies described herein are also disclosed.

In some embodiments, a bone anchor assembly includes a bone anchor; a receiver member coupled to a proximal end of the bone anchor and defining a recess configured to receive a rod; a closure mechanism threadably mated to the receiver member; a wing having a proximal portion disposed proximal to the receiver member, a distal portion that defines a bone anchor opening, and a spanning portion that connects the proximal and distal portions; and a nut configured to threadably engage the closure mechanism to secure the proximal portion of the wing to the proximal end of the receiver member.

The closure mechanism can be or can include a threaded post. The wing can include an opening through which at least a portion of the threaded post is disposed. The wing can be rotatable about the closure mechanism. A distal-facing surface of the proximal portion of the wing can bear against a proximal terminal end of the receiver member. A lateral surface of the distal portion of the wing can form a negative of a sidewall of the receiver member. A lateral surface of the spanning portion of the wing can form a negative of a sidewall of the receiver member. A lateral surface of the spanning portion of the wing can include a protrusion that engages a corresponding recess formed in the receiver member. The spanning portion can hug the sidewall of the receiver member. The receiver member can be polyaxially movable relative to the bone anchor. The assembly can include an auxiliary bone anchor disposed in the bone anchor opening of the distal portion of the wing. The proximal-most extent of the auxiliary bone anchor can be distal to a rod when the rod is disposed in the recess of the receiver member. The proximal-most extent of the auxiliary bone anchor can be distal to the distal-most extent of the receiver member. The spanning portion can have an adjustable height. The spanning portion can include first and second legs movable toward one another to increase the height of the spanning portion and movable away from one another to decrease the height of the spanning portion. The spanning portion can be deformable to allow the distal portion of the wing to be angled to match an abutting bone surface.

In some embodiments, a method of securing a bone anchor assembly to bone includes driving a bone anchor into bone, the bone anchor having a receiver member coupled to a proximal end thereof; positioning a rod in the receiver member; attaching a closure mechanism to the receiver member to retain the rod in the receiver member; coupling a proximal portion of a wing to at least one of the closure mechanism and a proximal surface of the receiver member; and inserting an auxiliary bone anchor through a bone anchor opening formed in a distal portion of the wing and driving the auxiliary bone anchor into the bone.

Coupling the proximal portion of the wing can include inserting at least a portion of the closure mechanism through an opening formed in the proximal portion of the wing. The method can include rotating the wing relative to receiver member to position the bone anchor opening of the wing with respect to a target location on the bone. The method can include deforming the wing to position the bone anchor opening of the wing with respect to a target location on the bone. The method can include adjusting a height of the wing such that the wing spans from the proximal-most extent of the receiver member to the bone. The bone anchor and the auxiliary bone anchor can be driven into a single vertebra.

In some embodiments, a bone anchor assembly includes a bone anchor; a receiver member coupled to a proximal end of the bone anchor and defining a recess configured to receive a rod; a closure mechanism threadably mated to the receiver member; a plate having a primary opening through which first and second arms of the receiver member extend, a bone anchor opening, and a saddle portion that extends across at least a portion of the primary opening such that the saddle portion is disposed in the recess of the receiver member; and an auxiliary bone anchor disposed through the bone anchor opening of the plate.

The assembly can include a rod disposed between the saddle portion of the plate and the closure mechanism. The saddle portion can be movably coupled to the plate. A distal facing surface of the saddle portion can form a section of a cylinder. The primary opening in the plate can be defined by a first sidewall. The bone anchor opening of the plate can be defined by a second sidewall. A height of the first sidewall can be reduced where the first sidewall meets the second sidewall. The assembly can include a cap configured to engage the first and second arms of the receiver member. The cap can define a central opening disposed proximal to a proximal-most extent of the receiver member. The central opening can receive at least a portion of the closure mechanism therethrough. The proximal-most extent of the auxiliary bone anchor can be distal to a rod when the rod is disposed in the recess of the receiver member. The proximal-most extent of the auxiliary bone anchor can be distal to the distal-most extent of the receiver member.

In some embodiments, a method of securing a bone anchor assembly to bone includes driving a bone anchor into bone, the bone anchor having a receiver member coupled to a proximal end thereof; inserting first and second arms of the receiver member through a primary opening of a plate such that a saddle portion of the plate is disposed in a rod-receiving recess of the receiver member; positioning a rod on a proximal-facing surface of the saddle portion such that the rod is disposed in the rod-receiving recess of the receiver member; attaching a closure mechanism to the receiver member to retain the rod in the receiver member; and inserting an auxiliary bone anchor through a bone anchor opening formed in the plate and driving the auxiliary bone anchor into the bone.

The method can include bending the plate to position the bone anchor opening against the bone. The method can include bending the saddle portion of the plate to position the bone anchor opening against the bone. The bone anchor and the auxiliary bone anchor can be driven into a single vertebra.

In some embodiments, a bone anchor assembly includes a bone anchor; a receiver member coupled to a proximal end of the bone anchor and defining a recess configured to receive a rod; a closure mechanism threadably mated to the receiver member; a plate having a primary opening through which at least a portion of the receiver member extends, a bone anchor opening, and a distal-facing portion that extends across a proximal-facing portion of the receiver member; and an auxiliary bone anchor disposed through the bone anchor opening of the plate.

In some embodiments, a bone anchor assembly includes a bone anchor; a receiver member coupled to a proximal end of the bone anchor and defining a recess configured to receive a rod; a closure mechanism threadably mated to the receiver member; and a hook having a body portion coupled to the receiver member and a curved extension projecting from the body portion.

The extension can be substantially U-shaped. The extension can define an inside curved surface and an outside curved surface. The inside curved surface can form a substantial negative of a lamina. The body portion can have a lateral sidewall that abuts a sidewall of the receiver member. The hook can be coupled to the receiver member by a collar. The collar can define a first opening in which the receiver member is disposed and a second opening through which a locking screw is disposed. The locking screw can threadably engage the body portion of the hook. The first opening can include an engagement feature that engages a corresponding engagement feature formed in or on an exterior of the receiver member. The second opening can have a tapered shape to pull the receiver member towards the body portion as the locking screw is tightened. The collar can be disposed proximal to a rod when the rod is disposed in the receiver member. The collar can extend around an outer periphery of the receiver member. The hook can be configured to pivot with the receiver member relative to the bone anchor. The hook can be coupled to the receiver member by a nut. The nut can be threaded onto the closure mechanism to compress a proximal portion of the hook against a proximal end of the receiver member.

In some embodiments, a method of securing a bone anchor assembly to bone includes driving a bone anchor into bone, the bone anchor having a receiver member coupled to a proximal end thereof; positioning a rod within a rod-receiving recess of the receiver member; attaching a hook to the receiver member and hooking an extension of the hook onto at least one of an anatomical structure and an implant; and attaching a closure mechanism to the receiver member to retain the rod in the receiver member.

The bone anchor can be driven into a first vertebra and the extension of the hook can be hooked onto a lamina of the first vertebra. The hook can be attached to the receiver member after the bone anchor is driven into the bone. The closure mechanism can be attached to the receiver member after the hook is attached to the receiver member. The hook can be attached to the receiver member after the rod is seated in the receiver member.

In some embodiments, a bone anchor assembly can include a bone anchor; an auxiliary bone anchor; a receiver member coupled to a proximal end of the bone anchor and defining a rod seat configured to receive a rod; a closure mechanism threadably mated to the receiver member; a wing that includes a proximal portion, a distal portion, and a spanning portion that connects the proximal and distal portions, the proximal portion having a distal-facing surface that opposes a proximal terminal end of the receiver member and defines an opening through which at least a portion of the closure mechanism is disposed, the spanning portion extending vertically along a side wall of the receiver member between the proximal portion and the distal portion, the distal portion extending outward from a distal end of the spanning portion; and a nut configured to threadably engage the closure mechanism to secure the proximal portion of the wing to the receiver member. The distal portion of the wing can define a bone anchor opening through which the auxiliary bone anchor can be disposed. The distal surface of the distal portion of the wing can be obliquely angled relative to a proximal-distal axis of the spanning portion to face one of a caudal direction or a cephalad direction.

The distal surface of the distal portion of the wing can be obliquely angled to the right of the proximal-distal axis of the spanning portion. The distal surface of the distal portion of the wing can be obliquely angled to the left of the proximal-distal axis of the spanning portion. The distal surface of the distal portion of the wing can be obliquely angled relative to a proximal-distal axis of the spanning portion such that a central axis of the bone anchor opening extends in one of a caudal direction or a cephalad direction and in one of a medial direction or a lateral direction when the wing is secured to the receiver member.

The distal surface of the distal portion of the wing can be obliquely angled inward and to the right of the proximal-distal axis of the spanning portion. The distal surface of the distal portion of the wing can be obliquely angled outward and to the right of the proximal-distal axis of the spanning portion. The distal surface of the distal portion of the wing can be obliquely angled inward and to the left of the proximal-distal axis of the spanning portion. The distal surface of the distal portion of the wing can be obliquely angled outward and to the left of the proximal-distal axis of the spanning portion. A proximal surface of the distal portion of the wing can be substantially parallel to the distal surface of the distal portion.

In some embodiments, a bone anchor assembly can include a bone anchor; an auxiliary bone anchor; a receiver member coupled to a proximal end of the bone anchor and defining a rod seat configured to receive a rod; a closure mechanism threadably mated to the receiver member; a wing that includes a proximal portion, a distal portion, and a spanning portion that connects the proximal and distal portions, the proximal portion having a distal-facing surface that opposes a proximal terminal end of the receiver member and defines an opening through which at least a portion of the closure mechanism is disposed, the spanning portion extending vertically along a side wall of the receiver member between the proximal portion and the distal portion, the distal portion extending outward from a distal end of the spanning portion; and a nut configured to threadably engage the closure mechanism to secure the proximal portion of the wing to the receiver member. The distal portion of the wing can define a bone anchor opening through which the auxiliary bone anchor can be disposed. A distal surface of the distal portion of the wing can be obliquely angled relative to a proximal-distal axis of the spanning portion to face one of a medial direction or a lateral direction.

The distal surface of the distal portion of the wing can be obliquely angled inward towards the proximal-distal axis of the spanning portion. The distal surface of the distal portion of the wing can be obliquely angled outward away from the proximal-distal axis of the spanning portion. A proximal surface of the distal portion of the wing can be substantially parallel to the distal surface of the distal portion.

In any of the foregoing embodiments, the auxiliary bone anchor can have a threaded proximal head. The bone anchor opening can have a partially threaded interior surface configured to engage the threaded proximal head of the auxiliary bone anchor such that the auxiliary bone anchor can be capable of being locked at any angle amongst multiple selectable angles relative to the central axis of the bone anchor opening. The closure mechanism can include a threaded post having a radially extending shoulder portion. A counter bore can be formed about the opening in the distal-facing surface of the proximal portion of the wing to accommodate the radially extending shoulder portion extending at least partially above the proximal terminal end of the receiver member. The bone anchor opening defined in the distal portion of the wing can include multiple bone anchor openings. A central axis of the bone anchor opening can be substantially perpendicular to the distal surface of the distal portion such that the central axis of the bone anchor opening extends in the medial direction or the lateral direction. The wing can include a unilateral locking interface configured to enable a surgical instrument to hold onto one side of the wing.

In some embodiments, a method of securing a bone anchor assembly to bone can include driving a bone anchor into bone, the bone anchor having a receiver member coupled to a proximal end thereof; positioning a rod in a rod seat defined in the receiver member; attaching a closure mechanism to the receiver member to retain the rod in the receiver member; coupling a proximal portion of a wing to at least one of the closure mechanism and a proximal terminal end of the receiver member, such that a spanning portion of the wing extends vertically along a side wall of the receiver member between the proximal portion and a distal portion of the wing that extends outward from a distal end of the spanning portion; and driving the auxiliary bone anchor through a bone anchor opening formed in the distal portion of the wing into bone at an oblique angle in one of a caudal direction or a cephalad direction. A distal surface of the distal portion of the wing can be obliquely angled relative to a proximal-distal axis of the spanning portion to face the caudal direction or the cephalad direction.

Driving the auxiliary bone anchor through the bone anchor opening into bone can include driving the auxiliary bone anchor through the bone anchor opening at an oblique angle in a cephalad direction such that the bone anchor and the auxiliary bone anchor can be respectively driven into a same vertebral level. Driving the auxiliary bone anchor through the bone anchor opening into bone can include driving the auxiliary bone anchor through the bone anchor opening at an oblique angle in a caudal direction such that the bone anchor and the auxiliary bone anchor can be respectively driven into adjacent vertebral levels.

In some embodiments, a method of securing a bone anchor assembly to bone can include driving a bone anchor into bone, the bone anchor having a receiver member coupled to a proximal end thereof; positioning a rod in a rod seat defined in the receiver member; attaching a closure mechanism to the receiver member to retain the rod in the receiver member; coupling a proximal portion of a wing to at least one of the closure mechanism and a proximal terminal end of the receiver member, such that a spanning portion of the wing extends vertically along a side wall of the receiver member between the proximal portion and a distal portion of the wing that extends outward from a distal end of the spanning portion; and driving the auxiliary bone anchor through a bone anchor opening formed in the distal portion of the wing into bone at an oblique angle in one of a medial direction or a lateral direction. A distal surface of the distal portion of the wing can be obliquely angled relative to a proximal-distal axis of the spanning portion to face the medial direction or the lateral direction.

Driving the auxiliary bone anchor through the bone anchor opening into bone can include driving the auxiliary bone anchor through the bone anchor opening at an oblique angle in the medial direction such that the bone anchor and the auxiliary bone anchor can be respectively driven into a same vertebral level. Driving the auxiliary bone anchor through the bone anchor opening into bone can include driving the auxiliary bone anchor through the bone anchor opening at an oblique angle in the lateral direction such that the bone anchor and the auxiliary bone anchor can be respectively driven into a same vertebral level.

In any of the foregoing embodiment methods, the closure mechanism can include a threaded post having a radially extending shoulder portion. Coupling the proximal portion of the wing to at least one of the closure mechanism and the proximal terminal end of the receiver member can include disposing at least a portion of the threaded post through the opening formed in the proximal portion of the wing; and receiving the radially extending shoulder portion that extends at least partially above the proximal terminal end of the receiver member in a counter bore formed about the opening in the distal-facing surface of the proximal portion of the wing.

DETAILED DESCRIPTION

Bone anchor assemblies are disclosed herein that can provide for improved fixation as compared with traditional bone anchor assemblies. An exemplary assembly can include a bracket or wing that extends down from the receiver member and accommodates one or more auxiliary bone anchors that augment the fixation of the assembly's primary bone anchor. Another exemplary assembly can include a plate that is seated between the receiver member and the rod and accommodates one or more auxiliary bone anchors that augment the fixation of the assembly's primary bone anchor. Another exemplary assembly can include a hook that extends out from the receiver member to hook onto an anatomical structure or another implant to augment the fixation of the assembly's primary bone anchor. Surgical methods using the bone anchor assemblies described herein are also disclosed.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

Prior Art Bone Anchor Assembly

Figure 1A:
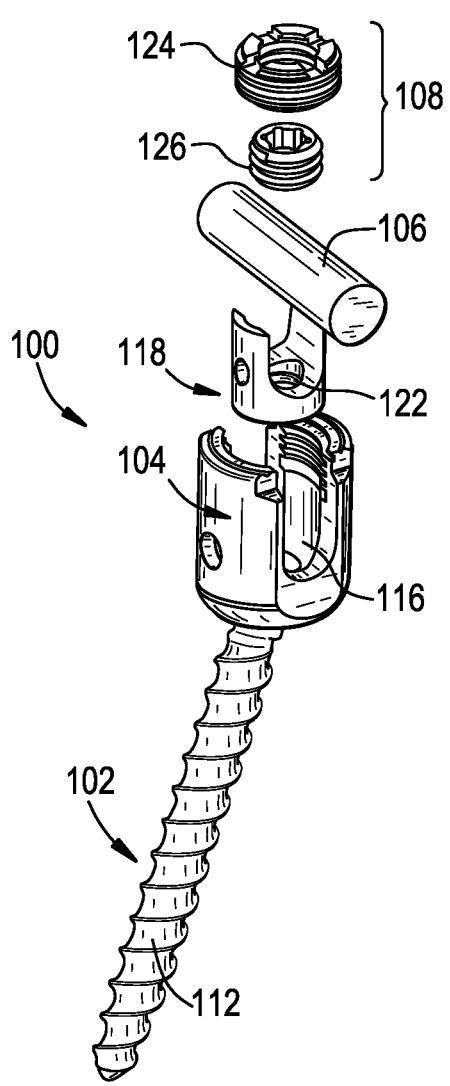
FIG. 1A is an exploded perspective view of a prior art bone anchor assembly.
Figure 1B:
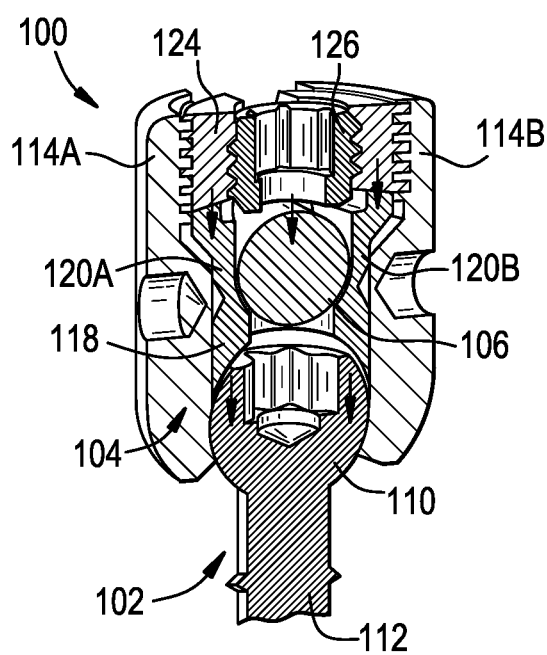
FIG. 1B is a sectional view of the bone anchor assembly of FIG. 1A.
Figure 1C:
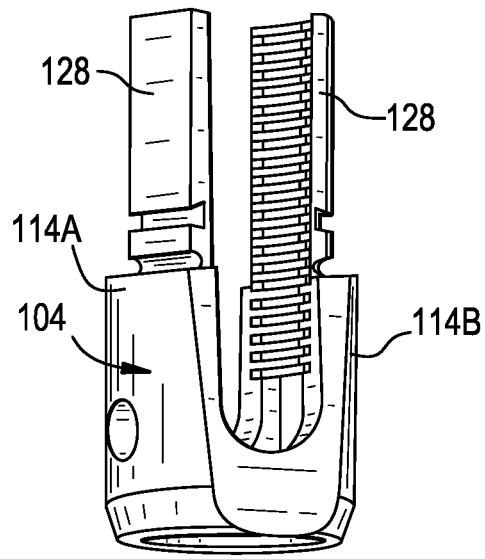
FIG. 1C is a perspective view of the bone anchor assembly of FIG. 1A shown with extension tabs.

FIGS. 1A-1C illustrate a prior art bone anchor assembly 100 with various features that can be included in the bone anchor assemblies 200, 300, 400, and 500 described below. It will be appreciated that the illustrated bone anchor assembly 100 is exemplary and that the bone anchor assemblies 200, 300, 400, and 500 can include additional or alternative features.

The illustrated bone anchor assembly 100 includes a bone anchor 102, a receiver member 104 for receiving a spinal fixation element, such as a spinal rod 106, to be coupled to the bone anchor 102, and a closure mechanism 108 to capture a spinal fixation element within the receiver member and fix the spinal fixation element with respect to the receiver member. The bone anchor 102 includes a proximal head 110 and a distal shaft 112 configured to engage bone. The receiver member 104 has a proximal end having a pair of spaced apart arms 114A, 114B defining a recess 116 therebetween and a distal end having a distal end surface defining an opening through which at least a portion of the bone anchor 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the bone anchor 102 is generally in the shape of a truncated sphere having a planar proximal surface and an approximately spherically-shaped distal surface. The illustrated bone anchor assembly 100 is a polyaxial bone screw designed for posterior implantation in the pedicle or lateral mass of a vertebra. The proximal head 110 of the bone anchor 102 engages the distal end of the receiver member 104 in a ball and socket like arrangement in which the proximal head and the distal shaft 112 can pivot relative to the receiver member. The distal surface of the proximal head 110 of the bone anchor 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the bone anchor 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the bone anchor 102 can be cannulated, having a central passage or cannula extending the length of the bone anchor to facilitate delivery of the bone anchor over a guidewire in, for example, minimally-invasive procedures. Other components of the bone anchor assembly 100, including, for example, the closure mechanism 108, the receiver member 104, and the compression member or cap 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the bone anchor 102. The sidewall openings can extend radially from the cannula through the sidewall of the distal shaft 112. Exemplary systems for delivering bone cement to the bone anchor assembly 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the bone anchor 102 can also be coated with materials to permit bone growth, such as, for example, hydroxyapatite, and the bone anchor assembly 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the bone anchor 102 extends. For example, the distal shaft 112 of the bone anchor 102 can extend through the opening.

The bone anchor 102 can be selectively fixed relative to the receiver member 104. Prior to fixation, the bone anchor 102 is movable relative to the receiver member 104 within a cone of angulation generally defined by the geometry of the distal end of the receiver member and the proximal head 110 of the bone anchor 102. The bone anchor assembly 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly 100 can be a conventional (non-biased) polyaxial screw in which the bone anchor 102 pivots in the same amount in every direction.

The spinal fixation element, e.g., the spinal rod 106, can either directly contact the proximal head 110 of the bone anchor 102 or can contact an intermediate element, e.g., a compression member 118. The compression member 118 can be positioned within the receiver member 104 and interposed between the spinal rod 106 and the proximal head 110 of the bone anchor 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the bone anchor 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the bone anchor 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. The receiver member 104 can include, can be formed integrally with, or can be coupled to one or more extension tabs 128 (shown in FIG. 1C) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor assembly 100 can be used with a spinal fixation element such as rigid spinal rod 106. Alternatively, the spinal fixation element can be a dynamic stabilization member that allows controlled mobility between the instrumented vertebrae.

In use, the bone anchor assembly 100 can be assembled such that the distal shaft 112 extends through the opening in the distal end of the receiver member 104 and the proximal head 110 of the bone anchor 102 is received in the distal end of the receiver member 104. A driver instrument can be fitted with the bone anchor 102 to drive the bone anchor into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the bone anchor 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the bone anchor 102, thereby locking the angular position of the bone anchor 102 relative to the receiver member 104. A torsional force can be applied to the inner set screw 126 to force the spinal rod 106 into engagement with the compression member 118 and thereby fix the spinal rod 106 relative to the receiver member 104.

The bone anchor assemblies 200, 300, 400, and 500 described below can be configured to operate in conjunction with, or can include any of the features of, bone anchor assemblies of the type described above or other types known in the art. Exemplary bone anchor assemblies include monoaxial screws, polyaxial screws, uniplanar screws, favored-angle screws, and/or any of a variety of other bone anchor types known in the art. Further information on favored-angle screws can be found in U.S. Patent Application Publication No. 2013/0096618, filed on Oct. 9, 2012, which is hereby incorporated by reference herein.

Multipoint Fixation Implants

FIGS. 2A-2M illustrate an exemplary embodiment of a bone anchor assembly 200, shown with a spinal rod 206. As noted above, a bone anchor can sometimes be inserted in a compromised state. This can be undesirable, especially in the cervical region of the spine where there is limited bone area in which to install additional bone anchors. The illustrated bone anchor assembly 200 can allow for supplemental fixation of a primary bone anchor in a compact footprint, without necessarily requiring removal or re-insertion of the primary bone anchor. As shown, the bone anchor assembly 200 can include a bone anchor 202, a receiver member 204, a closure mechanism 208, a bracket or wing 230, a nut 232, and one or more auxiliary bone anchors 234. In use, the wing 230 can be secured to the receiver member 204, e.g., using the closure mechanism 208 and nut 232, thereby providing the ability to augment fixation of the bone anchor 202 with the one or more auxiliary bone anchors 234.

Except as described below or as will be readily appreciated by one having ordinary skill in the art, the bone anchor 202 and receiver member 204 are substantially similar to the bone anchor 102 and receiver member 104 described above. A detailed description of the structure and function thereof is thus omitted here for the sake of brevity. The bone anchor assembly 200 can include any one or more of the features of the bone anchor assembly 100 described above.

The closure mechanism 208 can be selectively secured to the receiver member 204 to capture a spinal fixation element, e.g., a spinal rod 206, within the receiver member. Tightening or locking the closure mechanism 208 can be effective to fix the spinal rod 206 relative to the receiver member 204, and to fix an angular position of the bone anchor 202 relative to the receiver member 204. The illustrated closure mechanism 208 is in the form of a threaded post with an enlarged-diameter distal portion 208d and a reduced-diameter proximal portion 208p. In other embodiments, the proximal and distal portions 208p, 208d can have the same diameter, or the proximal portion can have a diameter greater than that of the distal portion. The distal portion 208d of the closure mechanism 208 can be threaded into the receiver member 204 to engage a spinal rod 206 disposed in the receiver member. The proximal portion 208p of the closure mechanism 208 can protrude above the receiver member 204, e.g., above a proximal-facing terminal end surface of the receiver member, and through an opening 236 formed in the wing 230, as described further below.

In the illustrated embodiment, the closure mechanism 208 bears directly against the spinal rod 206, which in turn bears directly against the head of the bone anchor 202. It will be appreciated, however, that one or more intermediate elements can also be included in the bone anchor assembly 200.

For example, the bone anchor assembly 200 can include a compression member of the type described above disposed between the spinal rod 206 and the head of the bone anchor 202. The closure mechanism 208 can be a single set screw as shown, or can include an outer set screw operable to act on a compression member and an inner set screw operable to act on the rod 206. The closure mechanism 208 can include a driving interface (e.g., torx, flathead, Phillips head, square, or otherwise) to facilitate rotational advancement or retraction of the closure mechanism relative to the receiver member 204 using a driver instrument.

The nut 232 can include a central opening 238 sized to receive at least a portion of the proximal end 208p of the closure mechanism 208 therethrough. The central opening 238 can include an internal thread that corresponds to the external thread of the closure mechanism 208, such that the nut 232 can be threaded onto the closure mechanism and tightened to secure the wing 230 to the closure mechanism and the receiver member 204 in which the closure mechanism is disposed. The outer surface of the nut 232 can be faceted or otherwise configured to facilitate application of torque to the nut. In some embodiments, the nut 232 can have a hexagonal or square cross-section.

As shown in FIGS. 2E-2H, the bracket or wing 230 can include a proximal portion 230p that can contact the receiver member 204, a distal portion 230d that can contact a bone surface or be disposed in close proximity to a bone surface, and a spanning portion 230s that connects the proximal and distal portions.

The proximal portion 230p of the wing 230 can include a central opening 236 sized to receive at least a portion of the closure mechanism 208 therethrough. For example, the central opening 236 can be sized to receive the proximal portion 208p of the closure mechanism 208 therethrough. The central opening 236 can include a smooth, non-threaded interior surface to allow the wing 230 and the closure mechanism 208 to be freely rotatable with respect to one another. A proximal-facing surface 240 of the proximal portion 230p of the wing 230 can be domed or rounded to provide an atraumatic surface and reduce the risk of tissue irritation post-implantation. A distal-facing surface 242 of the proximal portion 230p of the wing 230 can be configured to engage the proximal-facing surface of the receiver member 204. The distal-facing surface 242 can form a negative or a substantial negative of the proximal-facing surface of the receiver member 204. For example, the proximal-facing surfaces of the arms 214A, 214B of the receiver member 204 can be radially-convex, and the distal-facing surface 242 of the wing 230 can define a radially-concave channel that receives the convex ends of the arms. In some embodiments, the central opening 236 or another feature of the wing 230 can be sized and configured to snap onto or capture a portion of the closure mechanism 208 or a proximal surface of the receiver member 204.

The distal portion 230d of the wing 230 can include one or more openings 244 configured to receive a bone anchor 234 therethrough. While two bone anchor openings 244 are shown in the illustrated embodiment, it will be appreciated that the wing 230 can include any number of bone anchor openings (e.g., one, two, three, four, five, and so on). The bone anchor openings 244 can include any of a number of features for accepting bone anchors 234 at varying angles and/or increasing the security and stability with which bone anchors can be secured to the wing 230. Exemplary features that can be included are disclosed in U.S. Pat. No. 7,637,928, issued on Dec. 29, 2009; U.S. Pat. No. 8,343,196, issued on Jan. 1, 2013; U.S. Pat. No. 8,574,268, issued on Nov. 5, 2013; U.S. Pat. No. 8,845,697, issued on Sep. 30, 2014; and U.S. Pat. No. 8,758,346, issued on Jun. 24, 2014, which are each hereby incorporated by reference herein. For example, the bone anchor openings 244 can be at least partially threaded to receive a variable-angle locking screw having a threaded proximal head. As shown, the openings 244 can have a plurality of columns of threads spaced apart to define a plurality of non-threaded recesses. In the illustrated embodiment, each of the openings 244 has four columns of threads. The columns of threads can be arranged around the inner surface of each of the openings 244 for engaging threads on the heads of locking auxiliary bone anchors and/or variable-angle locking auxiliary bone anchors. The auxiliary bone anchors 234 can thus be locked with the wing 230 coaxially with the central axis of the opening 244 or at a selected angle within a range of selectable angles relative to the central axis of the opening. The auxiliary bone anchors 234 can include features to facilitate this variable-angle locking, such as a proximal head that is at least partially spherical having a thread with a profile that follows the arc-shaped radius of curvature of the spherical portion of the head. The variable-angle capability of the screw/opening interface can allow the user to place locking auxiliary bone anchors into the bone at any angle within defined angulation limits, thus providing improved placement flexibility and eliminating or reducing the need to conform the distal portion of the wing to the bone surface to achieve a desired insertion angle. The auxiliary bone anchors 234 can be driven into the bone with diverging or converging longitudinal axes (relative to each other and/or relative to the primary bone anchor 202) which can provide improved resistance to pullout. In some embodiments, the interior surfaces of the openings 244 can be smooth or spherical, without threads or locking features.

The central axis of each of the openings 244 can be perpendicular or substantially perpendicular to a distal-facing surface 246 of the wing 230. Alternatively, one or more of the openings can have a central axis that extends at an oblique angle with respect to the distal-facing surface 246. In the illustrated embodiment, the central axis of each opening 244 extends at an angle of about 7 degrees with respect to the distal-facing surface 246. In some embodiments, the central axis of each opening 244 can extend at an angle of between about 0 degrees and about 15 degrees with respect to the distal-facing surface 246 (e.g., embodiments used for bony attachment locations that allow direct proximal to distal screw insertion). In some embodiments, the central axis of each opening 244 can extend at an angle of between about 15 degrees and about 45 degrees with respect to the distal-facing surface 246 (e.g., embodiments used for bony attachment locations where an angled trajectory may avoid or target specific anatomy). Angled or divergent central axes can advantageously increase the pullout resistance of the construct.

The distal portion 230d of the wing 230 can have a distal-facing surface 246 configured to contact bone or to be disposed in close proximity to bone. The distal-facing surface 246 can include teeth, texturing, or other surface features to enhance grip with the adjacent bone. The distal portion 230d of the wing 230 can have a lateral surface 248 that abuts a sidewall of the receiver member 204. The lateral surface 248 can form a negative of the sidewall of the receiver member 204, such that the distal-portion 230d of the wing 230 can hug the receiver member with minimal or zero gap therebetween. For example, the lateral surface 248 can be concave with a radius of curvature equal or substantially equal to a radius of curvature of the exterior sidewall of the receiver member 204.

The spanning portion 230s of the wing 230 can extend vertically in a proximal-distal direction to join the proximal portion 230p of the wing to the distal portion 230d of the wing. The spanning portion 230s of the wing 230 can have a lateral surface 250 that engages a sidewall of the receiver member 204. The lateral surface 250 can form a negative of the sidewall of the receiver member 204, such that the spanning portion 230s of the wing 230 can hug the receiver member with minimal or zero gap therebetween. For example, the lateral surface 250 can be concave with a radius of curvature equal or substantially equal to a radius of curvature of the exterior sidewall of the receiver member 204. The lateral surface 250 can also include one or more protrusions 252 for engaging a corresponding recess 254 formed in the sidewall of the receiver member 204, or one or more recesses in which a protrusion of the receiver member is received. The interaction between the one or more protrusions 252 and the one or more recesses 254 can be effective to limit or prevent rotation of the wing 230 with respect to the receiver member 204. This interaction can also be effective to limit or prevent movement of the wing 230 with respect to the receiver member 204 along a proximal-distal axis. The spanning portion 230s can include webbing or ribs 256 to enhance the structural rigidity of the wing 230. The ribs 256 can be formed in an outer surface of the spanning portion 230s, opposite to the lateral surface 250 that engages the receiver member 204.

The proximal portion 230p, distal portion 230d, and spanning portion 230s can be formed integrally as a monolithic unit as shown, or one or more of said components can be separate and selectively attachable to the others. In some embodiments, a kit of modular components can be provided to allow selection of the components most appropriate for a given use. For example, a spanning portion 230s of appropriate height can be selected based on the distance between the proximal end of the receiver member 204 and the bone surface in a given application.

One or more portions of the wing 230 can be flexible or deformable to allow the wing to be custom-tailored for a particular situation.

For example, the distal portion 230d of the wing 230 can be flexible or deformable to allow the distal portion to be contoured to the bone surface. The distal portion 230d can be contoured before implantation or in situ. The distal portion 230d can be contoured using a separate bending instrument, or by tightening the bone anchors 234 to deform the distal portion into intimate contact with the bone surface. The distal portion 230d of the wing 230 can be pre-shaped or pre-contoured, e.g., during manufacture, to match a bone surface with which the bone anchor assembly 200 is to be used.

By way of further example, the spanning portion 230s of the wing 230 can be flexible or deformable to allow the position of the bone anchor openings 244 to be adjusted relative to the receiver member 204. The spanning portion 230s can be bent or flexed inwardly or outwardly (e.g., in a medial-lateral direction) to move the bone anchor openings 244 inward towards the receiver member 204 or outward away from the receiver member. Such bending can also increase or decrease the effective height of the wing 230, to accommodate varying distances that may be encountered between the proximal end of the receiver member 204 and the bone surface. The spanning portion 230s can be bent or flexed up or down (e.g., in a superior-inferior direction) to move the bone anchor openings 244 relative to the receiver member 204. The spanning portion 230s can be contoured before implantation or in situ. The spanning portion 230s can be contoured using a separate bending instrument, or by tightening the bone anchors 234 to deform the spanning portion into the desired shape. The spanning portion 230s of the wing 230 can be pre-shaped or pre-contoured, e.g., during manufacture, for a given application.

As yet another example, the proximal portion 230p of the wing 230 can be flexible or deformable, and/or the connections or locations at which the proximal portion 230p, the distal portion 230d, and the spanning portion 230s are joined can be flexible or deformable. The proximal portion 230p, distal portion 230d, and spanning portion 230s can be joined by a living hinge or other joint to allow adjustment to their relative positions.

The spanning portion 230s can have an adjustable height. For example, as shown in FIGS. 2I-2M, the spanning portion 230s can include first and second flexible or deformable legs 258. By bending the legs 258 inward towards one another, the height of the spanning portion 230s can be increased. By bending the legs 258 outward away from one another, the height of the spanning portion 230s can be decreased. Each leg 258 can include an upper portion and a lower portion joined by a flexible joint (e.g., a living hinge, pivot pin, or the like). Rounded or semi-circular surfaces can be formed at the connections between the legs 258 and the proximal and distal portions 230p, 230d of the wing 230 to reduce material stress as the legs are bent. Similarly, a rounded or semi-circular cut-out can be formed where the upper portion of each leg 258 meets the lower portion. The cut-out can reduce stress and also provide an engagement surface for gripping the legs 258 with a tool configured to apply a squeezing force thereto.

Figure 2A:
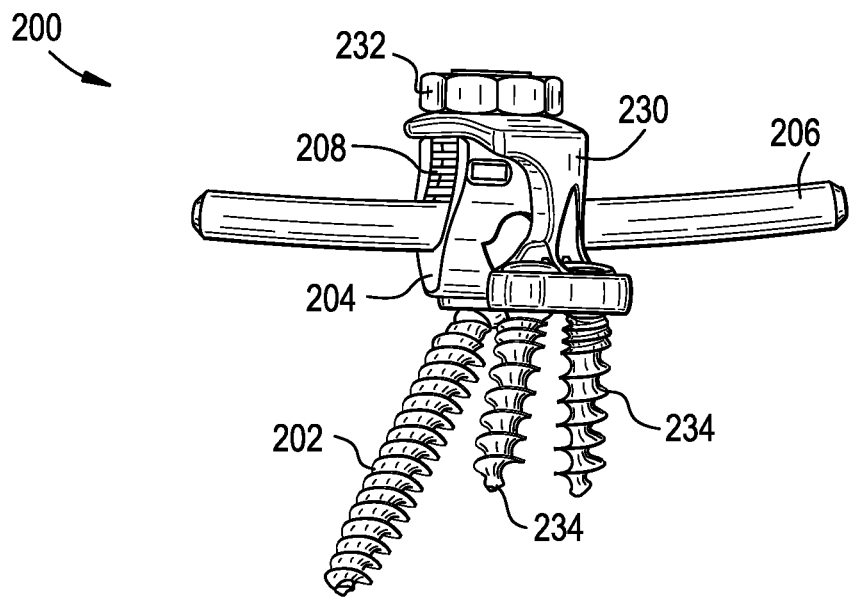
FIG. 2A is a perspective view of a bone anchor assembly and a spinal rod.
Figure 2B:
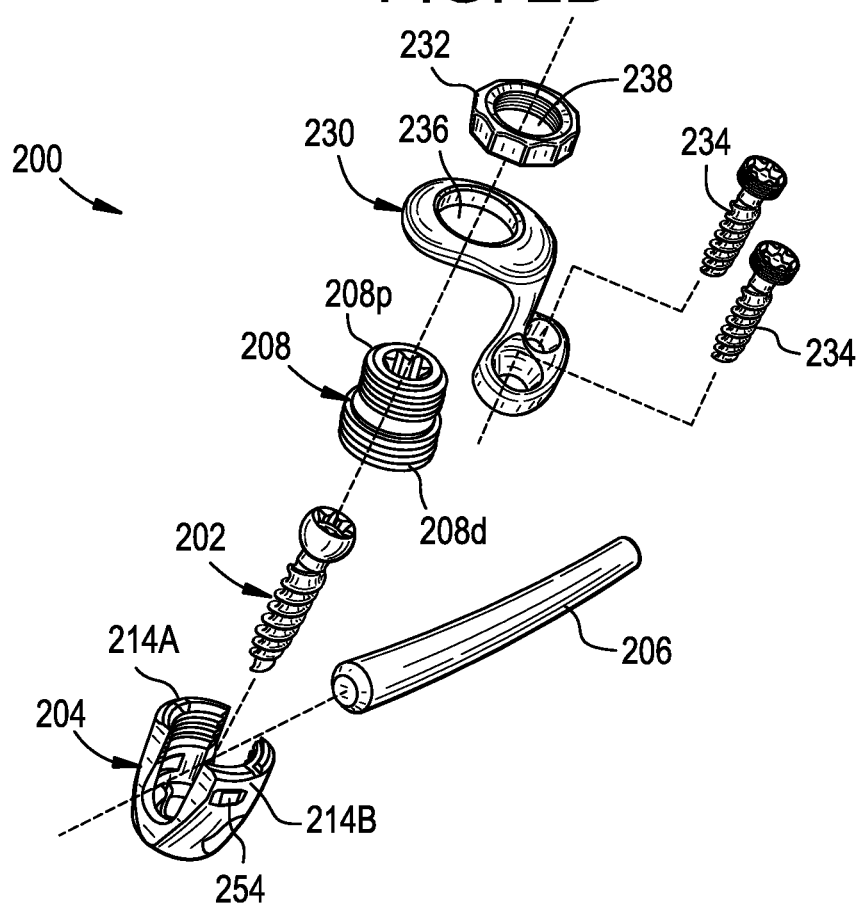
FIG. 2B is a perspective exploded view of the bone anchor assembly and spinal rod of FIG. 2A.
Figure 2C:
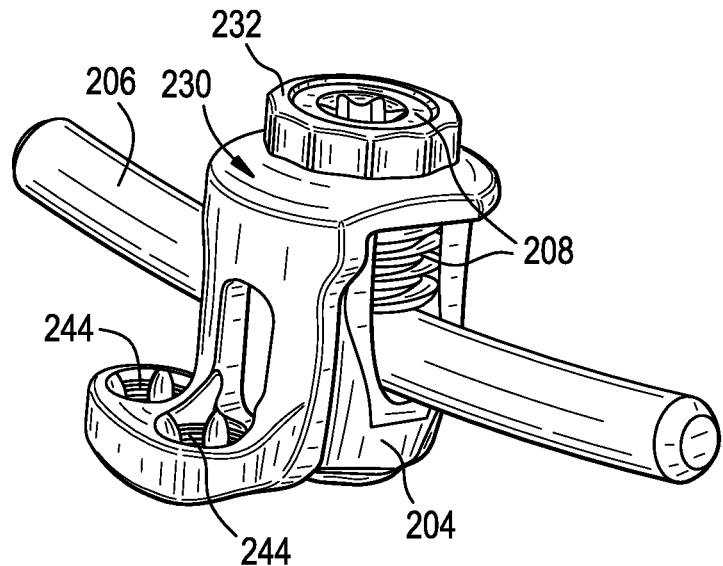
FIG. 2C is a perspective view of the bone anchor assembly and spinal rod of FIG. 2A.
Figure 2D:
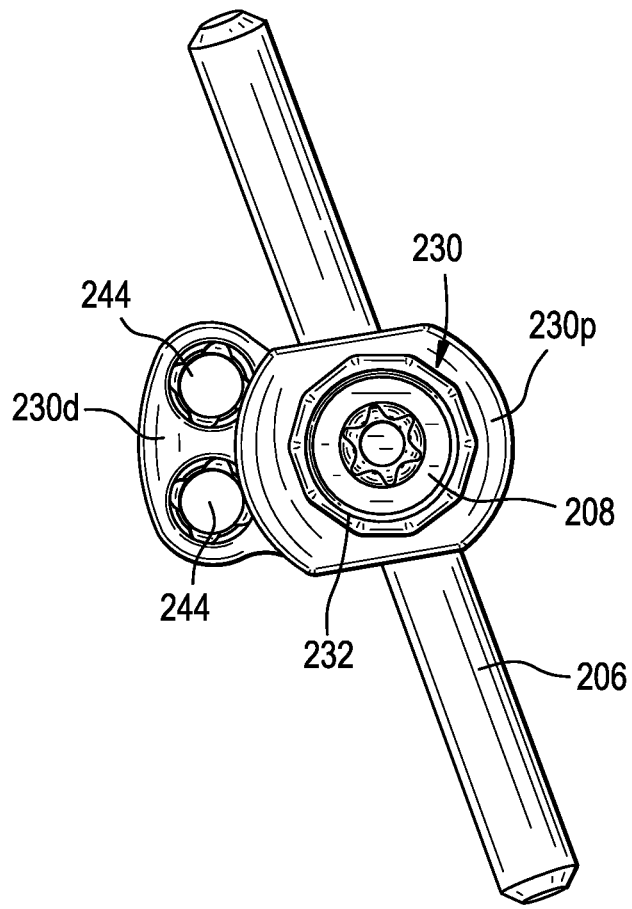
FIG. 2D is a top view of the bone anchor assembly and spinal rod of FIG. 2A.
Figure 2E:
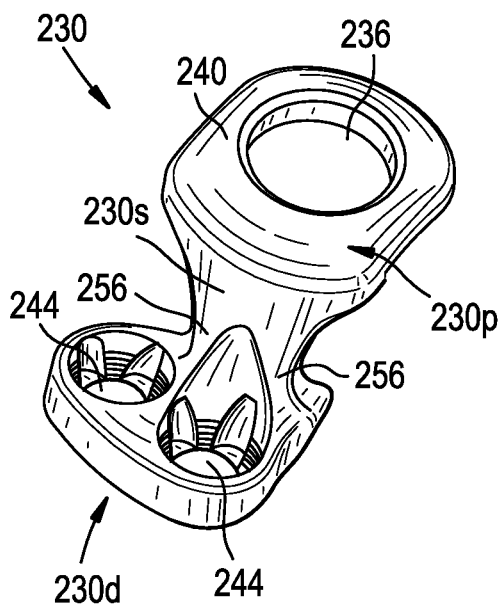
FIG. 2E is a perspective view of a wing of the bone anchor assembly of FIG. 2A.
Figure 2F:
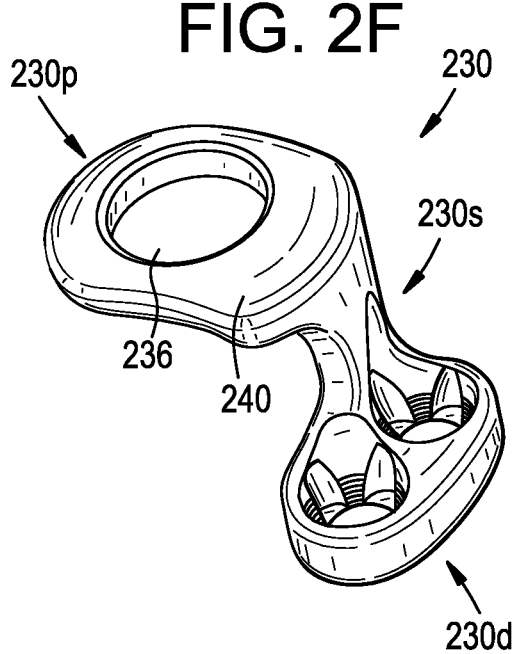
FIG. 2F is another perspective view of a wing of the bone anchor assembly of FIG. 2A.
Figure 2G:
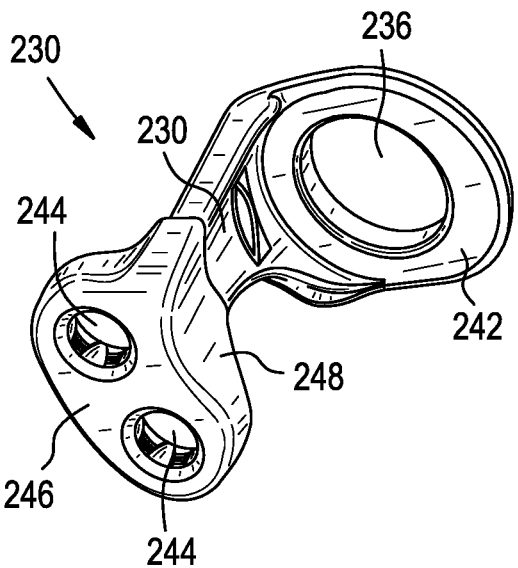
FIG. 2G is another perspective view of a wing of the bone anchor assembly of FIG. 2A.
Figure 2H:
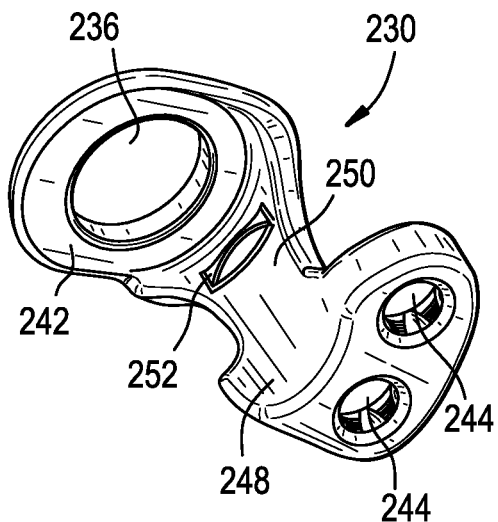
FIG. 2H is another perspective view of a wing of the bone anchor assembly of FIG. 2A.
Figure 2I:
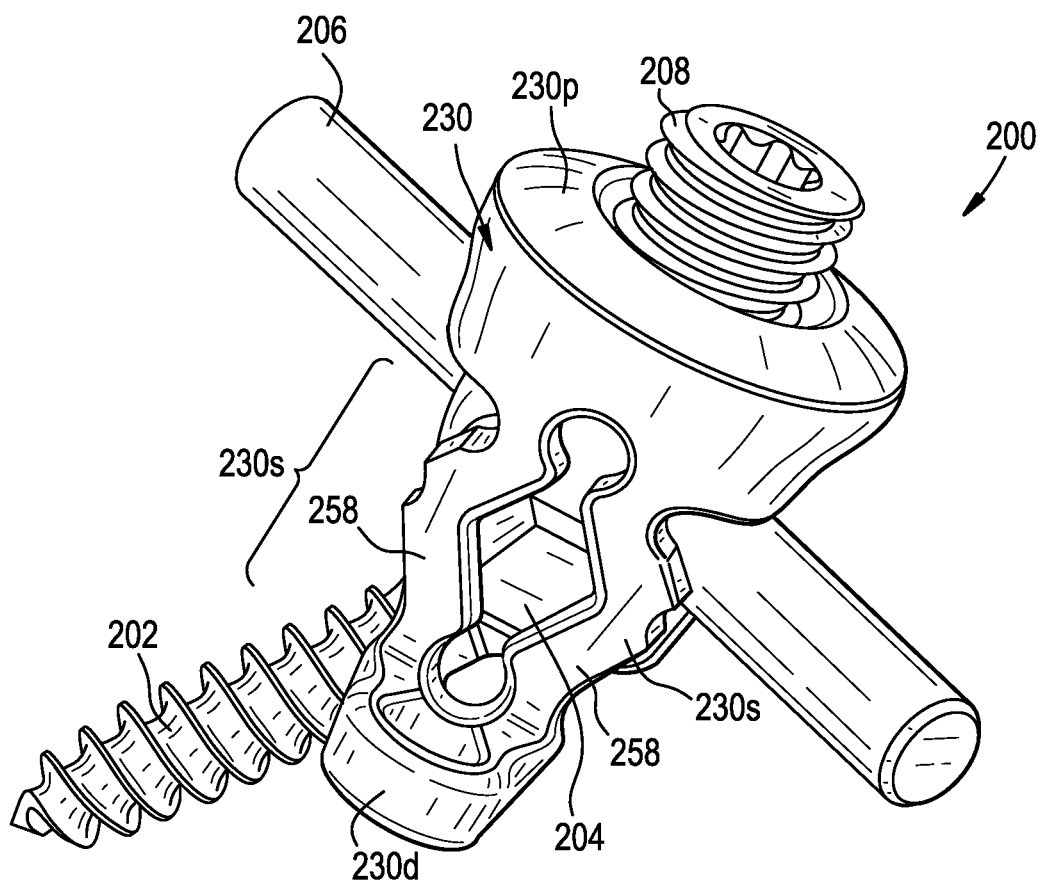
FIG. 2I is a perspective view of the bone anchor assembly and spinal rod of FIG. 2A, shown with an adjustable-height wing.
Figure 2J:
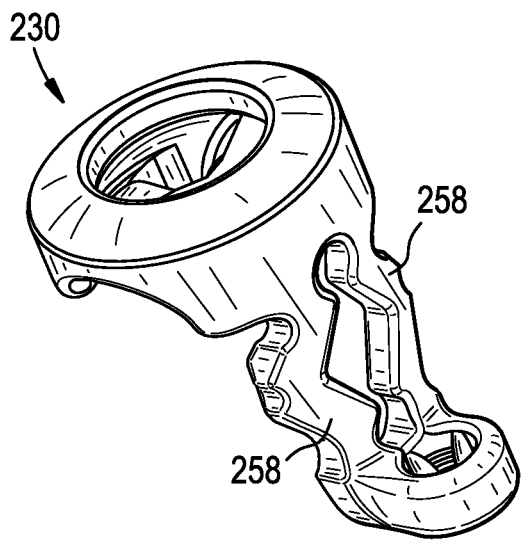
FIG. 2J is a perspective view of a wing of the bone anchor assembly of FIG. 2I.
Figure 2K:
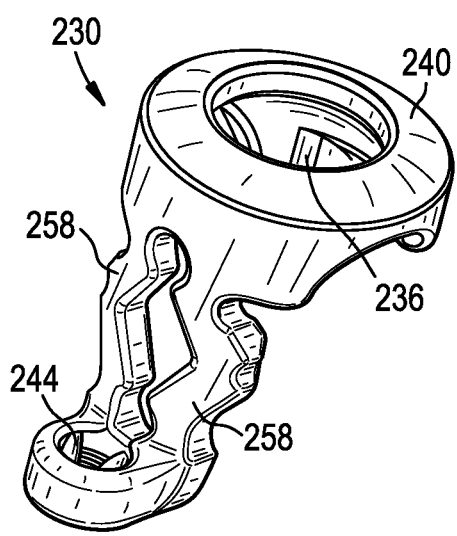
FIG. 2K is another perspective view of a wing of the bone anchor assembly of FIG. 2I.
Figure 2L:
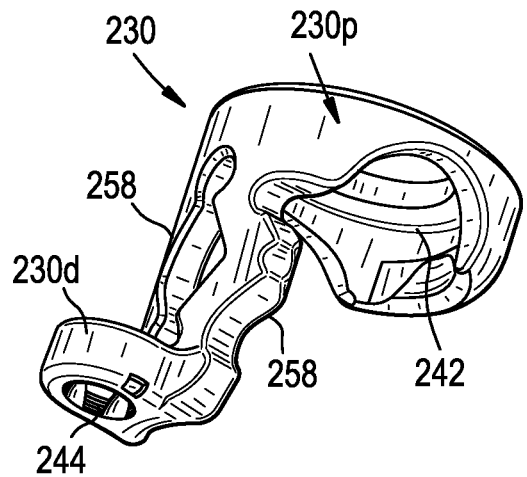
FIG. 2L is another perspective view of a wing of the bone anchor assembly of FIG. 2I.
Figure 2M:
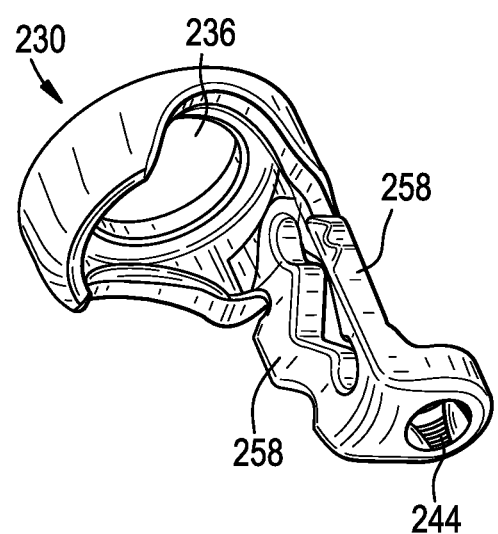
FIG. 2M is another perspective view of a wing of the bone anchor assembly of FIG. 2I.

The bone anchor assembly 200 can provide significant flexibility for the surgeon. The wing 230 can be easily flipped around to be positioned on either side of the rod 206 (e.g., on a medial side or a lateral side of the rod). The wing 230 can be freely rotated about the closure mechanism 208 prior to final locking of the wing to the receiver member 204, allowing the auxiliary bone anchor holes 244 to be positioned at various locations with respect to the spinal rod 206, as shown in FIG. 2D. As described in detail above, the wing 230 can be deformable or flexible, or can include deformable or flexible portions, to allow the wing to fit snugly with the receiver member 204, to match a contour of the bone surface, to reposition the auxiliary bone anchor holes 244 with respect to the receiver member, and/or to adjust a height of the wing to accommodate receiver members of different heights or situations where the primary bone anchor 202 is over or under inserted into the bone.

Referring again to FIG. 2A, the proximal-most extent of each auxiliary bone anchor 234 can be distal to the spinal rod 206. In other embodiments, the proximal-most extent of each auxiliary bone anchor 234 can be distal to the distal-most extent of the receiver member 204. These configurations can advantageously reduce the overall profile of the assembly 200. The wing 200 can be Z-shaped or substantially Z-shaped.

The wing 230 can extend radially outward from the receiver member 204 (e.g., by a distance equal to the width of the distal portion 230d of the wing). The degree to which the wing 230 extends outward from the receiver member 204 can vary among different embodiments. In the illustrated embodiment, the ratio of wing extension to rod diameter (or the ratio of wing extension to the width of the rod-receiving recess in the receiver member) is about 2:1. In some embodiments, this ratio can be less than about 10:1, less than about 5:1, less than about 3:1, less than about 2:1, less than about 1:1, and/or less than about 0.5:1. In some embodiments, the ratio can be about 10:1, about 5:1, about 3:1, about 2:1, about 1:1, or about 0.5:1.

The centers of the auxiliary bone anchor holes 244 (and thus at least a portion of the auxiliary bone anchors 234 disposed therein) can be spaced radially apart from the center of the opening in the receiver member 204 in which the primary bone anchor 202 is disposed. In some embodiments, this spacing can be less than about 2.5 times the diameter of the receiver member 204. In some embodiments, this spacing can be less than about 2 times the diameter of the receiver member 204. In some embodiments, this spacing can be less than the diameter of the receiver member 204. In some embodiments, this spacing can be between about 5 mm and about 10 mm. In some embodiments, this spacing can be about 7.5 mm. In some embodiments, the auxiliary bone anchors 234 can be contained within an envelope no bigger than 2.5 times the diameter of the receiver member 204. In some embodiments, the auxiliary bone anchors 234 can be contained within an envelope no bigger than 2 times the diameter of the receiver member 204.

The auxiliary bone anchors 234 can include any of the features of the bone anchor 202 described above, and any of a variety of other bone screws or other anchors can be used instead or in addition. As noted above, the auxiliary bone anchors 234 can have threaded proximal heads to facilitate variable-angle locking with the wing 230. In some embodiments, the auxiliary bone anchors 234 can have a length of about 6 mm to about 20 mm (e.g., in embodiments used for cervical applications). In some embodiments, the auxiliary bone anchors 234 can have a length of about 6 mm to about 100 mm (e.g., in embodiments used for lumbar or sacral applications). The length of the auxiliary bone anchors 234 can be selected based on various factors, including the available safe bone at any given attachment location. The auxiliary bone anchors 234 can have a length equal to that of the primary bone anchor 202. The auxiliary bone anchors 234 can have a length less than that of the primary bone anchor 202. The auxiliary bone anchors 234 can have a length that is between about 60% and about 80% of the length of the primary bone anchor 202. The auxiliary bone anchors 234 can have a length that is about 70% of the length of the primary bone anchor 202. The auxiliary bone anchors 234 can have a length of about 10 mm. The auxiliary bone anchors 234 can have a length of about 14 mm. In some embodiments, two 10 mm auxiliary bone anchors can be used with one 14 mm primary bone anchor. In some embodiments, one 14 mm auxiliary bone anchor can be used with one 14 mm primary bone anchor. The auxiliary bone anchors 234 can have a shank diameter equal to that of the primary bone anchor 202. The auxiliary bone anchors 234 can have a shank diameter less than that of the primary bone anchor 202. The auxiliary bone anchors 234 can have a shank diameter that is between about 50% and about 70% of the shank diameter of the primary bone anchor 202. The auxiliary bone anchors 234 can have a shank diameter that is about 60% of the shank diameter of the primary bone anchor 202.

FIGS. 3A-3I illustrate an exemplary embodiment of a bone anchor assembly 300, shown with a spinal rod 306. As shown, the bone anchor assembly 300 can include a bone anchor 302, a receiver member 304, a closure mechanism 308, a grommet or plate 360, and one or more auxiliary bone anchors 334. In use, a saddle portion of the plate can be disposed between the rod 306 and the receiver member 304 to secure the plate 360 to the receiver member, thereby providing the ability to augment fixation of the bone anchor 302 with the one or more auxiliary bone anchors 334.

Except as described below or as will be readily appreciated by one having ordinary skill in the art, the bone anchor 302, receiver member 304, and closure mechanism 308 are substantially similar to the bone anchor 102, receiver member 104, and closure mechanism 108 described above. A detailed description of the structure and function thereof is thus omitted here for the sake of brevity. The bone anchor assembly 300 can include any one or more of the features of the bone anchor assembly 100 described above.

As shown in FIGS. 3C-3F, the grommet or plate 360 can include a primary opening 362 configured to receive at least a portion of the receiver member 304 therethrough. The plate can also include one or more openings 364 configured to receive a bone anchor 334 therethrough. While a single bone anchor opening 364 is shown in the illustrated embodiment, it will be appreciated that the plate 360 can include any number of bone anchor openings (e.g., one, two, three, four, five, and so on). The bone anchor openings 364 can include any of a number of features for accepting bone anchors 334 at varying angles and/or increasing the security and stability with which bone anchors can be secured to the plate 360. Exemplary features that can be included are disclosed in U.S. Pat. No. 7,637,928, issued on Dec. 29, 2009; U.S. Pat. No. 8,343,196, issued on Jan. 1, 2013; U.S. Pat. No. 8,574,268, issued on Nov. 5, 2013; U.S. Pat. No. 8,845,697, issued on Sep. 30, 2014; and U.S. Pat. No. 8,758,346, issued on Jun. 24, 2014, which are each hereby incorporated by reference herein. For example, the bone anchor opening 364 can be at least partially threaded to receive a variable-angle locking screw having a threaded proximal head. As shown, the opening 364 can have a plurality of columns of threads spaced apart to define a plurality of non-threaded recesses. In the illustrated embodiment, the opening 364 has four columns of threads. The columns of threads can be arranged around the inner surface of the opening 364 for engaging threads on the heads of locking auxiliary bone anchors and/or variable-angle locking auxiliary bone anchors. The auxiliary bone anchor 334 can thus be locked with the plate 360 coaxially with the central axis of the opening 364 or at a selected angle within a range of selectable angles relative to the central axis of the opening. The auxiliary bone anchor 334 can include features to facilitate this variable-angle locking, such as a proximal head that is at least partially spherical having a thread with a profile that follows the arc-shaped radius of curvature of the spherical portion of the head. The variable-angle capability of the screw/opening interface can allow the user to place locking auxiliary bone anchors into the bone at any angle within defined angulation limits, thus providing improved placement flexibility and eliminating or reducing the need to conform the plate to the bone surface to achieve a desired insertion angle. The auxiliary bone anchor 334 can be driven into the bone with a diverging or converging longitudinal axis relative to the primary bone anchor 302 and/or relative to other auxiliary bone anchors 334, which can provide improved resistance to pullout. In some embodiments, the interior surface of the opening 334 can be smooth or spherical, without threads or locking features.

The central axis of the opening 364 can be perpendicular or substantially perpendicular to a distal-facing surface of the plate 360. Alternatively, the opening 364 can have a central axis that extends at an oblique angle with respect to the distal-facing surface. In the illustrated embodiment, the central axis of the opening 364 extends at an angle of about 0 degrees with respect to the distal-facing surface. In some embodiments, the central axis of the opening 364 can extend at an angle of between about 0 degrees and about 15 degrees with respect to the distal-facing surface (e.g., embodiments used for bony attachment locations that allow direct proximal to distal screw insertion). In some embodiments, the central axis of the opening 364 can extend at an angle of between about 15 degrees and about 45 degrees with respect to the distal-facing surface (e.g., embodiments used for bony attachment locations where an angled trajectory may avoid or target specific anatomy). An angled or divergent central axis can advantageously increase the pullout resistance of the construct.

The plate 360 can include a saddle portion 366 that extends across at least a portion of the primary opening 362. The saddle portion 366 can span entirely across the primary opening 362, or can be cantilevered as shown to project out across the opening without contacting the opposite side of the opening. The latter configuration can advantageously facilitate bending of the saddle portion 366 with respect to the rest of the plate 360, thereby allowing the position of the plate with respect to the receiver member 304 to be adjusted (e.g., to bend the plate down into contact with the bone surface). The saddle portion 366 can include a distal facing surface 366d that mimics the distal facing surface of a spinal fixation or stabilization element with which the bone anchor assembly 300 is to be used. For example, in the case of a cylindrical spinal rod 306, the distal-facing surface 366d of the saddle portion 366 can define a section of a cylinder having a radius equal to or substantially equal to the diameter of the spinal rod. The proximal-facing surface 366p of the saddle portion 366 can define a seat configured to receive the spinal fixation or stabilization element therein. In the illustrated embodiment, the seat 366p is sized and shaped to receive a cylindrical spinal rod 306 therein. The radius of curvature of the proximal-facing seat 366p can be equal to or substantially equal to that of the rod-receiving channel of the receiver member 304.

The saddle portion 366 can effectively divide the primary opening 362 into first and second openings on either side of the saddle portion, each sized to receive a corresponding one of the arms 314A, 314B of the receiver member 304. When assembled, the opposed arms 314A, 314B of the receiver member can be inserted through the first and second openings such that the plate 360 surrounds the receiver member 304 and such that the saddle portion 366 is seated within the rod-receiving recess of the receiver member. The spinal rod 306 can then be seated on the proximal-facing surface 366p of the saddle portion 366, between the opposed arms 314A, 314B of the receiver member 304, and locked in place with the closure mechanism 308 as described above, thereby also locking the plate 360 to the receiver member. An auxiliary bone anchor 334 can be inserted through each of the one or more bone anchor openings 364 in the plate to augment the fixation provided by the primary bone anchor 302.

The primary opening 362 in the plate can be defined by a first sidewall 368 that is generally ring-shaped and that intersects with a second sidewall 370 that is also generally ring-shaped and that defines the one or more auxiliary bone anchor openings 364. The height of the first sidewall 368 can be reduced at the junction with the second sidewall 370 or in areas adjacent thereto to facilitate bending of the plate 360 to reposition the auxiliary bone anchor opening 364 with respect to the receiver member 304.

The first and second sidewalls 368, 370 can be formed integrally as a monolithic unit as shown, or one or more of said components can be separate and selectively attachable to the other. In some embodiments, a kit of modular components can be provided to allow selection of the components most appropriate for a given use. For example, a first sidewall 368 of appropriate size can be selected based on the size of the receiver member 304 or the size of the spinal rod 306. By way of further example, one or more modular second sidewalls 370 can be attached to the first sidewall 368, e.g., depending on the number of auxiliary bone anchors 334 that are to be used.

The second sidewall 370, and thus the auxiliary bone anchor opening 364 defined thereby, can be positioned at any of a variety of locations about the perimeter of the first sidewall 368. In the illustrated embodiment, for example, the auxiliary bone anchor opening 364 is positioned approximately at a "5 o'clock" or "lower" position with respect to the saddle portion 366, such that the center point of the auxiliary bone anchor opening 364 is offset laterally from the saddle portion and aligned with an inferior end of the saddle portion. In other embodiments, the auxiliary bone anchor opening 364 can be positioned approximately at a "3 o'clock" or "middle" position with respect to the saddle portion 366, such that the center point of the auxiliary bone anchor opening 364 is offset laterally from the saddle portion and aligned with a longitudinal midpoint of the saddle portion. In other embodiments, the auxiliary bone anchor opening 364 can be positioned approximately at a "1 o'clock" or "upper" position with respect to the saddle portion 366, such that the center point of the auxiliary bone anchor opening 364 is offset laterally from the saddle portion and aligned with a superior end of the saddle portion. A kit can be provided including a plurality of plates 360, each including auxiliary bone anchor openings 364 positioned at different locations with respect to the saddle portion 366, to give the user flexibility in locating the auxiliary bone anchor 334 relative to the rod 306. This can allow the user to select a plate 360 that will position the auxiliary bone anchor 334 in a good position to get bone purchase.

One or more portions of the plate 360 can be flexible or deformable to allow the plate to be custom-tailored for a particular situation. For example, as noted above, the portion of the plate 360 in which the bone anchor opening(s) 364 are formed can be bent or flexed to reposition said portion with respect to the portion of the plate in which the receiver member 304 is disposed. The plate 360 can be contoured before implantation or in situ. The plate 360 can be contoured using a separate bending instrument, or by tightening the bone anchors 334 to deform the plate into intimate contact with the bone surface. The plate 360 can be pre-shaped or pre-contoured, e.g., during manufacture, to match a bone surface or construct with which the bone anchor assembly 300 is to be used.

In some cases, the thickness of the saddle portion 366 can cause the spinal rod 306 to be raised up within the receiver member 304 to a degree that prevents sufficient attachment of the closure mechanism 308 or prevents attachment of the closure mechanism altogether. In such cases, the bone anchor assembly 300 can include a cap 372, e.g., of the type shown in FIG. 3H. The cap 372 can attach to the proximal end of the receiver member 304. The cap 372 can include a threaded central opening sized to receive the closure mechanism 308. Accordingly, the cap 372 can functionally extend the height of the threaded portion of the receiver member 304 to accommodate both the rod 306 and the saddle portion 366 between the rod-receiving channel of the receiver member 304 and the closure mechanism 308. The illustrated cap 372 includes a generally U-shaped channel sized to accommodate the spinal rod 306. The cap 372 can be attached to the receiver member 304 in any of a variety of ways. For example, the cap 372 can include one or more projections that engage with a corresponding one or more recesses formed in the receiver member 304, or the receiver member can include one or more projections that engage with a corresponding one or more recesses formed in the cap. The cap 372 can snap fit onto the receiver member 304. The cap 372 can slide onto the receiver member 304 from the side with a tongue and groove or dovetail connection. The cap 372 can lock onto the receiver member 304 by a quarter-turn rotation of the cap relative to the receiver member.

Figure 3A:
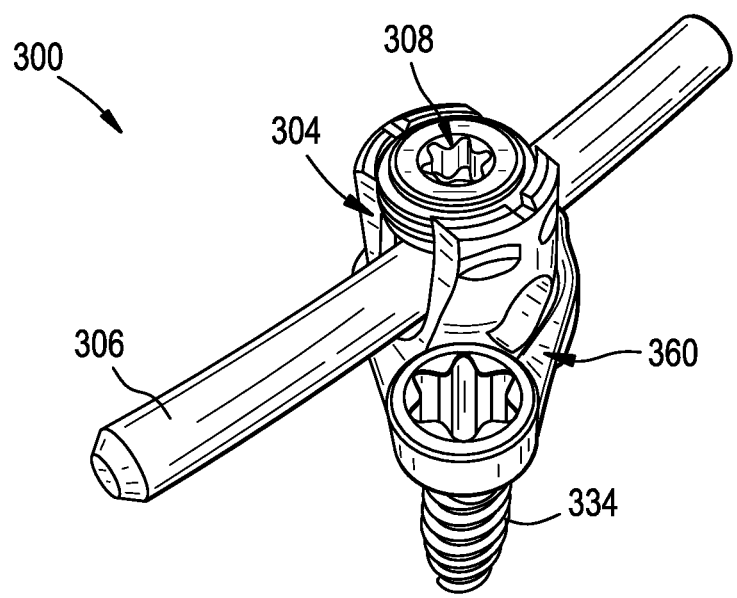
FIG. 3A is a perspective view of a bone anchor assembly and a spinal rod.
Figure 3B:
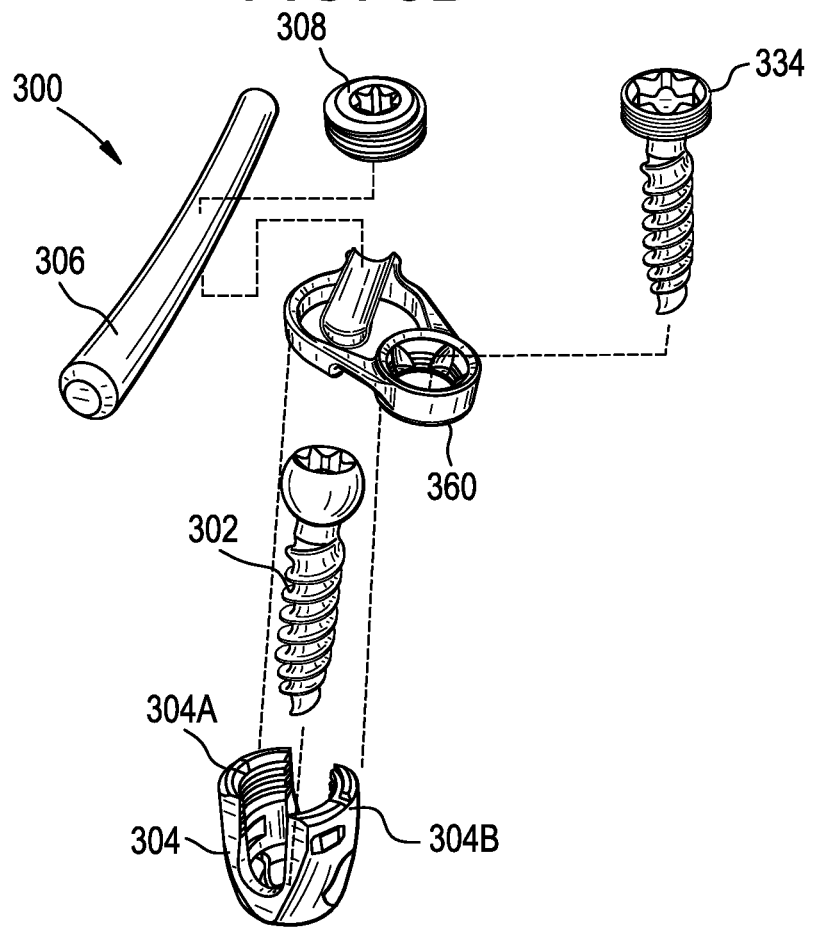
FIG. 3B is a perspective exploded view of the bone anchor assembly and spinal rod of FIG. 3A.
Figure 3C:
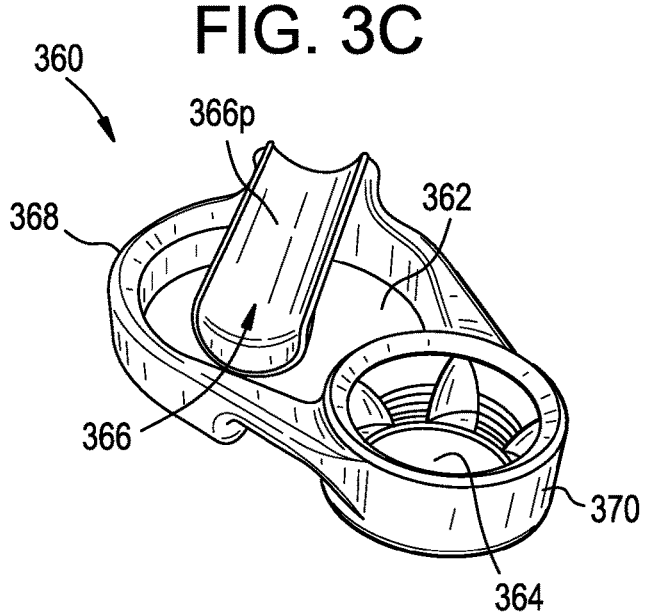
FIG. 3C is a perspective view of a plate of the bone anchor assembly of FIG. 3A.
Figure 3D:
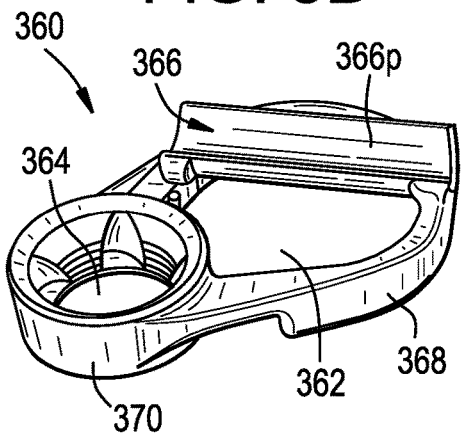
FIG. 3D is another perspective view of a plate of the bone anchor assembly of FIG. 3A.
Figure 3E:
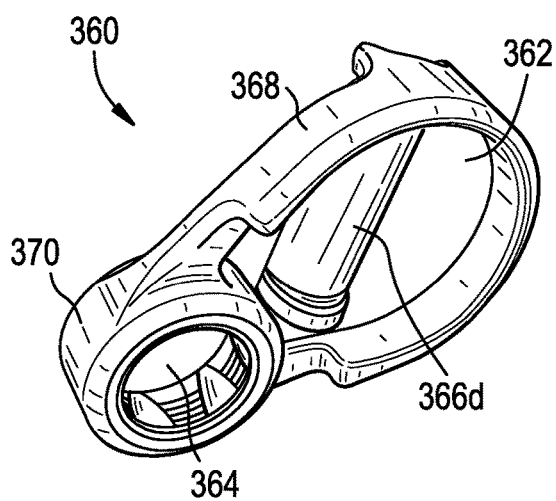
FIG. 3E is another perspective view of a plate of the bone anchor assembly of FIG. 3A.
Figure 3F:
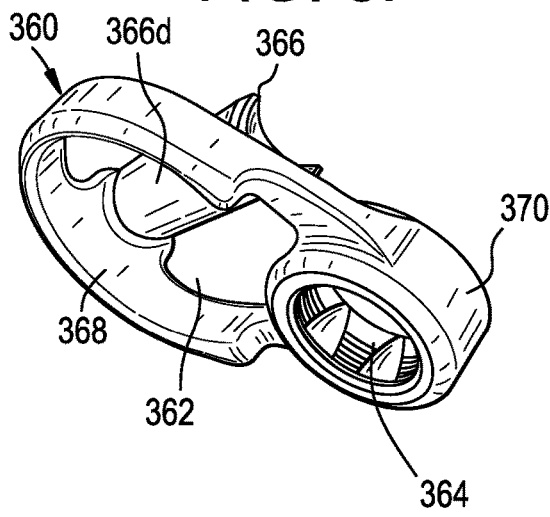
FIG. 3F is another perspective view of a plate of the bone anchor assembly of FIG. 3A.
Figure 3G:
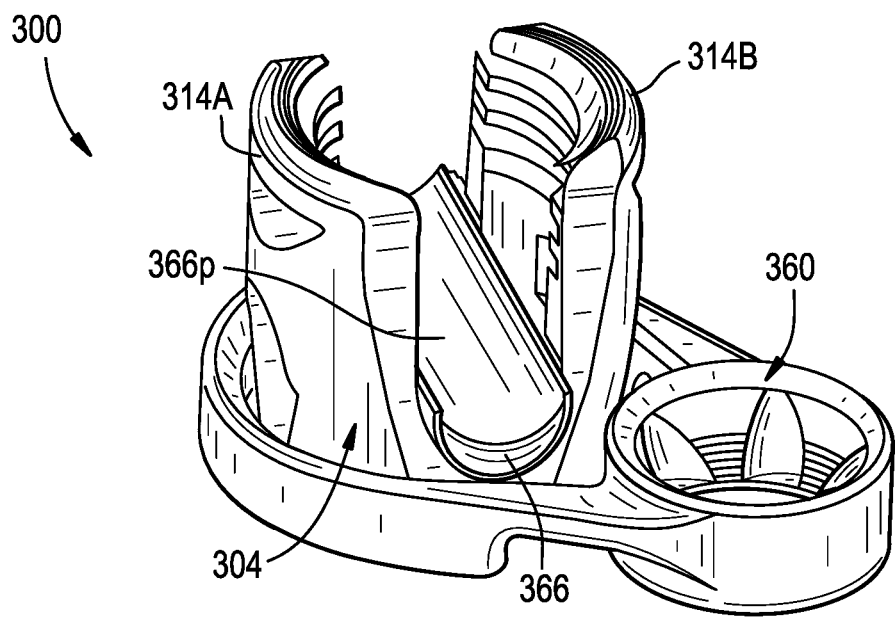
FIG. 3G is a perspective view of a receiver member and plate of the bone anchor assembly of FIG. 3A.
Figure 3H:
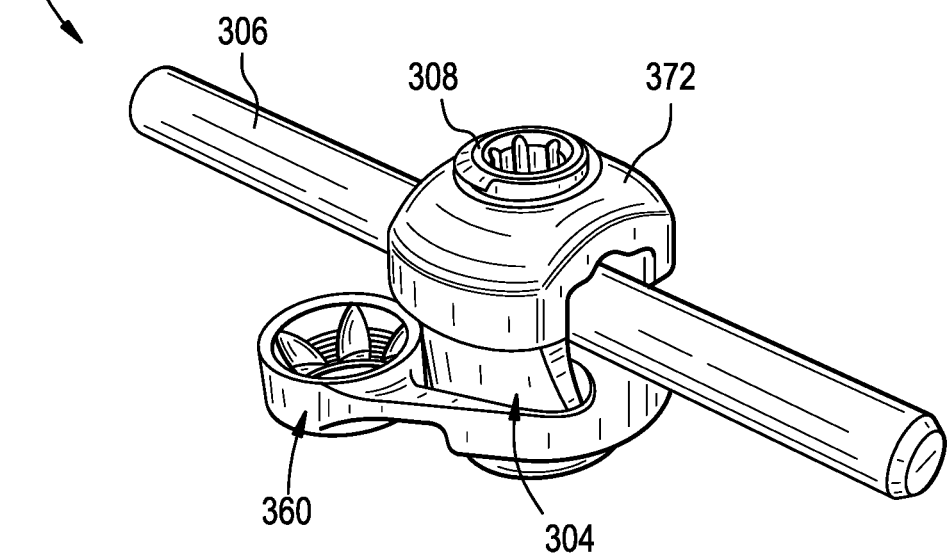
FIG. 3H is a perspective view of the bone anchor assembly and spinal rod of FIG. 3A, shown with a cap.
Figure 3I:
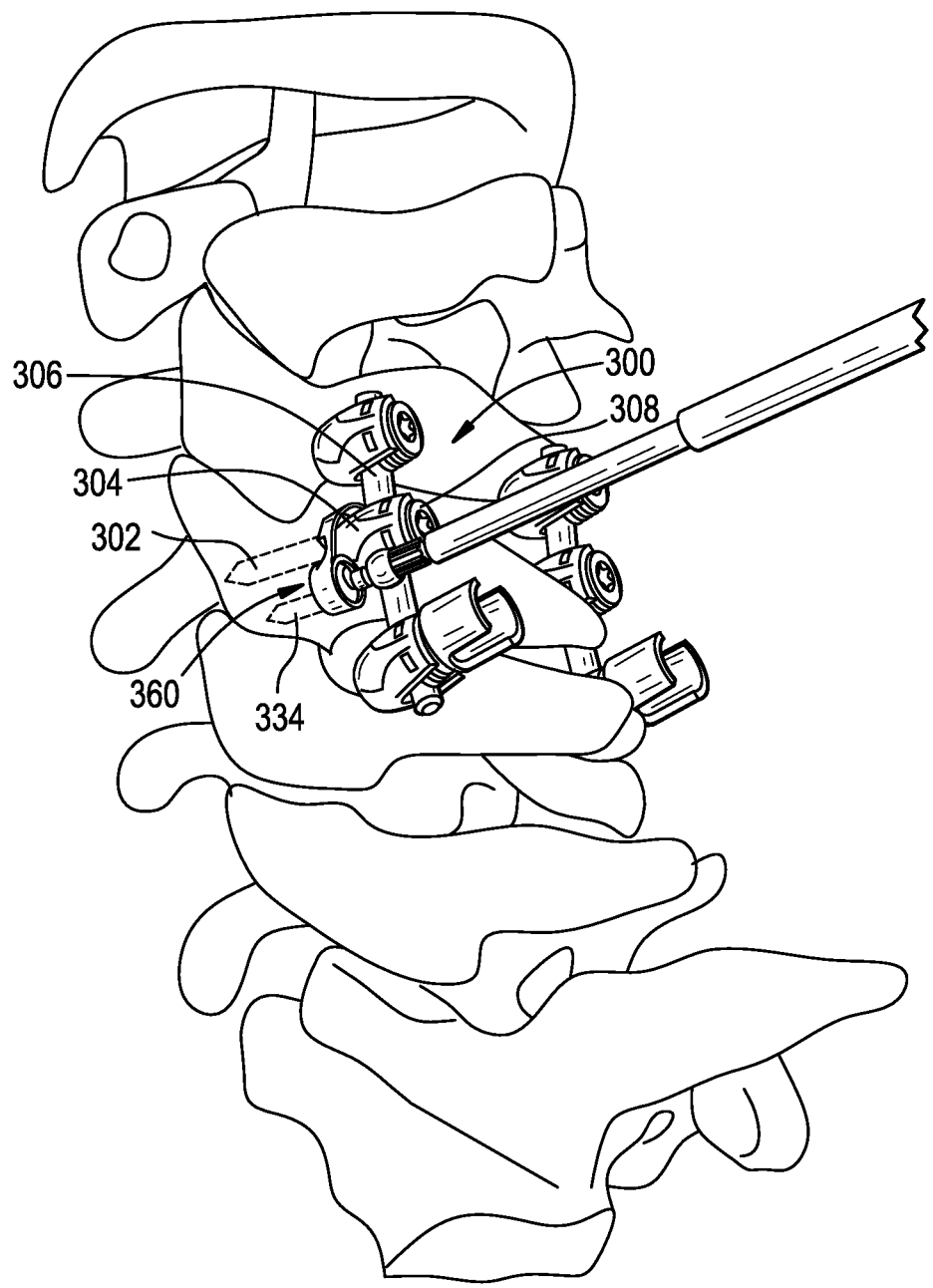
FIG. 3I is a perspective view of a human spine with the bone anchor assembly and spinal rod of FIG. 3A coupled thereto.

The bone anchor assembly 300 can provide significant flexibility for the surgeon. The plate 360 can be easily flipped around to be positioned on either side of the rod 306 (e.g., on a medial side or a lateral side of the rod). As described in detail above, the plate 360 can be deformable or flexible, or can include deformable or flexible portions, to allow the plate to fit snugly with the receiver member 304, to match a contour of the bone surface, to reposition the auxiliary bone anchor hole(s) 364 with respect to the receiver member, and/or to adjust a height of the plate to accommodate receiver members of different heights or situations where the primary bone anchor 302 is over or under inserted into the bone. The bone anchor assembly 300 is shown in FIG. 3I installed as part of a multi-level spinal fixation construct. As shown, the plate 360 allows an auxiliary bone anchor 334 to be installed at the same vertebral level as the primary bone anchor 302 to augment the fixation of the primary bone anchor.

Referring again to FIG. 3A, the proximal-most extent of each auxiliary bone anchor 334 can be distal to the spinal rod 306. In other embodiments, the proximal-most extent of each auxiliary bone anchor 334 can be distal to the distal-most extent of the receiver member 304. These configurations can advantageously reduce the overall profile of the assembly 300.

The centers of the auxiliary bone anchor hole(s) 364 (and thus at least a portion of the auxiliary bone anchor(s) 334 disposed therein) can be spaced radially apart from the center of the opening in the receiver member 304 in which the primary bone anchor 302 is disposed. In some embodiments, this spacing can be less than about 2.5 times the diameter of the receiver member 304. In some embodiments, this spacing can be less than about 2 times the diameter of the receiver member 304. In some embodiments, this spacing can be less than the diameter of the receiver member 304. In some embodiments, this spacing can be between about 5 mm and about 10 mm. In some embodiments, this spacing can be about 7.5 mm. In some embodiments, the auxiliary bone anchors 334 can be contained within an envelope no bigger than 2.5 times the diameter of the receiver member 304. In some embodiments, the auxiliary bone anchors 334 can be contained within an envelope no bigger than 2 times the diameter of the receiver member 304.

The auxiliary bone anchors 334 can include any of the features of the bone anchor 302 described above, and any of a variety of other bone screws or other anchors can be used instead or in addition. As noted above, the auxiliary bone anchors 334 can have threaded proximal heads to facilitate variable-angle locking with the plate 360. In some embodiments, the auxiliary bone anchors 334 can have a length of about 6 mm to about 20 mm (e.g., in embodiments used for cervical applications). In some embodiments, the auxiliary bone anchors 334 can have a length of about 6 mm to about 100 mm (e.g., in embodiments used for lumbar or sacral applications). The length of the auxiliary bone anchors 334 can be selected based on various factors, including the available safe bone at any given attachment location. The auxiliary bone anchors 334 can have a length equal to that of the primary bone anchor 302. The auxiliary bone anchors 334 can have a length less than that of the primary bone anchor 302. The auxiliary bone anchors 334 can have a length that is between about 60% and about 80% of the length of the primary bone anchor 302. The auxiliary bone anchors 334 can have a length that is about 70% of the length of the primary bone anchor 302. The auxiliary bone anchors 334 can have a length of about 10 mm. The auxiliary bone anchors 334 can have a length of about 14 mm. In some embodiments, two 10 mm auxiliary bone anchors can be used with one 14 mm primary bone anchor. In some embodiments, one 14 mm auxiliary bone anchor can be used with one 14 mm primary bone anchor. The auxiliary bone anchors 334 can have a shank diameter equal to that of the primary bone anchor 302. The auxiliary bone anchors 334 can have a shank diameter less than that of the primary bone anchor 302. The auxiliary bone anchors 334 can have a shank diameter that is between about 50% and about 70% of the shank diameter of the primary bone anchor 302. The auxiliary bone anchors 334 can have a shank diameter that is about 60% of the shank diameter of the primary bone anchor 302.

The saddle portion 366 can extend completely across the rod-receiving recess of the receiver member 304. The saddle portion 366 can extend across less than an entirety of the rod-receiving recess of the receiver member 304 (e.g., across only a portion of the rod-receiving recess). The saddle portion 366 can be omitted altogether. For example, the plate 360 can include an alternative distal facing portion to bear against the receiver member 304 and transfer the holding force of the auxiliary bone anchors 334 to the receiver member. Exemplary distal facing portions can include a lip, a shelf, a face, a tapered portion, and/or teeth that can mesh or engage with a portion of the receiver member 304.

FIGS. 4A-4E illustrate an exemplary embodiment of a bone anchor assembly 400, shown with a spinal rod 406. As shown, the bone anchor assembly 400 can include a bone anchor 402, a receiver member 404, a closure mechanism 408, a hook 474, a washer or collar 476, and a locking screw 478. In use, the collar 476 and locking screw 478 can be used to attach the hook 474 to the receiver member 404. The hook 474 can be hooked onto or engaged with a portion of the patient anatomy or a nearby implant to augment fixation of the bone anchor 402.

Except as described below or as will be readily appreciated by one having ordinary skill in the art, the bone anchor 402, receiver member 404, and closure mechanism 408 are substantially similar to the bone anchor 102, receiver member 104, and closure mechanism 108 described above. A detailed description of the structure and function thereof is thus omitted here for the sake of brevity. The bone anchor assembly 400 can include any one or more of the features of the bone anchor assembly 100 described above.

The hook 474 can include a body portion 480 with a curved or looped extension 482 projecting therefrom.

The extension 482 can be substantially U-shaped, with an inside curved surface 484 and an outside curved surface 486. The extension 482 can be sized and configured to hook onto a portion of the patient's anatomy (e.g., a lamina, spinous process, or other bone structure of the patient) or onto another implant or implant construct (e.g., a cross-connector, screw, rod, plate, intervertebral implant, or the like). For example, the inside curved surface 484 can form a negative or a substantial negative of the anatomy or implant.

Figure 4A:
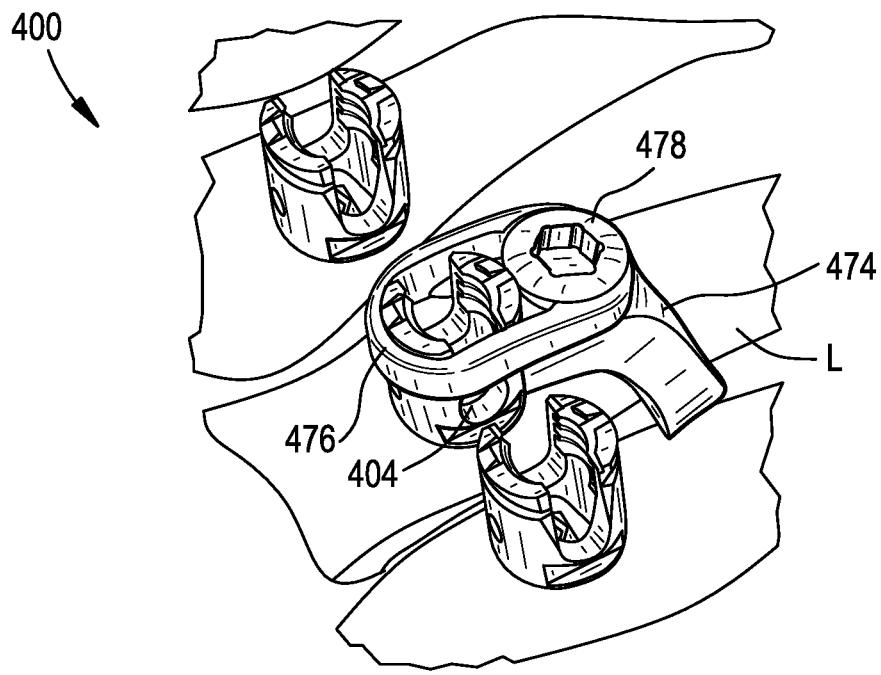
FIG. 4A is a perspective view of a bone anchor assembly and a spinal rod coupled to a human spine.
Figure 4B:
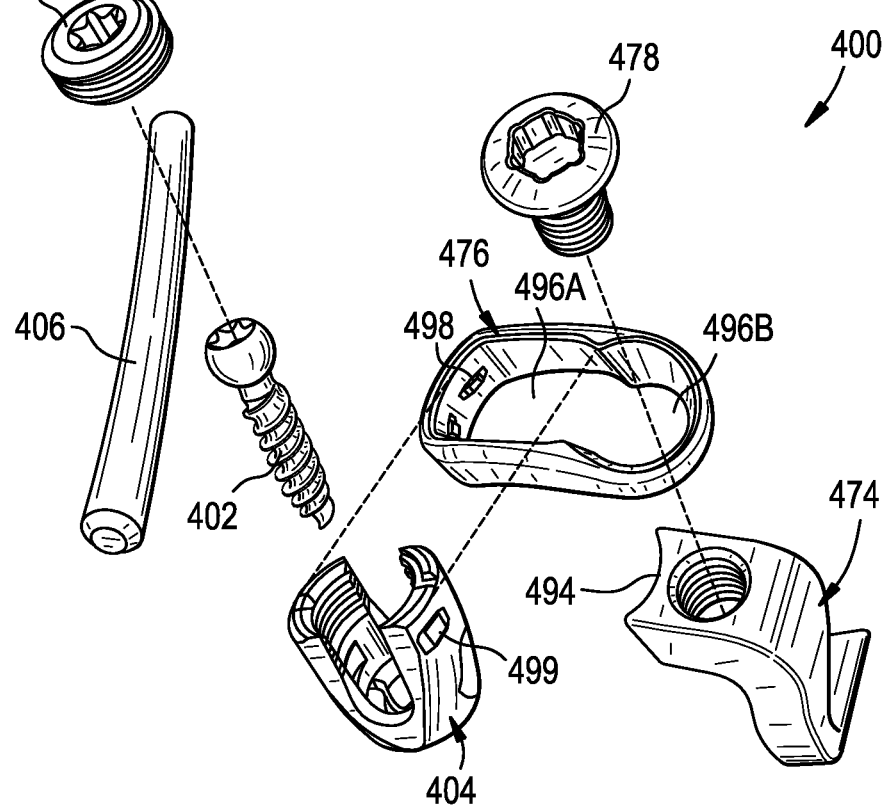
FIG. 4B is a perspective exploded view of the bone anchor assembly and spinal rod of FIG. 4A.
Figure 4C:
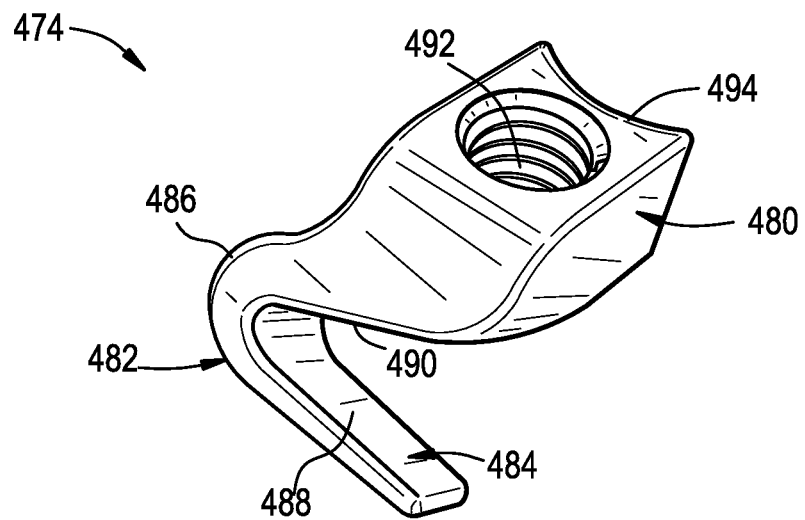
FIG. 4C is a perspective view of a hook of the bone anchor assembly of FIG. 4A.
Figure 4D:
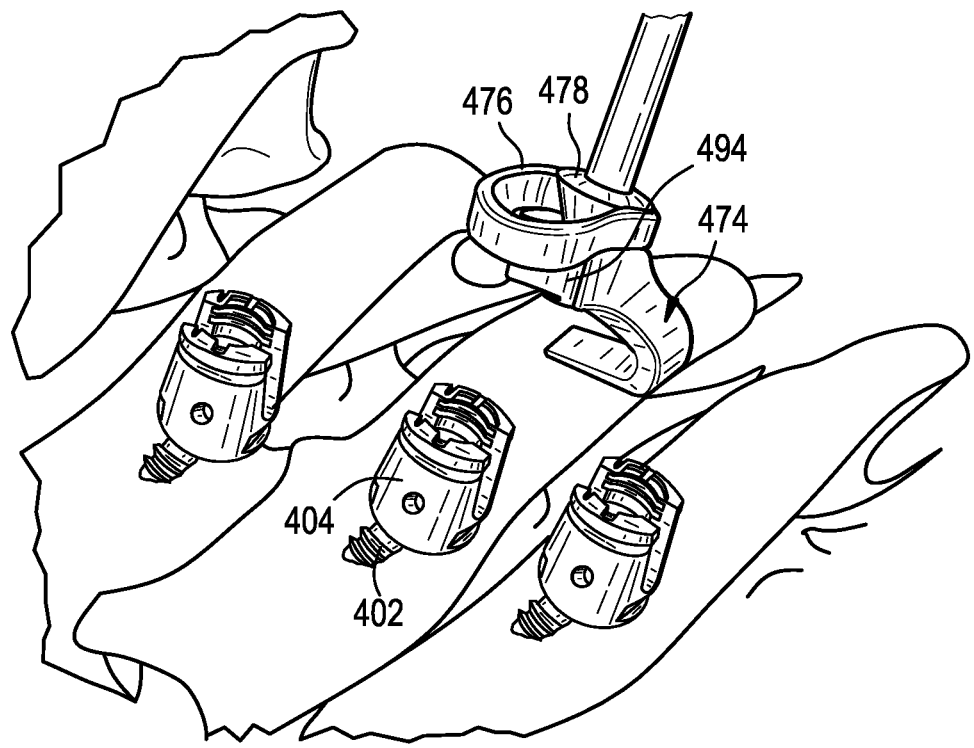
FIG. 4D is a perspective view of the bone anchor assembly of FIG. 4A being assembled in situ.

As shown in FIG. 4A, the hook 474 can be coupled to the lamina L of the patient such that a proximal-facing surface 488 of the inside curve 484 of the extension 482 abuts a distal facing surface of the lamina and such that a distal-facing surface 490 of the inside curve 484 of the extension 482 abuts a proximal-facing surface of the lamina.

While a single extension 482 is shown in the illustrated embodiment, it will be appreciated that the hook 474 can include any number of extensions (e.g., one, two, three, four, five, and so on).

One or more portions of the hook 474 can be flexible or deformable to allow the hook to be custom-tailored for a particular situation. For example, the extension 482 of the hook 474 can be contoured to match the anatomy or implant onto which the extension is to be hooked. The hook 474 can be contoured before implantation or in situ. The hook 474 can be contoured using a separate bending instrument, or by tightening the locking screw 478 to deform the hook into intimate contact with the anatomy or implant. The hook 474 can be pre-shaped or pre-contoured, e.g., during manufacture, to match an anatomy or implant with which the bone anchor assembly 400 is to be used.

In some embodiments, a kit of modular hooks 474 can be provided to allow selection of the hook or hooks most appropriate for a given use. For example, hooks 474 having extensions 482 of varying sizes that correspond to the varying sizes of laminae found in a patient population or the varying sizes of laminae found within a single human spine can be included in the kit and the most appropriately sized hook can be selected for the surgery. Hooks 474 of varying size and/or varying offset relative to the receiver member 404 can be included in a kit.

The body portion 480 of the hook 474 can include an opening 492 for receiving the locking screw 478 to secure the hook to the collar 476. The opening 492 can be threaded such that the locking screw 478 can be threaded into the opening. The body portion 480 of the hook 474 can include a lateral surface 494 that engages a sidewall of the receiver member 404. The lateral surface 494 can form a negative of the sidewall of the receiver member 404, such that the hook 474 can hug the receiver member with minimal or zero gap therebetween. For example, the lateral surface 494 can be concave with a radius of curvature equal or substantially equal to a radius of curvature of the exterior sidewall of the receiver member 404.

The collar 476 can include a first opening 496A sized to receive at least a portion of the receiver member 404 therethrough and a second opening 496B sized to receive the locking screw 478 therethrough. The first and second openings 496A, 496B can intersect one another, such that the collar 476 defines a "snowman" or "figure eight" shaped central opening. The collar 476 can include one or more engagement features for forming a positive interlock with the receiver member 404, which can advantageously prevent the collar from inadvertently sliding off of the receiver member. For example, the collar 476 can include one or more projections 498 that extend radially inward into the first opening 496A to engage corresponding one or more recesses 499 formed in an exterior sidewall of the receiver member 404. In other embodiments, the recesses can be formed in the collar 476 and the projections can be formed on the receiver member 404. The first opening 496A can include one or more flats (e.g., opposed parallel, planar sidewalls as shown) that mate with corresponding one or more flats (e.g., opposed parallel, planar sidewalls) of the receiver member 404 to prevent rotation of the collar 476 with respect to the receiver member.

The second opening 496B of the collar 476 can be circular or semi-circular to accommodate the cylindrical shaft of the locking screw 478. In other embodiments, the second opening 496B can be elongated to allow the locking screw 478 to be secured at any of a variety of locations along a length of the elongated opening. This can advantageously allow the distance between the receiver member 404 and the hook 474 to be adjusted as desired. The second opening 496B can have a conical or tapered countersink shape as shown such that, as the locking screw 478 is tightened, the collar 476 is pushed to the right in FIG. 4A, cinching in the receiver member 404 and locking down the entire assembly.

When assembled, the collar 476 can sit above the spinal rod 406 and extend around the outer periphery of the receiver member 404 to secure the hook 474 to the side of the receiver member. The hook 474 can be hooked onto patient anatomy or another implant to augment the fixation of the bone anchor assembly 400. In some embodiments, the hook 474 can be hooked onto an anatomical structure at the same vertebral level as the bone anchor 402 is inserted. Thus, for example, the bone anchor 402 can be advanced into the pedicle or lateral mass of a vertebra and the hook 474 can be hooked onto a lamina of that same vertebra. As shown in FIG. 4A, the collar 476 does not interfere with insertion of the closure mechanism 408 into the receiver member 404, or with tightening or loosening of the closure mechanism. In addition, the hook 474 and collar 476 can be attached to the receiver member 404 after the rod 406 is installed in the receiver member.

The bone anchor assembly 400 can provide significant flexibility for the surgeon. The collar 476 and hook 474 can be easily flipped around to be positioned on either side of the rod 406 (e.g., on a medial side or a lateral side of the rod). The hook 474 can be deformable or flexible, or can include deformable or flexible portions, to allow the hook to fit snugly with the receiver member 404, to match a contour of the bone surface, to reposition the hook with respect to the receiver member, and/or to adjust a height of the hook to accommodate receiver members of different heights or situations where the primary bone anchor 402 is over or under inserted into the bone.

Figure 4E:
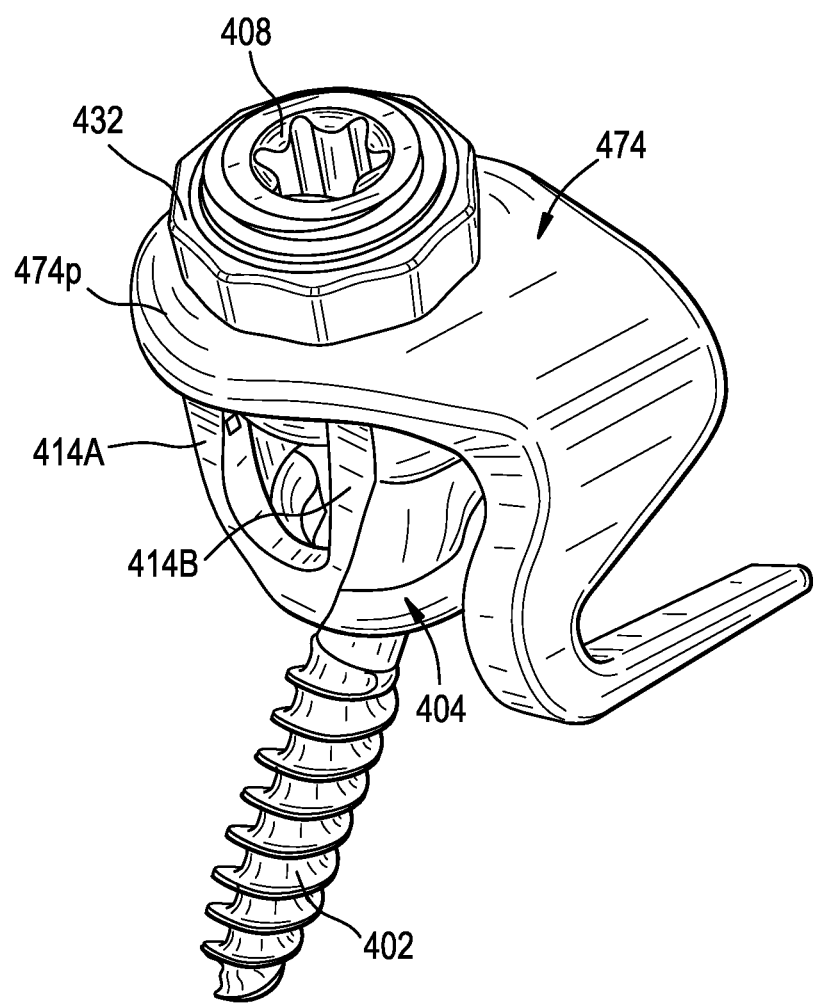
FIG. 4E is a perspective view of the bone anchor assembly of FIG. 4A shown with an alternate hook attachment.

As shown in FIG. 4E, instead of using a locking screw 478 and a collar 476 that wraps around the receiver member 404, the hook 474 can attach to the receiver member in a manner similar to that used to attach the wing 230 of FIGS. 2A-2M. In particular, the hook can include a proximal portion 474p that sits atop the opposed arms 414A, 414B of the receiver member 404 and that defines a central opening through which a closure mechanism 408 in the form of an extended threaded post is received. The hook 474 can be locked onto the closure mechanism 408 and the receiver member by a threaded nut 432.

The hook 474 can be attached to the receiver member 404 after the receiver member and the bone anchor 402 are coupled to the bone, which can advantageously give the surgeon more flexibility for insertion and also allow insertion of the bone anchor and receiver member with an unobstructed view. In addition, the hook 474 can be coupled to the receiver member 404 such that the bone anchor 402 does not restrict movement of the hook. The hook 474 can thus be positioned with respect to the bone anchor 402 at least with as many degrees of freedom as the receiver member 404.

As discussed above in the embodiment of FIGS. 2A-2M, supplemental fixation of a primary bone anchor in a bone anchor assembly can be accomplished using a wing or bracket having one or more bone anchor openings through which one or more auxiliary bone anchors can be driven into bone. In some instances, however, a surgeon may experience difficulty in making certain bone anchor placements having angular trajectories. Variability in the bony anatomy of the spine can make it difficult to position the distal portion of the wing in close proximity to bone to facilitate proper engagement or purchase with the anchor. A driver instrument used to drive an auxiliary anchor into bone can require more clearance to access the bone anchor opening of the wing.

To address such potential difficulties in supplemental fixation of auxiliary bone anchors, various embodiments of a bone anchor assembly are disclosed herein that include a wing or bracket having an angled distal portion. In some embodiments, the distal portion of the wing can be angled to the right or left of the spanning portion of the wing to facilitate bone anchor placements having a cephalad trajectory (i.e., towards a patient's head) and/or a caudal trajectory (i.e., towards a patient's feet). In some embodiments, the distal portion of the wing or bracket can, alternatively or additionally, be angled inward or outward to facilitate bone anchor placements having a medial trajectory (i.e., towards the middle of a patient) or a lateral trajectory (i.e., towards the side of a patient). Such angulation can facilitate improved engagement or purchase of the auxiliary anchor to bone and/or access by a driver instrument to the bone anchor opening of the wing.

Figure 5A:
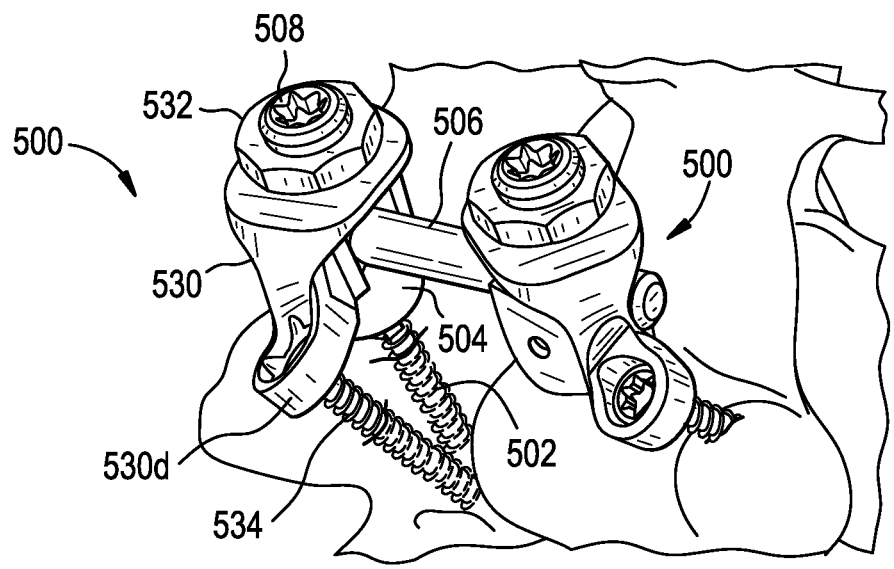
FIG. 5A is a perspective view of a bone anchor assembly and a spinal rod attached to a spine.
Figure 5B:
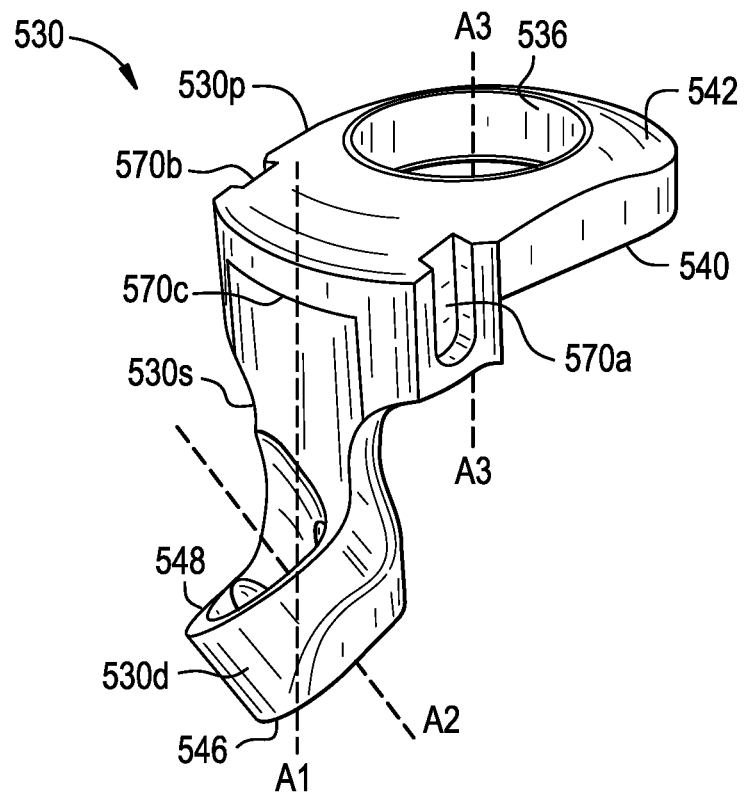
FIG. 5B is a perspective view of a wing of the bone anchor assembly of FIG. 5A.
Figure 5C:
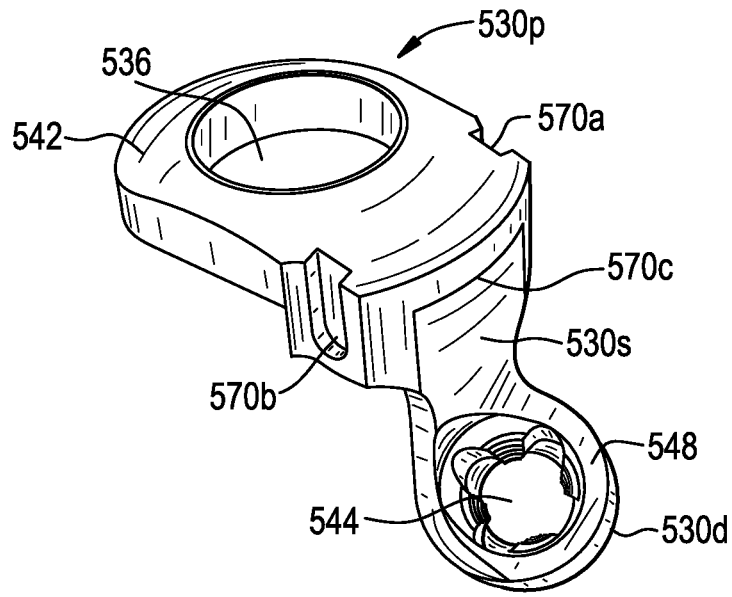
FIG. 5C is another perspective view of a wing of the bone anchor assembly of FIG. 5A.
Figure 5D:
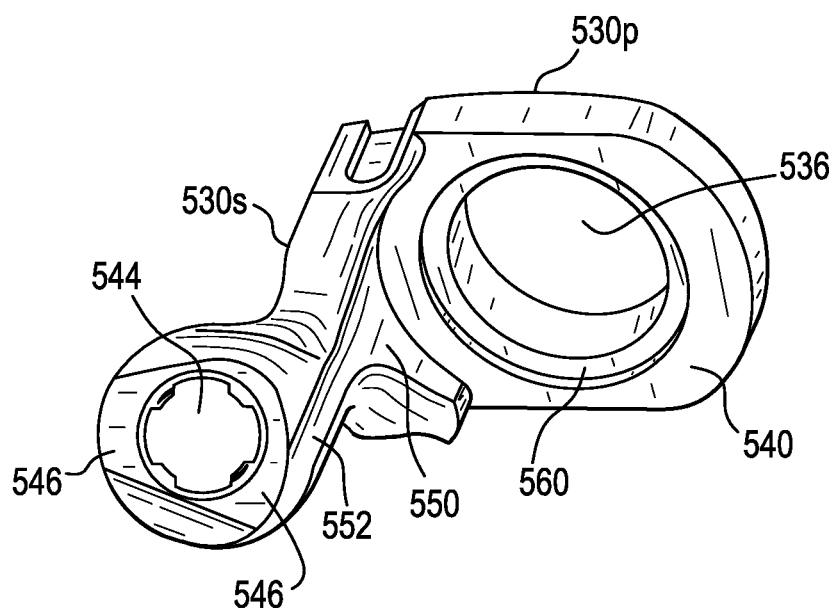
FIG. 5D is another perspective view of a wing of the bone anchor assembly of FIG. 5A.

FIGS. 5A through SI illustrate an exemplary embodiment of a bone anchor assembly 500 that includes a bracket or wing 530 having an angled distal portion 530d. When viewed from the perspective of FIG. 5A, the distal portion 530d is angled towards the right side of the wing 530. The bone anchor assembly 500 can include a bone anchor 502, a receiver member 504, a closure mechanism 508, a bracket or wing 530, a nut 532 and an auxiliary bone anchor 534. The wing 530 can be secured to the receiver member 504, e.g., using the closure mechanism 508 and nut 532, thereby providing the ability to augment fixation of the bone anchor 502 with the auxiliary bone anchor 534 having an angular trajectory. The closure mechanism 508 can be secured to the receiver member 504 to capture a spinal fixation element, e.g., a spinal rod 506, within the receiver member. Tightening or locking the closure mechanism 508 can be effective to fix the spinal rod 506 relative to the receiver member 504, and to fix an angular position of the bone anchor 502 relative to the receiver member 504.

Except as described below or as will be readily appreciated by one having ordinary skill in the art, the bone anchor 502, the receiver member 504, the closure mechanism 508, the nut 532, and the auxiliary bone anchor 534 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 500 can include any one or more of the features of the bone anchor assembly 200 and/or the bone anchor assembly 100 described above.

In the illustrated embodiment, the bracket or wing 530 can include a proximal portion 530p, an angled distal portion 530d, and a spanning portion 530s that connects the proximal portion to the distal portion of the wing. The proximal portion 530p of the wing 530 can extend horizontally from a proximal end of the spanning portion 530s of the wing 530. The proximal portion 530p can include a proximal-facing surface 540 and a distal-facing surface 542. The proximal-facing surface 540 of the proximal portion 530p of the wing 530 can be domed or rounded to provide an atraumatic surface and reduce the risk of tissue irritation post-implantation. The distal-facing surface 542 of the proximal portion 530p of the wing 530 can be configured to bear against a proximal terminal end or surface of the receiver member 504. The distal-facing surface 542 can form a negative or a substantial negative of the proximal terminal end or surface of the receiver member 504. For example, the proximal-facing surfaces of the arms of the receiver member 504 can be radially-convex, and the distal-facing surface 542 of the wing 530 can define a radially-concave channel (not shown) that receives the convex ends of the arms.

The proximal portion 530p of the wing 530 can define a central opening 536 that extends through the proximal-facing surface 540 and the distal-facing surface 542. The central opening 536 can be oriented such that the central axis of the opening A3 is perpendicular or substantially perpendicular to the distal-facing surface 542 of the proximal portion 530p of the wing 530. The central opening 536 can be sized so that the closure mechanism 508 can be inserted through the opening and extend at least partially above the proximal-facing surface 540 of the proximal portion 530p of the wing 530. The central opening 536 can include a smooth, non-threaded interior surface to allow the wing 530 and the closure mechanism 508 to be freely rotatable with respect to one another. The central opening 536 or another feature of the wing 530 can be sized and configured to snap onto or capture a portion of the closure mechanism 508 or a proximal surface of the receiver member 504. In the illustrated exemplary embodiment, a counter-bore 560 can be formed about the central opening 536 in the distal-facing surface 542 of the proximal portion 530p of the wing 530 to accommodate a radially extending shoulder portion of the closure mechanism 508 that may extend above the proximal terminal end of the receiver member 504. The structure and function of the counter-bore 560 is discussed in more detail with respect to FIG. 6A-6C.

The spanning portion 530s of the wing 530 can extend vertically in a proximal-distal direction to join the proximal portion 530p of the wing to the distal portion 530d of the wing. The spanning portion 530s of the wing 530 can be an elongated arm that extends distally from a side wall of the proximal portion 530p of the wing in a vertical or a substantially vertical plane. The spanning portion 530s of the wing 530 can have a lateral surface 550 that engages or faces a sidewall of the receiver member 504. The lateral surface 550 can form a negative of the sidewall of the receiver member 504, such that the spanning portion 530s of the wing 530 can hug the receiver member with minimal or zero gap there between. For example, the lateral surface 550 can be concave with a radius of curvature equal or substantially equal to a radius of curvature of the exterior sidewall of the receiver member 504. The proximal portion 530p, distal portion 530d, and spanning portion 530s can be formed integrally as a monolithic unit as shown, or one or more of said components can be separate and selectively attachable to the others. In some embodiments, a kit of modular components can be provided to allow selection of the components most appropriate for a given use. For example, a spanning portion 530s of appropriate height can be selected based on the distance between the proximal end of the receiver member 504 and the bone surface in a given application.

In some embodiments, the wing 530 can include various features of a unilateral locking interface, including but not limited to one or more grooves 570a, 570b, and surface projections 570c. The unilateral locking interface enables a surgical instrument that includes a unilateral locking mechanism (not shown) to rigidly hold onto one side of the wing 530. Exemplary unilateral locking interfaces that can be included in the wing 530 are disclosed in U.S. patent application Ser. No. 15/843,618, filed on Dec. 15, 2017 and entitled "Unilateral Implant Holders and Related Methods," the entire contents of which are hereby incorporated by reference.

The angled distal portion 530d of the wing 530 can extend outward from the distal end of the spanning portion 530s away from the receiver member 504. The degree to which the wing 530 extends outward from the receiver member 504 can vary among different embodiments. In the illustrated embodiment, the ratio of wing extension to rod diameter (or the ratio of wing extension to the width of the rod-receiving recess in the receiver member) is about 2:1. In some embodiments, this ratio can be less than about 10:1, less than about 5:1, less than about 3:1, less than about 2:1, less than about 1:1, and/or less than about 0.5:1. In some embodiments, the ratio can be about 10:1, about 5:1, about 3:1, about 2:1, about 1:1, or about 0.5:1.

Figure 5E:
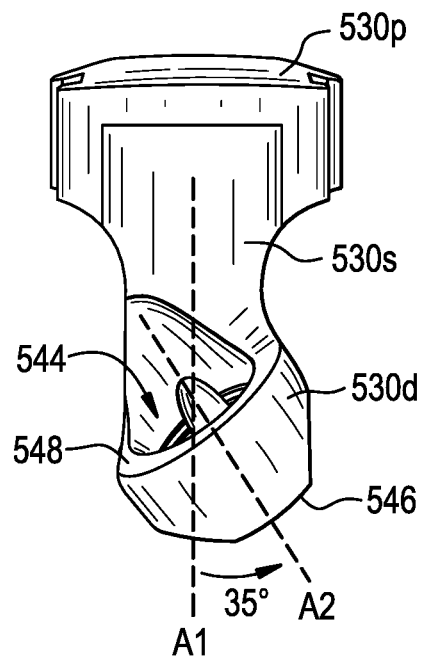
FIG. 5E is a side view of a wing of the bone anchor assembly of FIG. 5A.

When viewed from the perspective of FIG. 5E, the angled distal portion 530d is angled to the right of the vertically-disposed spanning portion 530s of the wing 530. As shown, the angled distal portion 530d includes a distal surface 546 and a proximal surface 548. The distal surface 546 and the proximal surface 548 can be oriented in parallel or substantially in parallel. The distal-facing surface 546 can include teeth, texturing, or other surface features to enhance grip with the adjacent bone. The distal portion 530d of the wing 530 can have a lateral surface 552 that abuts or faces a sidewall of the receiver member 504. The lateral surface 552 can form a negative of the sidewall of the receiver member 504, such that the distal-portion 530d of the wing 530 can hug the receiver member with minimal or zero gap there between. For example, the lateral surface 552 can be concave with a radius of curvature equal or substantially equal to a radius of curvature of the exterior sidewall of the receiver member 504.

The distal portion 530d of the wing 530 can define an opening 544 that extends through the proximal surface 548 and the distal surface 546 to receive an auxiliary bone anchor 534. The bone anchor opening 544 can be sized to insert a distal shaft of the auxiliary bone anchor 534 through the opening and to abut the proximal head of the auxiliary bone anchor when disposed therein. As shown in the illustrated embodiment, the bone anchor opening 544 can be oriented perpendicular or substantially perpendicular to the distal surface 546 of the wing 530. In other arrangements, the nominal or central axis of the bone anchor opening can be obliquely angled relative to the distal surface 546 and/or the proximal surface 548. The distal surface 546 of the wing 530 and/or the proximal surface 548 of the wing can be obliquely angled relative to a vertical or proximal-distal axis of the wing. For example, as shown, the distal surface 546 is angled to face to the right of the vertically-disposed spanning portion 530s. In such embodiments, the central axis A2 of the bone anchor opening 544 can extend at an oblique angle, down and to the right, with respect to a proximal-distal axis A1 of the spanning portion 530s of the wing. This arrangement can facilitate various bone anchor placements in which the distal end of the auxiliary bone anchor is to the right of the spanning portion 530s of the wing when viewed from the perspective of FIG. 5A.

For example, as shown in FIG. 5A, such bone anchor placements can include ones in which the wing 530 is disposed laterally to a spinal rod 506 and in which the auxiliary bone anchor 534 is driven through the bone anchor opening 544 with a cephalad trajectory (i.e., towards a patient's head). This orientation can allow the auxiliary bone anchor 534 to remain wholly within the same vertebral level as the primary bone anchor 502, for example within a lateral mass of the vertebra. It will be appreciated that the wing 530 can be flipped around to be positioned on the other side of the illustrated rod 506 (e.g., on a medial side of the rod), or to be positioned laterally to a contralateral spinal rod (not shown). In these cases, the positioning of the wing 530 can facilitate bone anchor placements in which the auxiliary bone anchor 534 can be driven through the bone anchor opening 544 with a caudal trajectory (i.e., towards a patient's feet). In some embodiments, as discussed further below with respect to FIG. 7A, a caudal trajectory can allow for fixation of the auxiliary bone screw 534 into multiple cortical bone layers, e.g., at least two, at least three, or more. The angled distal portion 530d can allow for the above described bone anchor placements while maintaining the distal surface 546 of the wing 530 in contact with or in close proximity to the bone surface (e.g., within 0 to 3 mm).

In some embodiments, depending on the requirements of the particular application, the distal surface 546 of the wing 530 can be obliquely angled to fix the central axis A2 of the bone anchor opening 544 at any oblique angle to the right of the spanning portion 530s of the wing 530. For example, as shown in FIG. 5E, the distal surface 546 of the distal portion 530d of the wing 530 can be obliquely angled, such that the central axis A2 of the bone anchor opening 544 extends at an angle of 35 degrees to the right of the proximal-distal axis A1 of the spanning portion 530s of the wing 530. Thus, an auxiliary bone anchor 534 can be readily disposed in the bone anchor opening 544 with the distal shaft of the anchor having an angular trajectory coaxial with, or within a defined cone of angulation with respect to, the central axis A2 of the bone anchor opening 544 to the right of the spanning portion 530s. In some embodiments, the distal surface 546 of the wing 530 can be obliquely angled, such that the central axis A2 of the bone anchor opening 544 can extend at an angle between 15 to 45 degrees inclusive to the right of the proximal-distal axis A1 of the spanning portion 530s.

Figure 5F:
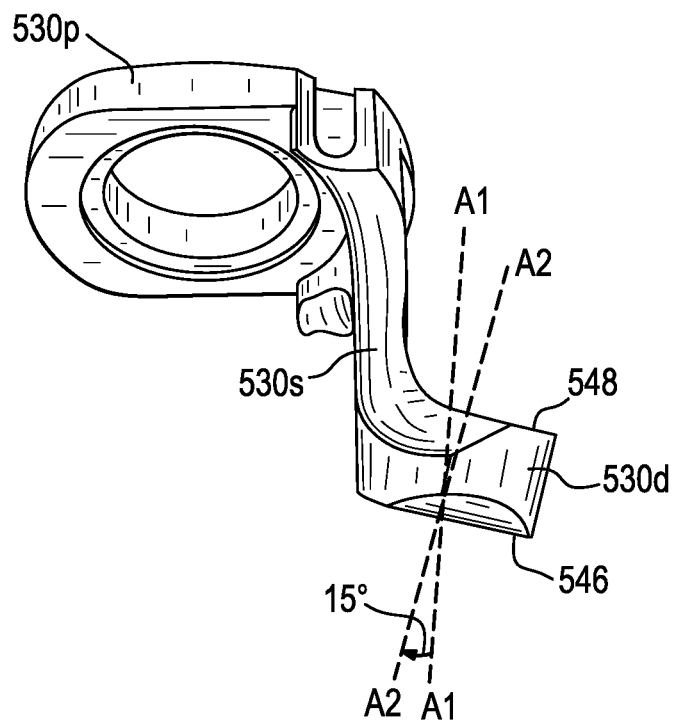
FIG. 5F is another perspective view of a wing of the bone anchor assembly of FIG. 5A.

In some embodiments, the distal surface 546 of the wing 530 can be further angled to face inward or outward with respect to the vertically-disposed spanning portion 530s of the wing 530. By angling the distal surface 546 inward or outward, the distal portion 530d can facilitate auxiliary bone anchor placements through the bone anchor opening 544 having a medial or lateral trajectory component in addition to or instead of a cephalad or caudal trajectory component. In some embodiments, angling the distal surface 546 inward or outward can facilitate bone anchor placements in which the auxiliary bone anchor 534 is secured within the lateral mass of a vertebra. In some embodiments, angling the distal surface 546 of the wing 530 inward or outward can provide clearance for a driver instrument on the proximal surface 548 side of the distal portion 530d of the wing 530 to access the bone anchor opening 544. In some embodiments, based on the requirements of the particular application, the distal surface 546 of the wing 530 can be obliquely angled inward or outward to fix the central axis A2 of the bone anchor opening 544 at any medial or lateral angle with respect to a proximal-distal axis A1 of the spanning portion 530s of the wing 530. For example, as shown in FIG. 5F, the distal surface 546 of the distal portion 530d of the wing 530 can be angled to face inward towards the spanning portion 530s of the wing 530, such that the central axis A2 of the bone anchor opening 544 extends inward at a medial angle of 15 degrees with respect to the proximal-distal axis A1 of the spanning portion 530s. Thus, an auxiliary bone anchor 534 can be readily disposed in the bone anchor opening 544 with the distal shaft of the anchor having a medial trajectory coaxial with, or within a defined cone of angulation with respect to, the central axis A2 of the bone anchor opening 544. In some embodiments, the distal surface 546 of the distal portion 530d of the wing 530 can be obliquely angled, such that the central axis A2 of the bone anchor opening 544 can extend at a medial angle between 5 to 20 degrees inclusive.

Figure 5G:
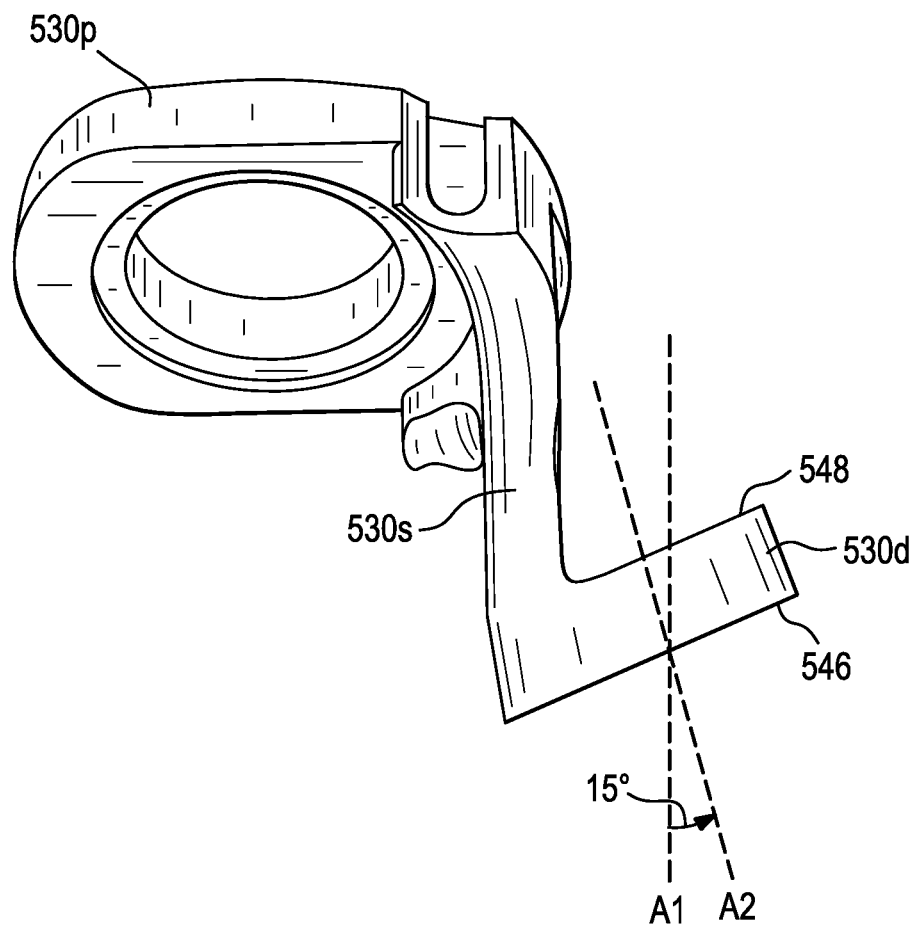
FIG. 5G is another perspective view of a wing of the bone anchor assembly of FIG. 5A.

Alternatively, as shown in FIG. 5G, the distal surface 546 of the distal portion 530d of the wing 530 can be angled to face outward away from the spanning portion 530s, such that the central axis A2 of the bone anchor opening 544 extends outward at a lateral angle of 15 degrees with respect to the proximal-distal axis A1 of the spanning portion 530s of the wing 530. Thus, an auxiliary bone anchor 534 can be readily disposed in the bone anchor opening 544 with the distal shaft of the anchor having a lateral trajectory coaxial with, or within a defined cone of angulation with respect to, the central axis A2 of the bone anchor opening 544. In some embodiments, the distal surface 546 of the distal portion 530d of the wing 530 can be obliquely angled, such that the central axis A2 of the bone anchor opening 544 can extend at a lateral angle between 5 to 20 degrees inclusive. Such embodiments can be useful to accommodate the bony anatomy of the lumbar spine.

Figure 5H:
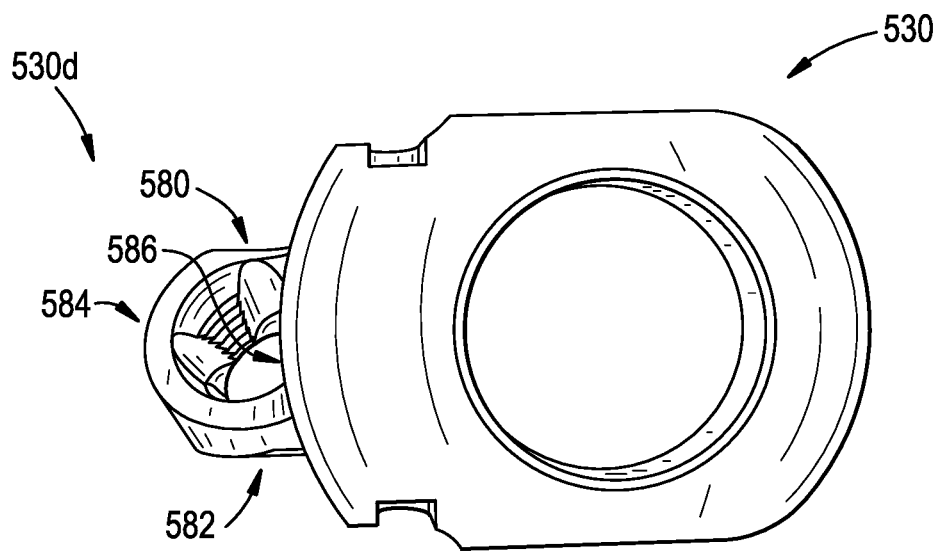
FIG. 5H is a top view of a wing of the bone anchor assembly of FIG. 5A with the angled distal portion facing in a caudal direction.

FIG. 5H is a top view of the wing 530 of the bone anchor assembly of FIG. 5A with the angled distal portion 530d facing in a caudal direction. As shown in FIG. 5H, from a posterior viewpoint, the wing 530 can be positioned with the angled distal portion 530d extending laterally relative to the left of the spinal midline and thus facing in a caudal direction. In this exemplary caudal configuration, the angled distal portion 530d of the wing 530 has a superior end 580, an inferior end 582, a free lateral end 584 extending between the superior and inferior ends, and a medial end 586 extending between the superior and inferior ends. With the angled distal portion 530d facing caudally, the superior end 580 of the distal portion 530d is more distal (or lower) than the inferior end 582, such that the distal surface 546 faces in the caudal direction. In some embodiments, when the distal portion 530d is also angled medially (e.g., as discussed above in FIG. 5F), the superior end 580 of the distal portion 530d is more distal than the inferior end 582 and the free lateral end 584 is more distal than the medial end, such that the distal surface 546 faces in both caudal and medial directions. In some embodiments, when the distal portion 530d is also angled laterally (e.g., as discussed above in FIG. 5G), the superior end 580 of the distal portion 530d is more distal than the inferior end 582 and the medial end 586 is more distal than the free lateral end 584, such that the distal surface 546 faces in both caudal and lateral directions.

Figure 5I:
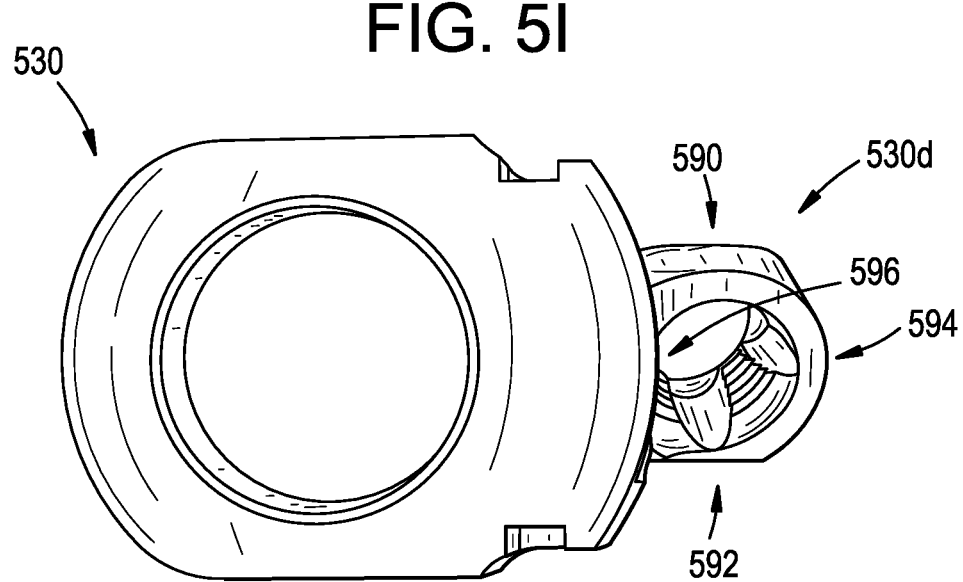
FIG. 5I is a top view of a wing of the bone anchor assembly of FIG. 5A with the angled distal portion facing in a cephalad direction.

FIG. 5I is a top view of the wing 530 of the bone anchor assembly of FIG. 5A with the angled distal portion 530d facing in a cephalad direction. As shown in FIG. 5I, from a posterior viewpoint, the wing 530 can be positioned with the distal portion 530d extending laterally relative to the right of the spinal midline and thus facing in a cephalad direction. In this exemplary cephalad configuration, the angled distal portion 530d of the wing 530 has a superior end 590, an inferior end 592, a free lateral end 594 extending between the superior and inferior ends, and a medial end 596 extending between the superior and inferior ends. With the distal portion 530d facing cephalically, the inferior end 592 of the distal portion 530d is more distal (or lower) than the superior end 590, such that the distal surface 546 faces in a cephalad direction. In some embodiments, when the distal portion 530d is also angled medially (e.g., as discussed above in FIG. 5F), the inferior end 592 of the distal portion 530d is more distal (or lower) than the superior end 590 and the free lateral end 594 is more distal than the medial end 596, such that the distal surface 546 faces in both cephalad and medial directions. In some embodiments, when the distal portion 530d is also angled laterally (e.g., as discussed above in FIG. 5G), the inferior end 592 of the distal portion 530d is more distal (or lower) than the superior end 590 and the medial end 596 is more distal than the free lateral end 594, such that the distal surface 546 faces in both cephalad and lateral directions.

In some embodiments, the bone anchor opening 544 can include any of a number of features for accepting bone anchors 534 at varying angles. For example, as discussed above with respect to FIG. 2A-2M, the bone anchor opening 544 can be at least partially threaded to receive a variable-angle locking screw having a threaded proximal head. As shown, the opening 544 can have a plurality of columns of threads spaced apart to define a plurality of non-threaded recesses. In the illustrated embodiment, the opening 544 has four columns of threads. The columns of threads can be arranged around the inner surface of the opening 544 for engaging threads on the head of a locking auxiliary bone anchor and/or a variable-angle locking auxiliary bone anchor. The auxiliary bone anchor 534 can thus be locked with the wing 530 coaxially with the central axis A2 of the opening 544 or at a selected angle within a range of selectable angles relative to the central axis A2 of the opening 544. The auxiliary bone anchor 534 can include features to facilitate this variable-angle locking, such as a proximal head that is at least partially spherical having a thread with a profile that follows the arc-shaped radius of curvature of the spherical portion of the head. The variable-angle capability of the screw/opening interface can allow the user to place a locking auxiliary bone anchor into the bone at any angle within defined angulation limits. In some embodiments, the interior surface of the opening 544 can be smooth or spherical, without threads or locking features.

In some embodiments, the proximal-most extent of each auxiliary bone anchor 534 can be distal to the spinal rod 506. In other embodiments, the proximal-most extent of each auxiliary bone anchor 534 can be distal to the distal-most extent of the receiver member 504. These configurations can advantageously reduce the overall profile of the assembly 500. The wing 500 can be Z-shaped or substantially Z-shaped. While one bone anchor opening 544 is shown in the illustrated embodiment, it will be appreciated that the wing 530 can include any number of bone anchor openings (e.g., one, two, three, four, five, and so on).

Figure 6A:
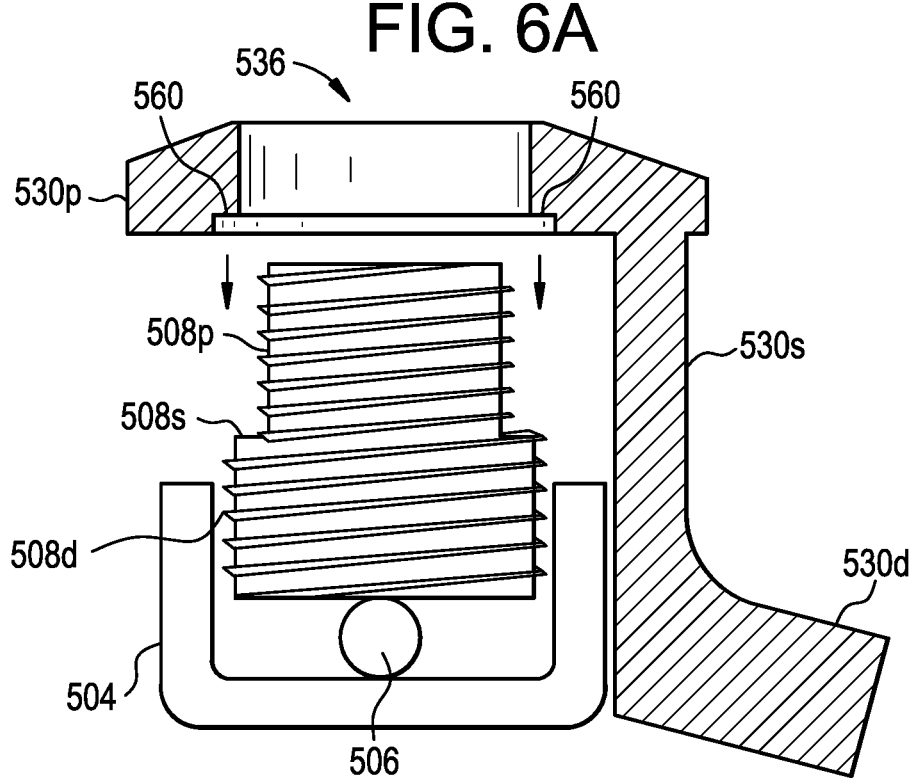
FIG. 6A is a cross sectional view of a wing of the bone anchor assembly of FIG. 5A prior to being secured to a closure mechanism.
Figure 6B:
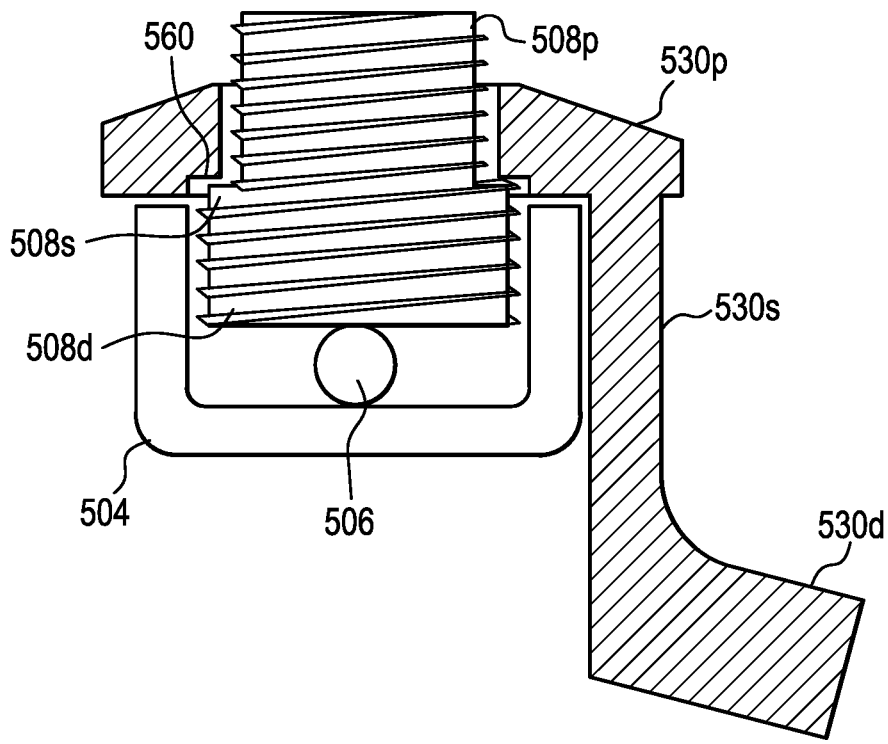
FIG. 6B is a cross sectional view of the wing of FIG. 6A secured to a closure mechanism.
Figure 6C:
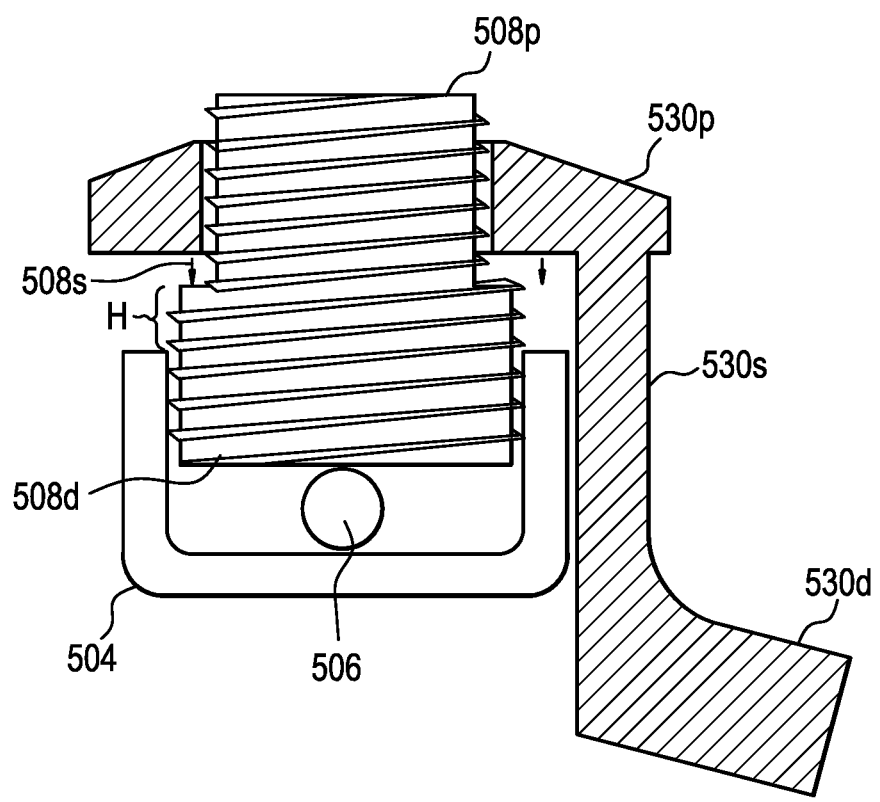
FIG. 6C is another cross sectional view of the wing of FIG. 6A secured to a closure mechanism.

FIG. 6A-6C are cross-sectional views illustrating the wing or bracket 530 secured to the bone anchor assembly 500 of FIG. 5A-5H. As discussed above, the proximal portion 530p of the wing can include a distal-facing surface 542 configured to bear against a proximal terminal end or surface of the receiver member 504 when the wing 530 is secured to the receiver member. For example, in some embodiments, the closure mechanism 508 can be in the form of a threaded post having an enlarged-diameter distal portion 508d and a reduced-diameter proximal portion 508p. The distal portion 508d of the closure mechanism 508 can be threaded into the receiver member 504 to engage a spinal rod 506 disposed in the receiver member. The proximal portion 508p of the closure mechanism 508 can protrude above the receiver member 504, e.g., above a proximal-facing terminal end or surface of the receiver member, and through the opening 536 formed in the wing.

However, there can be instances when the distal portion 508d of the closure mechanism 508 may not be fully threaded into the receiver member 504, which can cause the radially-extending shoulder portion 508s of the closure mechanism 508 to protrude above the proximal end of the receiver member 504. In such instances, the shoulder portion 508s of the closure mechanism 508 can abut the proximal portion 530p of the wing 530 distal-facing surface 542 of the wing and thereby prevent the proximal portion 530p from bearing against the receiver member 504. This can cause less reliable and/or inconsistent tightening of the wing 530 to the bone anchor assembly 500.

As shown in the illustrated embodiment of FIGS. 6A and 6B, a counter bore 560 can be formed about the opening 536 in the distal-facing surface 542 of the proximal portion 530p to secure the wing 530 to the bone anchor assembly 500 more consistently. The counter bore 560 can be an annular ring or channel formed around the opening 536. The counter bore 560 can be sized to accommodate the width of the shoulder portion 508s. The depth or height of the counter bore 560 can be configured to at least partially receive the shoulder portion 508s that protrudes above the receiver member 504 in order to maintain contact between the proximal portion 530p of the wing 530 and the proximal-facing surface of the receiver member 504. The depth or height of the counter bore 560 can be configured not to exceed a threshold depth or height at which the closure mechanism can become disengaged from the spinal rod and thus compromise fixation of the rod 506 within the receiver member 504. Embodiments including a counterbore can provide more reliable and/or consistent tightening by ensuring that the wing is always tightened to the receiver member, regardless of the vertical position of the closure mechanism.

Alternatively or additionally, as shown in the illustrated embodiment of FIG. 6C, the closure mechanism 508 can be sized such that the radially-extending shoulder portion 508s is configured to always extend above the receiver member 504. In such embodiments, the distal-facing surface 542 of the proximal portion 530d of the wing 530 bears against the radially-extending shoulder portion 508s of the closure mechanism 508 instead of the receiver member 504. For example, as shown in FIG. 6C, the enlarged-diameter distal portion 508d of the closure mechanism 508 can be configured with an extended height H that allows the shoulder portion 508s of the closure mechanism 508 to protrude above the receiver member 504 when in contact with the spinal rod 506. Such embodiments can provide a more reliable and/or consistent tightening of the wing 530 by ensuring that the wing is always tightened to the closure mechanism, regardless of the vertical position of the closure mechanism.

As discussed above, some embodiments of the bone anchor assembly can include a wing having a distal portion angled to the left of the vertically-disposed wing. In such embodiments, an auxiliary bone anchor can be disposed through an opening in the distal portion with caudal or cephalad trajectories similar to those facilitated by the wing 530 of the bone anchor assembly 500 when implanted on the opposite side of the patient's spine (i.e., the left hand side of the patient).

FIGS. 7A through 7F illustrate an exemplary embodiment of a bone anchor assembly 700 that includes a bracket or wing 730 having an angled distal portion 730d. As shown, the bone anchor assembly 700 includes a bone anchor 502, a receiver member 504, a closure mechanism 508, a bracket or wing 730, a nut 532 and an auxiliary bone anchor 534. Except as described below or as will be readily appreciated by one having ordinary skill in the art, the bone anchor 502, the receiver member 504, the closure mechanism 508, the nut 532, and the auxiliary bone anchor 534 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 500 can include any one or more of the features of the bone anchor assembly 200 and/or the bone anchor assembly 100 described above.

As shown in FIGS. 7A through 7F, the bracket or wing 730 can include a proximal portion 730p, an angled distal portion 730d, and a spanning portion 730s that connects the proximal portion to the distal portion of the wing. Except as described below or as will be readily appreciated by one having ordinary skill in the art, the proximal portion 730p and the spanning portion 730s of the wing 730 are substantially similar to the proximal portion 530p and the spanning portion 530s of the wing 530 described above with respect to FIGS. 5A-5I and FIGS. 6A-6C. A detailed description of the structure and function thereof is thus omitted here for the sake of brevity. The wing 730 can include any one or more of the features of the wing 500 described above.

Figure 7A:
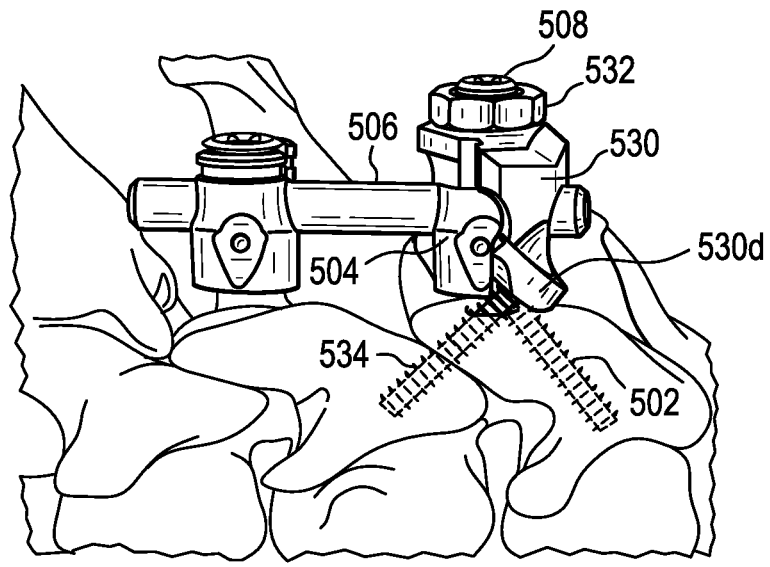
FIG. 7A is a perspective view of a bone anchor assembly and a spinal rod attached to a spine.
Figure 7B:
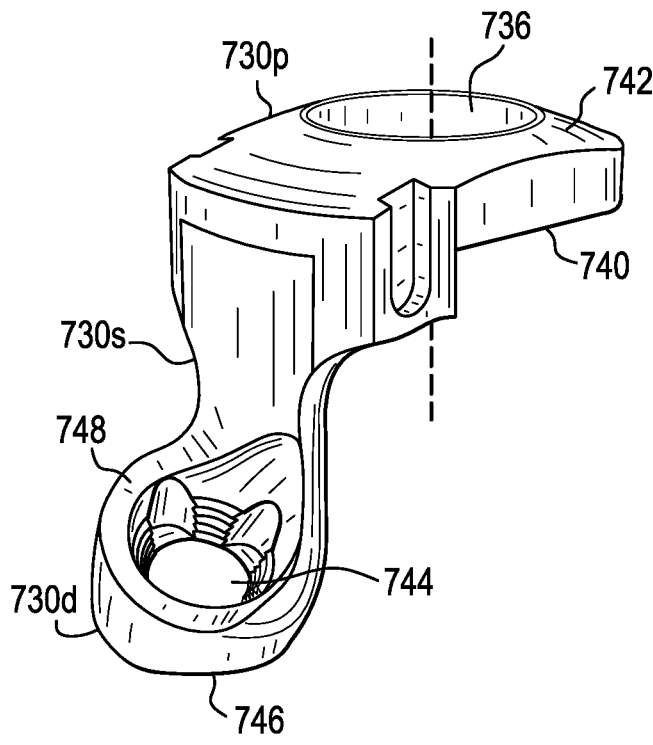
FIG. 7B is a perspective view of a wing of the bone anchor assembly of FIG. 7A.
Figure 7C:
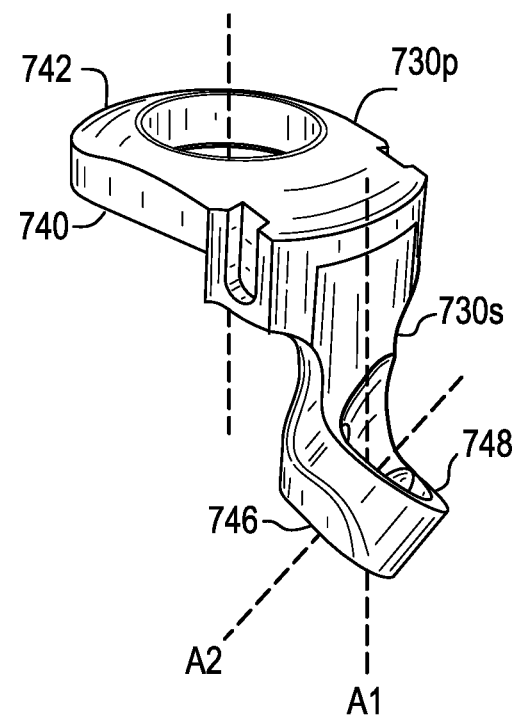
FIG. 7C is another perspective view of a wing of the bone anchor assembly of FIG. 7A.
Figure 7D:
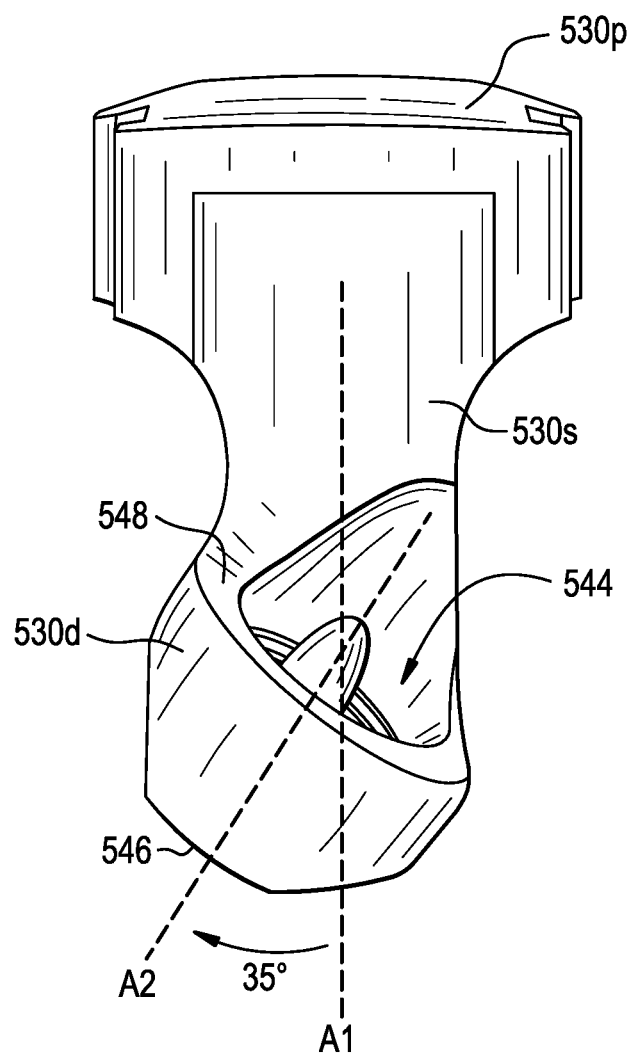
FIG. 7D is a side view of a wing of the bone anchor assembly of FIG. 7A.

In the illustrated embodiment, the distal portion 730d of the wing 730 is substantially similar to the distal portion 530d of the wing 500, except that the distal portion 730d is angled to the left of the vertically-disposed spanning portion 730s (when viewed from the perspective of FIG. 7D). As shown, the angled distal portion 730d can include a distal surface 746 and a proximal surface 748 that can be oriented in parallel or substantially in parallel. The distal portion 730d of the wing 730 can define an opening 744 that extends through the proximal surface 748 and the distal surface 746 to receive an auxiliary bone anchor 534. As shown in the illustrated embodiment, the bone anchor opening 744 can be oriented perpendicular or substantially perpendicular to the distal surface 746 of the wing 730. In other arrangements, the nominal or central axis of the bone anchor opening can be obliquely angled relative to the distal surface 746 and/or the proximal surface 748. The distal surface 746 of the wing 730 and/or the proximal surface 748 of the wing can be obliquely angled relative to a vertical or proximal-distal axis of the wing. For example, as shown, the distal surface 546 is angled to face to the left of the vertically-disposed spanning portion 730s. In such embodiments, the central axis A2 of the bone anchor opening 744 can extend at an oblique angle, down and to the left, with respect to the proximal-distal axis A1 of the spanning portion 730s of the wing. This arrangement can facilitate various bone anchor placements in which the distal end of the auxiliary bone anchor is to the left of the spanning portion 530s of the wing when viewed from the perspective of FIG. 7A.

For example, as shown in FIG. 7A, such bone anchor placements can include ones in which the wing 730 is disposed laterally to a spinal rod 506 and in which the auxiliary bone anchor 534 is driven through the bone anchor opening 744 with a caudal trajectory (i.e., towards a patient's feet). This orientation can allow the auxiliary bone anchor 534 to extend into one or more adjacent vertebral levels, e.g., across a facet joint. A caudal trajectory can allow for fixation of the auxiliary bone screw 534 into multiple cortical bone layers, e.g., at least two, at least three, or more. For example, as shown in FIG. 7A, with the primary bone anchor 502 positioned in a superior vertebral level, the bone anchor assembly 700 can effect tri-cortical fixation with the auxiliary bone anchor 534 crossing a facet joint between the superior vertebral level and an adjacent inferior vertebral level. It will be appreciated that the wing 730 can be flipped around to be positioned on the other side of the illustrated rod 506 (e.g., on a medial side of the rod), or to be positioned laterally to a contralateral spinal rod (not shown). In these cases, the positioning of the wing 530 can facilitate bone anchor placements in which the auxiliary bone anchor 534 can be driven through the bone anchor opening 744 with a cephalad trajectory (i.e., towards a patient's head). As discussed above with respect to FIG. 5A, a cephalad trajectory can allow the auxiliary bone anchor 534 to remain wholly within the same vertebral level as the primary bone anchor 502, for example within a lateral mass of the vertebra. The angled distal portion 730d can allow for the above-described bone anchor placements while maintaining the distal surface 746 of the wing 730 in contact with or in close proximity to the bone surface (e.g., within 0 to 3 mm).

In some embodiments, depending on the requirements of the particular application, the distal surface 746 of the wing 730 can be obliquely angled to fix the central axis A2 of the bone anchor opening 744 at any oblique angle to the left of the spanning portion 730s of the wing 730. For example, as shown in FIG. 7D, the distal surface 746 of the distal portion 730d of the wing 730 can be obliquely angled, such that the central axis A2 of the bone anchor opening 744 extends at an angle of 35 degrees to the left of the proximal-distal axis A1 of the spanning portion 730s of the wing 730. Thus, an auxiliary bone anchor 534 can be readily disposed in the bone anchor opening 744 with the distal shaft of the anchor having an angular trajectory coaxial with, or within a defined cone of angulation with respect to, the central axis A2 of the bone anchor opening 744 to the left of the spanning portion 730s. In some embodiments, the distal surface 746 of the wing 730 can be obliquely angled, such that the central axis A2 of the bone anchor opening 744 can extend at an angle between 15 to 45 degrees inclusive to the left of the proximal-distal axis A1 of the spanning portion 730s.

As discussed above with respect to FIGS. 5F and 5G, in some embodiments, the distal surface 746 of the wing 730 can be further angled to face inward or outward with respect to the vertically-disposed spanning portion 730s of the wing 730. In some embodiments, based on the requirements of the particular application, the distal surface 746 of the wing 730 can be obliquely angled inward or outward to fix the central axis A2 of the bone anchor opening 744 at any medial or lateral angle between 5 and 20 degrees inclusive with respect to a proximal-distal axis A1 of the spanning portion 730s of the wing 730. Thus, by angling the distal surface 746 inward or outward, the distal portion 730d can facilitate placement of the auxiliary bone anchor 534 having a medial or lateral trajectory component in addition to or instead of a cephalad or caudal trajectory component through the bone anchor opening 744. In some embodiments, angling the distal surface 746 inward or outward can facilitate bone anchor placements in which the auxiliary bone anchor 534 is secured within the lateral mass of a vertebra. In some embodiments, angling the distal surface 746 of the wing 730 inward or outward can provide clearance for a driver instrument on the proximal surface 748 side of the distal portion 730d of the wing 730 to access the bone anchor opening 744.

Figure 7E:
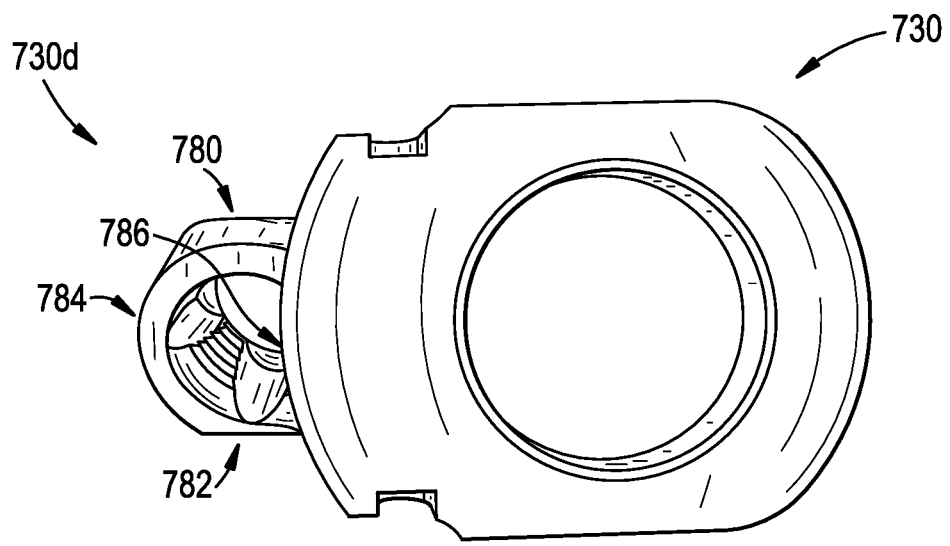
FIG. 7E is a top view of a wing of the bone anchor assembly of FIG. 7A with the angled distal portion facing in a cephalad direction.

FIG. 7E is a top view of the wing 730 of the bone anchor assembly of FIG. 7A with the angled distal portion 730d facing in a cephalad direction. As shown in FIG. 7E, from a posterior viewpoint, the wing 730 can be positioned with the distal portion 730d extending laterally relative to the left of the spinal midline and thus facing in a cephalad direction. In this exemplary cephalad configuration, the angled distal portion 730d of the wing 730 has a superior end 780, an inferior end 782, a free lateral end 784 extending between the superior and inferior ends, and a medial end 786 extending between the superior and inferior ends. With the distal portion 730d facing cephalically, the inferior end 782 of the distal portion 730d is more distal (or lower) than the superior end 780, such that the distal surface 746 faces in a cephalad direction. In some embodiments, when the distal portion 730d is also angled medially (e.g., as discussed above in FIG. 5G), the inferior end 782 of the distal portion 730d is more distal (or lower) than the superior end 780 and the free lateral end 784 is more distal than the medial end 786, such that the distal surface 746 faces in both cephalad and medial directions. In some embodiments, when the distal portion 730d is also angled laterally (e.g., as discussed above in FIG. 5H), the inferior end 782 of the distal portion 730d is more distal (or lower) than the superior end 780 and the medial end 786 is more distal than the free lateral end 784, such that the distal surface 746 faces in both cephalad and lateral directions.

Figure 7F:
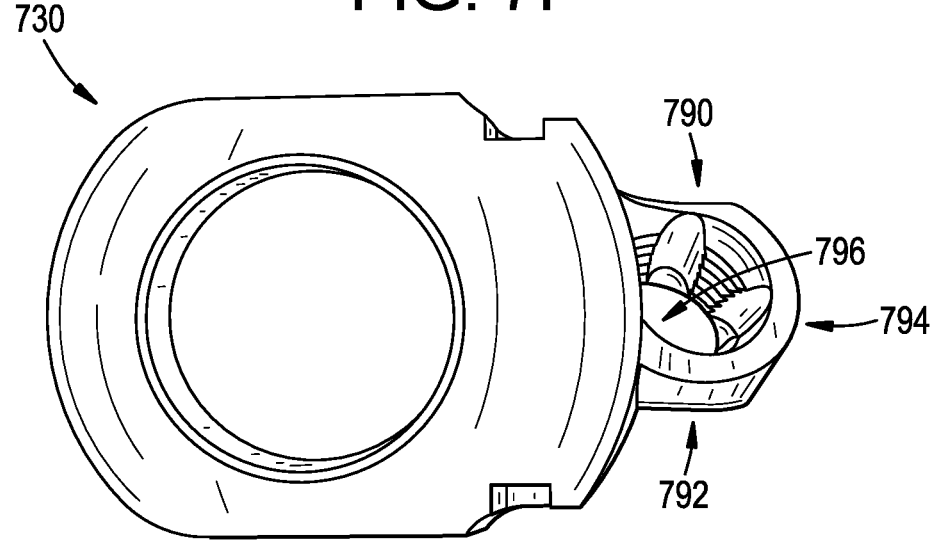
FIG. 7F is a top view of a wing of the bone anchor assembly of FIG. 7A with the angled distal portion facing in a caudal direction.

FIG. 7F is a top view of the wing 730 of the bone anchor assembly of FIG. 7A with the angled distal portion 730d facing in a caudal direction. As shown in FIG. 7F, from a posterior viewpoint, the wing 730 can be positioned with the angled distal portion 730d extending laterally relative to the right of the spinal midline and thus facing in a caudal direction. In this exemplary caudal configuration, the angled distal portion 730d of the wing 730 has a superior end 790, an inferior end 792, a free lateral end 794 extending between the superior and inferior ends, and a medial end 796 extending between the superior and inferior ends. With the angled distal portion 730d facing caudally, the superior end 790 of the distal portion 730d is more distal (or lower) than the inferior end 792, such that the distal surface 746 faces in the caudal direction. In some embodiments, when the distal portion 730d is also angled medially (e.g., as discussed above in FIG. 5G), the superior end 790 of the distal portion 730d is more distal than the inferior end 792 and the free lateral end 794 is more distal than the medial end 796, such that the distal surface 746 faces in both caudal and medial directions. In some embodiments, when the distal portion 730d is also angled laterally (e.g., as discussed above in FIG. 5H), the superior end 790 of the distal portion 730d is more distal than the inferior end 792 and the medial end 796 is more distal than the free lateral end 794, such that the distal surface 746 faces in both caudal and lateral directions.

As discussed above, some embodiments of the bone anchor assembly can include a wing having a distal portion angled inward or outward with respect to the vertically-disposed spanning portion without any right or left angulation. In such embodiments, an auxiliary bone anchor can be readily disposed through a bone anchor opening in the distal portion with a medial trajectory or a lateral trajectory.

FIGS. 8A through 8E illustrate an exemplary embodiment of a bracket or wing 830 of a bone anchor assembly having an angled distal portion 830d. As shown, the bracket or wing 830 can include a proximal portion 830p, an angled distal portion 830d, and a spanning portion 830s that connects the proximal portion to the distal portion. The angled distal portion 830d has a free lateral end 850 and a medial end 852. Except as described below or as will be readily appreciated by one having ordinary skill in the art, the proximal portion 830p and the spanning portion 830s of the wing 830 are substantially similar to the proximal and spanning portions of the wing 200, 500, and/or 700 described above with respect to FIGS. 2A-2M, 5A-5I, and 7A-7F. A detailed description of the structure and function thereof is thus omitted here for the sake of brevity. The wing 830 include any one or more of the features of the wings 200, 500 and/or 700 described above.

In the illustrated embodiment, the distal portion 830d of the wing 830 is substantially similar to the angled distal portions 530d, 730d disclosed above with respect to FIGS. 5A-5I and 7A-7F, except that the distal portion 830d is angled inward towards the vertically-disposed spanning portion 830s without angulation to the right or left of the wing 830s. The angled distal portion 830d of the wing 830 includes a distal surface 846 and a proximal surface 848. The distal surface 846 and the proximal surface 848 can be tilted down in parallel or substantially in parallel. When the distal portion 830d is angled inward (or medially when viewed from the perspective of FIG. 8B), the free lateral end 850 is more distal than the medial end 852, such that the distal surface 846 faces in a medial direction.

The distal portion 830d of the wing 830 can define one or more openings 844 that extend through the proximal surface 848 and the distal surface 846 to receive an auxiliary bone anchor 534. As shown in the illustrated embodiment, the bone anchor openings 844 can be oriented perpendicular or substantially perpendicular to the distal surface 846 of the wing 830. The distal surface 846 of the wing 830 can be obliquely angled to face inward towards the vertically-disposed spanning portion 830s of the wing 830 to fix the central axis A2 of the bone anchor opening 844 at a medial angle with respect to the proximal-distal axis A1 of the spanning portion 830s. Thus, an auxiliary bone anchor 534 can be readily disposed in the bone anchor opening 844 with the distal shaft of the auxiliary bone anchor 534 having a medial trajectory coaxial with, or within a defined cone of angulation with respect to, central axis A2 of the bone anchor opening.

Figure 8A:
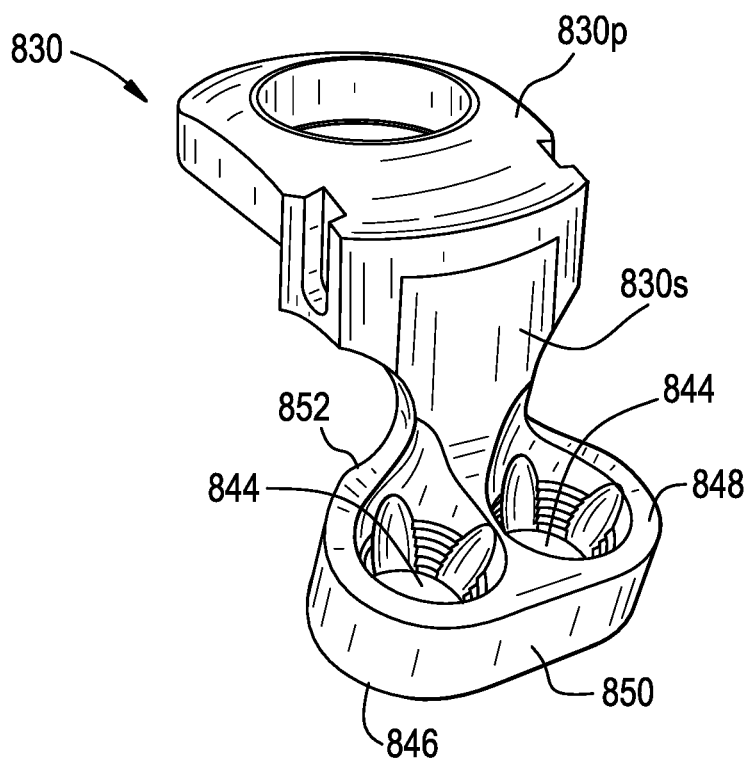
FIG. 8A is a perspective view of a wing of bone anchor assembly.
Figure 8B:
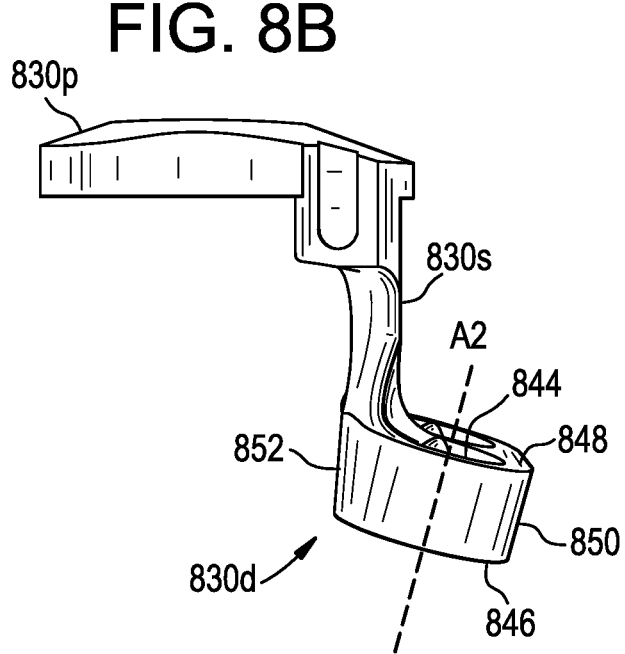
FIG. 8B is a side view of the wing of FIG. 8A.
Figure 8C:
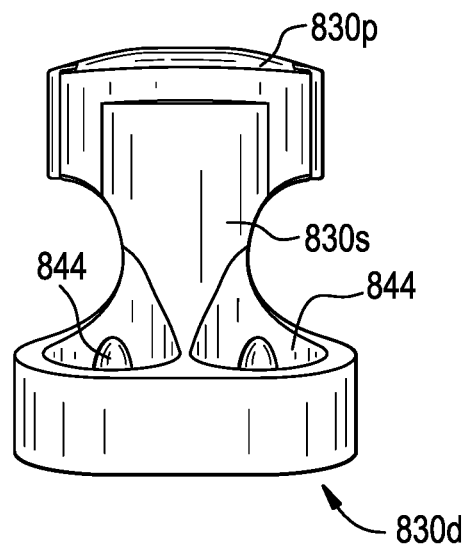
FIG. 8C is another side view of the wing of FIG. 8A.
Figure 8D:
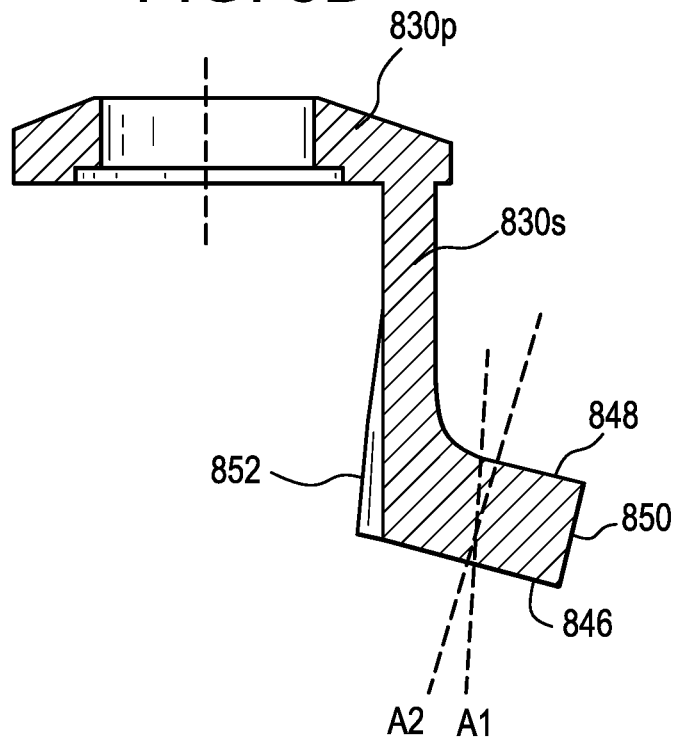
FIG. 8D is a sectional side view of the wing of FIG. 8A.

For example, in the illustrated embodiment of FIG. 8D, the distal surface 846 of the distal portion 830d of the wing 830 can be angled to face inward towards the spanning portion 830s, such that the central axis A2 of the bone anchor opening 844 extends inward at an angle of 15 degrees with respect to the proximal-distal axis A1. Thus, the auxiliary bone anchor 534 can be readily disposed in the bone anchor opening 844 with the distal shaft of the anchor having an medial trajectory of 15 degrees with respect to the proximal-distal axis A1. In some embodiments, the distal surface 846 of the distal portion 830d of the wing 830 can be obliquely angled to fix the central axis A2 of the bone anchor opening 844 at a medial angle between 5 to 20 degrees inclusive with respect to the proximal-distal axis A1 of the spanning portion 830s of the wing 830. In such embodiments, angling the distal surface 846 inward can facilitate bone anchor placements in which the auxiliary bone anchor 534 is secured within the lateral mass of a vertebra. In some embodiments, angling the distal surface 846 of the wing 830 inward can provide clearance for a driver instrument on the proximal surface 848 side of the distal portion 830d of the wing 830 to access the bone anchor opening 544.

Figure 8E:
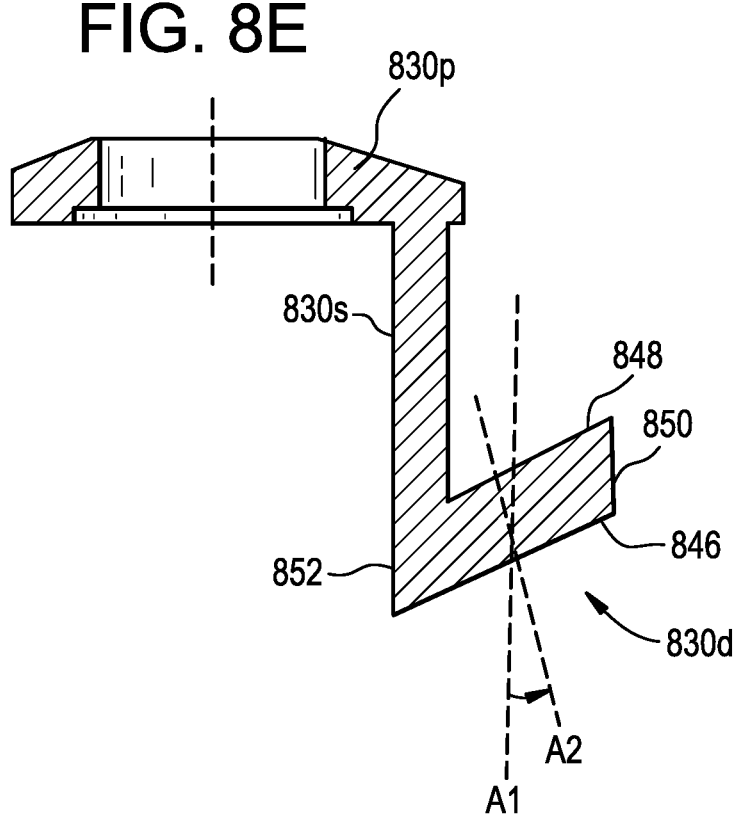
FIG. 8E is another sectional side view of the wing of FIG. 8A.

In an alternative embodiment shown in FIG. 8E, the distal portion 830d can be angled outward (or laterally, when viewed from the perspective of FIG. 8E), such that the medial end 852 of the distal portion is more distal than the free lateral end 850. In this lateral configuration, the distal surface 846 faces outward away from the spanning portion 830s in a lateral direction and the central axis A2 of the bone anchor opening 844 extends outward at a lateral angle with respect to the proximal-distal axis A1 of the spanning portion 830s of the wing 830. Thus, an auxiliary bone anchor 534 can be readily disposed in the bone anchor opening 844 with the distal shaft of the anchor having a lateral trajectory coaxial with, or within a defined cone of angulation with respect to, the central axis A2 of the bone anchor opening 844. In some embodiments, the distal surface 846 of the distal portion 830d of the wing 830 can be obliquely angled, such that the central axis A2 of the bone anchor opening 844 can extend at a lateral angle between 5 to 20 degrees inclusive (e.g., 15 degrees). In such embodiments, angling the distal surface 846 outward can facilitate bone anchor placements in which the auxiliary bone anchor 534 is secured in a lateral location. Such embodiments can be useful to accommodate the bony anatomy of the lumbar spine.

An exemplary method of using the bone anchor assemblies disclosed herein is described below.

The procedure can begin by forming an open or percutaneous incision in the patient to access a bone in which a bone anchor assembly is to be implanted. The bone can be prepared to receive the bone anchor assembly as known in the art. For example, a pedicle of a vertebra can be prepared using standard awl, probe, and tap steps.

The bone anchor can then be advanced into the bone. If the user feels that the purchase of the bone anchor is inadequate, or that auxiliary fixation would otherwise be desirable, an auxiliary fixation member can be added to the bone anchor assembly.

For example, referring to the embodiment of FIGS. 2A-2M, a spinal rod 206 can be seated in the receiver member 204 and a closure mechanism 208 can be threaded down onto the rod. A wing 230 can then be positioned over the closure mechanism 208 and secured in place with the nut 232. One or more auxiliary bone anchors 234 can be inserted through the wing 230 to attach the construct to the bone at a second location (or at more than two locations). The method can include bending or flexing the wing 230 to better fit the receiver member 204 or bone surface, for example by squeezing legs 258 of the wing together to increase a height of the wing.

As another example, referring to the embodiment of FIGS. 3A-3I, a plate 360 can be seated in the receiver member 304 and a rod 306 can be positioned over the plate and secured to the receiver member using a closure mechanism 308. A cap 372 can be used if the height of the rod 306 and plate 360 exceeds the design height of the receiver member 304. One or more auxiliary bone anchors 334 can be inserted through the plate 360 to attach the construct to the bone at a second location (or at more than two locations). The method can include bending or flexing the plate 360 to better fit the receiver member 304 or bone surface.

As another example, referring to the embodiment of FIGS. 4A-4E, a spinal rod 406 can be seated in the receiver member 404 and a closure mechanism 408 can be threaded down onto the rod. A collar 476 can then be positioned over the receiver member 404 and secured to a hook 474 using a locking screw 478. The hook 474 can be hooked onto a portion of the patient's anatomy or a nearby implant to augment the fixation of the bone anchor assembly 400. The method can include bending or flexing the hook 474 to better fit the receiver member 404 or the anatomy or implant.

As another example, referring to the embodiment of FIGS. 5A-5H, a spinal rod 506 can be seated in the receiver member 504 and a closure mechanism 508 can be threaded down onto the rod. A wing 530 can be positioned over the closure mechanism 508 and secured in place with the nut 532. As discussed above, the wing 530 can include a distal portion 530*d* that is angled to the right side of the wing 530. Thus, when the wing is positioned lateral to a bone anchor disposed to the left of the spinal midline when viewed from a posterior vantage point, an auxiliary bone anchor 534 can be inserted through the bone anchor opening 544 and driven into bone with a caudal trajectory. When the wing is positioned lateral to a bone anchor disposed to the right of the spinal midline when viewed from a posterior vantage point, an auxiliary bone anchor 534 can be inserted through the bone anchor opening 544 and driven into bone with a cephalad trajectory.

As another example, referring to the embodiment of FIGS. 7A-7F, a spinal rod 506 can be seated in the receiver member 504 and a closure mechanism 508 can be threaded down onto the rod. A wing 730 can be positioned over the closure mechanism 508 and secured in place with the nut 532. As discussed above, the wing 730 can include a distal portion 730*d* that is angled to the left side of the wing 730. Thus, when the wing is positioned lateral to a bone anchor disposed to the left of the spinal midline when viewed from a posterior vantage point, an auxiliary bone anchor 534 can be inserted through the bone anchor opening 744 and driven into bone with a cephalad trajectory. When the wing is positioned lateral to a bone anchor disposed to the right of the spinal midline when viewed from a posterior vantage point, an auxiliary bone anchor 534 can be inserted through the bone anchor opening 744 and driven into bone with a caudal trajectory.

As another example, referring to the embodiment of FIGS. 8A-8D, a spinal rod 506 can be seated in the receiver member 504 and a closure mechanism 508 can be threaded down onto the rod. A wing 830 can be positioned over the closure mechanism 508 and secured in place with the nut 532. As discussed above in some embodiments, the wing 830 can include a distal portion 830*d* that is angled to inward towards the spanning portion 830*s* of the wing 830. Thus, when the wing is positioned lateral to a bone anchor disposed to the left or right of the spinal midline when viewed from a posterior vantage point, an auxiliary bone anchor 534 can be inserted through the bone anchor opening 844 and driven into bone with a medial trajectory. In some embodiments, the wing 830 can include a distal portion 830*d* that is angled to outward away from the spanning portion 830*s* of the wing 830. Thus, when the wing is positioned lateral to a bone anchor disposed to the left or right of the spinal midline when viewed from a posterior vantage point, an auxiliary bone anchor 534 can be inserted through the bone anchor opening 844 and driven into bone with a lateral trajectory.

The above steps can be repeated to install additional bone anchor assemblies at the same or at different vertebral levels, with or without auxiliary fixation members. Final tightening or other adjustment of the construct can be performed and the procedure can be completed using known techniques and the incision closed.

In any of the above embodiments or methods, the primary bone anchor can be omitted and the user can rely solely on the one or more auxiliary fixation features to secure the bone anchor assembly. This can advantageously allow the position of the fixation to be completely offset from the receiver member, for example if an initially placed bone anchor needs to be removed due to improper positioning or inadequate purchase, or when the receiver member needs to be positioned over a location where a bone anchor cannot be inserted.

While the methods illustrated and described herein involve a bone anchor assembly placed in the pedicle or lateral mass of vertebral bone, it will be appreciated that the systems and methods herein can be used in any bone, in non-bone tissue, or in non-living or non-tissue objects.

The auxiliary fixation members disclosed herein can be implanted in the same surgical procedure as the bone anchor, receiver member, and spinal rod, or, in the case of revision surgery, during a subsequent surgical procedure.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

As evident from the foregoing, in at least some embodiments, the systems and methods disclosed herein can provide enhanced fixation for a given surgical site, providing greater bone fixation strength at a given location without necessarily requiring moving the fixation to an additional vertebra or skipping/increasing the involved vertebral levels.

The bone anchor assemblies disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The systems and methods disclosed herein can be used in minimally-invasive surgery and/or open surgery. While the systems and methods disclosed herein are generally described in the context spinal surgery, it will be appreciated that the systems and methods disclosed herein can be used with any human or animal implant, in any of a variety of surgeries performed on humans or animals, and/or in fields unrelated to implants or surgery.

Although specific embodiments are described above, it should be understood that numerous changes may be made within the spirit and scope of the concepts described. Accordingly, it is intended that this disclosure not be limited to the described embodiments, but that it have the full scope defined by the language of the following claims.

The invention claimed is:

1. A bone anchor assembly, comprising:
 a bone anchor;
 an auxiliary bone anchor;
 a receiver member coupled to a proximal end of the bone anchor and defining a rod seat configured to receive a rod;
 a closure mechanism threadably mated to the receiver member;
 a wing that includes a proximal portion, a distal portion, and a spanning portion that connects the proximal and distal portions, the proximal portion having a distal-facing surface that opposes a proximal terminal end of the receiver member and defines an opening through which at least a portion of the closure mechanism is disposed, the spanning portion extending vertically along a side wall of the receiver member between the proximal portion and the distal portion, the distal portion extending outward from a distal end of the spanning portion; and a nut configured to threadably engage the closure mechanism to secure the proximal portion of the wing to the receiver member, wherein the distal portion of the wing defines a bone anchor opening through which the auxiliary bone anchor is disposed, and wherein a distal surface of the distal portion of the wing is obliquely angled relative to a proximal-distal axis of the spanning portion to face one of a medial direction or a lateral direction, wherein a proximal surface of the distal portion is distal to a distal surface of the proximal portion.

2. The bone anchor assembly of claim 1, wherein the distal surface of the distal portion of the wing is obliquely angled inward towards the proximal-distal axis of the spanning portion.

3. The bone anchor assembly of claim 1, wherein the distal surface of the distal portion of the wing is obliquely angled outward away from the proximal-distal axis of the spanning portion.

4. The bone anchor assembly of claim 1, wherein a proximal surface of the distal portion of the wing is substantially parallel to the distal surface of the distal portion.

5. The bone anchor assembly of claim 1, wherein the auxiliary bone anchor has a threaded proximal head and the bone anchor opening has a partially threaded interior surface configured to engage the threaded proximal head of the auxiliary bone anchor such that the auxiliary bone anchor is capable of being locked at any angle amongst a plurality of selectable angles relative to the central axis of the bone anchor opening.

6. The bone anchor assembly of claim 1, wherein the closure mechanism comprises a threaded post having a radially extending shoulder portion and wherein a counter bore is formed about the opening in the distal-facing surface of the proximal portion of the wing to accommodate the radially extending shoulder portion extending at least partially above the proximal terminal end of the receiver member.

7. The bone anchor assembly of claim 1, wherein the bone anchor opening defined in the distal portion of the wing comprises a plurality of bone anchor openings.

8. The bone anchor assembly of claim 1, wherein a central axis of the bone anchor opening is substantially perpendicular to the distal surface of the distal portion such that the central axis of the bone anchor opening extends in the medial direction or the lateral direction.

9. The bone anchor assembly of claim 1, wherein the wing includes a unilateral locking interface, wherein the unilateral locking interface is configured to enable a surgical instrument to hold onto one side of the wing.

10. A bone anchor assembly, comprising:

a bone anchor;

an auxiliary bone anchor;

a receiver member coupled to a proximal end of the bone anchor and defining a rod seat configured to receive a rod;

a closure mechanism threadably mated to the receiver member;

a wing that includes a proximal portion, a distal portion, and a spanning portion that connects the proximal and distal portions, the proximal portion having a distal-facing surface that opposes a proximal terminal end of the receiver member and defines an opening through which at least a portion of the closure mechanism is disposed, the spanning portion extending longitudinally from the proximal portion to the distal portion with a lateral surface of the spanning portion configured to face a side wall of the receiver member, the distal portion extending outward from a distal end of the spanning portion; and a nut configured to threadably engage the closure mechanism to secure the proximal portion of the wing to the receiver member;

wherein the distal portion of the wing defines a bone anchor opening through which the auxiliary bone anchor is disposed; and wherein a distal surface of the distal portion of the wing is obliquely angled relative to a proximal-distal axis of the spanning portion within a plane that extends through the proximal-distal axis of the spanning portion perpendicular to the lateral surface of the spanning portion; and wherein a proximal surface of the distal portion is distal to a distal surface of the proximal portion.

11. The bone anchor assembly of claim 10, wherein the distal surface of the distal portion of the wing is angled to face towards the spanning portion.

12. The bone anchor assembly of claim 10, wherein the distal surface of the distal portion of the wing is angled to face away from the spanning portion of the wing.

13. The bone anchor assembly of claim 10, wherein the spanning portion is deformable to allow angling of the distal portion of the wing.

* * * * *